US008343945B2

(12) United States Patent
Tamarkin et al.

(10) Patent No.: US 8,343,945 B2
(45) Date of Patent: Jan. 1, 2013

(54) CARRIERS, FORMULATIONS, METHODS FOR FORMULATING UNSTABLE ACTIVE AGENTS FOR EXTERNAL APPLICATION AND USES THEREOF

(75) Inventors: Dov Tamarkin, Ness Ziona (IL); Doron Friedman, Karmei Yosef (IL); Meir Eini, Ness Ziona (IL); Alex Besonov, Rehovot (IL); Helena Shifrin, Rehovot (IL)

(73) Assignee: Foamix Ltd., Rehovot (IL)

( * ) Notice: Subject to any disclaimer, the term of this patent is extended or adjusted under 35 U.S.C. 154(b) by 23 days.

(21) Appl. No.: 12/795,164

(22) Filed: Jun. 7, 2010

(65) Prior Publication Data
US 2010/0310476 A1 Dec. 9, 2010

Related U.S. Application Data

(63) Continuation of application No. PCT/IB2008/003932, filed on Dec. 8, 2008.

(60) Provisional application No. 61/012,414, filed on Dec. 7, 2007, provisional application No. 61/103,500, filed on Oct. 7, 2008.

(51) Int. Cl.
*A61K 31/16* (2006.01)
*A61K 31/65* (2006.01)
*A61K 9/12* (2006.01)

(52) U.S. Cl. .................. 514/152; 514/613; 424/45
(58) Field of Classification Search .................. 514/152, 514/613; 424/45
See application file for complete search history.

(56) References Cited

U.S. PATENT DOCUMENTS

| | | | |
|---|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki et al. |
| 3,563,098 A | 2/1971 | Weber, III |
| 3,574,821 A | 4/1971 | Pfirrmann et al. |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |

(Continued)

FOREIGN PATENT DOCUMENTS

AU 198780257 9/1986

(Continued)

OTHER PUBLICATIONS

"Minocycline" accessed on Oct. 21, 2011 at en.wikipedia.org/wiki/Minocycline.*
"Reaction rate," accessed at en.wikipedia.org/wiki/Reaction_rate on Dec. 18, 2011.*
"HLB Systems", pharmcal.tripod.com/ch17.htm, Accessed Sep. 17, 2010, pp. 1-3.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds,"Antimicrobial Agents and Chemotherapy, vol. 35, No. 9, pp. 1799-1803, 1991.

(Continued)

*Primary Examiner* — James H. Alstrum-Acevedo
(74) *Attorney, Agent, or Firm* — Fish & Richardson P.C.

(57) ABSTRACT

The present disclosure teaches unique formulations for topical administration of tetracycline antibiotics, in which the tetracycline antibiotics remain stable.

25 Claims, 1 Drawing Sheet

U.S. PATENT DOCUMENTS

| | | |
|---|---|---|
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |

| | | |
|---|---|---|
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |

| | | | |
|---|---|---|---|
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang et al. |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |

| | | | |
|---|---|---|---|
| 7,654,415 B2 | 2/2010 | van der Heijden | |
| 7,682,623 B2 | 3/2010 | Eini et al. | |
| 7,700,076 B2 | 4/2010 | Tamarkin et al. | |
| 7,704,518 B2 | 4/2010 | Tamarkin et al. | |
| 7,820,145 B2 | 10/2010 | Tamarkin et al. | |
| 7,960,416 B2 | 6/2011 | Sato et al. | |
| 2001/0006654 A1 | 7/2001 | Cannell et al. | |
| 2001/0027218 A1 | 10/2001 | Stern et al. | |
| 2001/0027981 A1 | 10/2001 | Vlodek | |
| 2001/0036450 A1 | 11/2001 | Verite et al. | |
| 2002/0002151 A1 | 1/2002 | Ono et al. | |
| 2002/0004063 A1 | 1/2002 | Zhang | |
| 2002/0013481 A1 | 1/2002 | Schonrock et al. | |
| 2002/0015721 A1 | 2/2002 | Simonnet et al. | |
| 2002/0032171 A1 | 3/2002 | Chen et al. | |
| 2002/0035046 A1 | 3/2002 | Lukenbach et al. | |
| 2002/0035070 A1 | 3/2002 | Gardlik et al. | |
| 2002/0035087 A1 | 3/2002 | Barclay | |
| 2002/0035182 A1 | 3/2002 | L'Alloret et al. | |
| 2002/0039591 A1 | 4/2002 | Dahle | |
| 2002/0044659 A1 | 4/2002 | Ohta | |
| 2002/0045659 A1 | 4/2002 | Michelet et al. | |
| 2002/0048798 A1 | 4/2002 | Avery et al. | |
| 2002/0058010 A1 | 5/2002 | Picard-Lesboueyries et al. | |
| 2002/0072544 A1 | 6/2002 | Miller et al. | |
| 2002/0090386 A1 | 7/2002 | Halswanter et al. | |
| 2002/0098215 A1 | 7/2002 | Douin et al. | |
| 2002/0111281 A1 | 8/2002 | Vishnupad | |
| 2002/0117516 A1 | 8/2002 | Lasserre et al. | |
| 2002/0134376 A1 | 9/2002 | Castro et al. | |
| 2002/0136755 A1 | 9/2002 | Tyrrell et al. | |
| 2002/0143188 A1 | 10/2002 | Garvey et al. | |
| 2002/0153390 A1 | 10/2002 | Vlodek | |
| 2002/0165170 A1 | 11/2002 | Wilson et al. | |
| 2002/0182162 A1 | 12/2002 | Shahinpoor et al. | |
| 2002/0187181 A1 | 12/2002 | Godbey et al. | |
| 2002/0198136 A1 | 12/2002 | Mak et al. | |
| 2003/0006193 A1 | 1/2003 | Ikeda et al. | |
| 2003/0031693 A1 | 2/2003 | Breton et al. | |
| 2003/0053961 A1 | 3/2003 | Eccard | |
| 2003/0077297 A1 | 4/2003 | Chen et al. | |
| 2003/0078172 A1 | 4/2003 | Guiramand et al. | |
| 2003/0114520 A1 | 6/2003 | Pereira et al. | |
| 2003/0118515 A1 | 6/2003 | Jew et al. | |
| 2003/0130247 A1 | 7/2003 | Gans et al. | |
| 2003/0175232 A1 | 9/2003 | Elliott et al. | |
| 2003/0175315 A1 | 9/2003 | Yoo et al. | |
| 2003/0180347 A1 | 9/2003 | Young et al. | |
| 2003/0185839 A1 | 10/2003 | Podolsky | |
| 2003/0194379 A1 | 10/2003 | Brugger et al. | |
| 2003/0195128 A1 | 10/2003 | Deckman et al. | |
| 2003/0206955 A1 | 11/2003 | Sonneville-Aubrun et al. | |
| 2003/0215472 A1 | 11/2003 | Bonda et al. | |
| 2004/0018228 A1 | 1/2004 | Fischell et al. | |
| 2004/0028752 A1 | 2/2004 | Kamm et al. | |
| 2004/0038912 A1 | 2/2004 | Michelet et al. | |
| 2004/0053797 A1 | 3/2004 | Chen et al. | |
| 2004/0058878 A1 | 3/2004 | Walker | |
| 2004/0063787 A1 | 4/2004 | Villanueva | |
| 2004/0067970 A1 | 4/2004 | Foster et al. | |
| 2004/0072638 A1 | 4/2004 | Enos et al. | |
| 2004/0076651 A1 | 4/2004 | Brocks et al. | |
| 2004/0078896 A1 | 4/2004 | Hellyer et al. | |
| 2004/0079361 A1 | 4/2004 | Clayton et al. | |
| 2004/0105825 A1 | 6/2004 | Henning | |
| 2004/0120917 A1 | 6/2004 | Perrier et al. | |
| 2004/0127554 A1 | 7/2004 | Ghisalberti | |
| 2004/0138179 A1 | 7/2004 | Goldstein et al. | |
| 2004/0151671 A1 | 8/2004 | Abram et al. | |
| 2004/0151756 A1 | 8/2004 | Richards et al. | |
| 2004/0161447 A1 | 8/2004 | Paul | |
| 2004/0184992 A1 | 9/2004 | Abram | |
| 2004/0185123 A1 | 9/2004 | Mazzio et al. | |
| 2004/0191196 A1 | 9/2004 | Tamarkin | |
| 2004/0192754 A1 | 9/2004 | Shapira et al. | |
| 2004/0195276 A1 | 10/2004 | Fuchs | |
| 2004/0197276 A1 | 10/2004 | Takase et al. | |
| 2004/0197295 A1 | 10/2004 | Riedel et al. | |
| 2004/0219122 A1 | 11/2004 | Masuda et al. | |
| 2004/0219176 A1 | 11/2004 | Dominguez | |
| 2004/0220187 A1 | 11/2004 | Stephenson et al. | |
| 2004/0229813 A1 | 11/2004 | DiPiano et al. | |
| 2004/0234475 A1 | 11/2004 | Lannibois-Drean et al. | |
| 2004/0241099 A1 | 12/2004 | Popp et al. | |
| 2004/0247531 A1 | 12/2004 | Riedel et al. | |
| 2004/0253275 A1 | 12/2004 | Eini et al. | |
| 2004/0258627 A1 | 12/2004 | Riedel et al. | |
| 2004/0265240 A1 | 12/2004 | Tamarkin et al. | |
| 2005/0002976 A1 | 1/2005 | Wu | |
| 2005/0013853 A1 | 1/2005 | Gil-Ad et al. | |
| 2005/0031547 A1* | 2/2005 | Tamarkin et al. | 424/45 |
| 2005/0042182 A1 | 2/2005 | Arkin et al. | |
| 2005/0054991 A1 | 3/2005 | Tobyn et al. | |
| 2005/0069566 A1 | 3/2005 | Tamarkin et al. | |
| 2005/0074414 A1 | 4/2005 | Tamarkin et al. | |
| 2005/0075407 A1 | 4/2005 | Tamarkin et al. | |
| 2005/0079139 A1 | 4/2005 | Jacques et al. | |
| 2005/0084551 A1 | 4/2005 | Jensen et al. | |
| 2005/0085843 A1 | 4/2005 | Opolski et al. | |
| 2005/0101936 A1 | 5/2005 | Gonzales et al. | |
| 2005/0106197 A1 | 5/2005 | Blin et al. | |
| 2005/0123494 A1 | 6/2005 | Swaile et al. | |
| 2005/0123496 A1 | 6/2005 | Shah et al. | |
| 2005/0186142 A1 | 8/2005 | Tamarkin et al. | |
| 2005/0186147 A1 | 8/2005 | Tamarkin et al. | |
| 2005/0189377 A1 | 9/2005 | Lanzendorfer et al. | |
| 2005/0196414 A1 | 9/2005 | Dake et al. | |
| 2005/0205086 A1 | 9/2005 | Tamarkin et al. | |
| 2005/0207837 A1 | 9/2005 | Kosh et al. | |
| 2005/0222090 A1 | 10/2005 | Cheng et al. | |
| 2005/0232869 A1 | 10/2005 | Tamarkin et al. | |
| 2005/0244342 A1 | 11/2005 | Friedman et al. | |
| 2005/0244354 A1 | 11/2005 | Speron | |
| 2005/0245902 A1 | 11/2005 | Cornish et al. | |
| 2005/0252995 A1 | 11/2005 | Westphal et al. | |
| 2005/0255048 A1 | 11/2005 | Hirsh et al. | |
| 2005/0258189 A1 | 11/2005 | Peterson et al. | |
| 2005/0266035 A1 | 12/2005 | Healy et al. | |
| 2005/0268416 A1 | 12/2005 | Sommers | |
| 2005/0271596 A1 | 12/2005 | Friedman et al. | |
| 2005/0271598 A1 | 12/2005 | Friedman et al. | |
| 2005/0276836 A1 | 12/2005 | Wilson et al. | |
| 2005/0281755 A1 | 12/2005 | Zarif et al. | |
| 2005/0281766 A1 | 12/2005 | Martin et al. | |
| 2005/0285912 A1 | 12/2005 | Delametter et al. | |
| 2005/0287081 A1 | 12/2005 | Aust et al. | |
| 2006/0008432 A1 | 1/2006 | Scarampi et al. | |
| 2006/0014990 A1 | 1/2006 | Kuechler et al. | |
| 2006/0018937 A1 | 1/2006 | Friedman et al. | |
| 2006/0018938 A1 | 1/2006 | Neubourg | |
| 2006/0029565 A1 | 2/2006 | Xu et al. | |
| 2006/0051301 A1 | 3/2006 | Galopin et al. | |
| 2006/0054634 A1 | 3/2006 | Mekata | |
| 2006/0057168 A1 | 3/2006 | Larm et al. | |
| 2006/0088561 A1 | 4/2006 | Eini et al. | |
| 2006/0099151 A1 | 5/2006 | Neubourg | |
| 2006/0108377 A1 | 5/2006 | Glynn et al. | |
| 2006/0110418 A1 | 5/2006 | Johnson | |
| 2006/0114745 A1 | 6/2006 | Ollmann et al. | |
| 2006/0121073 A1 | 6/2006 | Goyal et al. | |
| 2006/0140984 A1 | 6/2006 | Tamarkin et al. | |
| 2006/0140990 A1 | 6/2006 | Bortz et al. | |
| 2006/0160713 A1 | 7/2006 | Sekine et al. | |
| 2006/0165616 A1 | 7/2006 | Brock et al. | |
| 2006/0177392 A1 | 8/2006 | Walden | |
| 2006/0193789 A1 | 8/2006 | Tamarkin et al. | |
| 2006/0193813 A1 | 8/2006 | Simonnet | |
| 2006/0204446 A1 | 9/2006 | Lulla et al. | |
| 2006/0222675 A1 | 10/2006 | Sabnis et al. | |
| 2006/0233721 A1 | 10/2006 | Tamarkin et al. | |
| 2006/0239937 A2 | 10/2006 | Neubourg | |
| 2006/0251684 A1 | 11/2006 | Annis et al. | |
| 2006/0254597 A1 | 11/2006 | Thompson | |
| 2006/0263323 A1 | 11/2006 | Hoang et al. | |
| 2006/0269485 A1 | 11/2006 | Friedman et al. | |
| 2006/0272199 A1 | 12/2006 | Licciardello et al. | |
| 2006/0275218 A1 | 12/2006 | Tamarkin et al. | |
| 2006/0275221 A1 | 12/2006 | Tamarkin et al. | |

| | | | | | |
|---|---|---|---|---|---|
| 2006/0285912 A1 | 12/2006 | Eini et al. | DE | 1 882 100 | 11/1963 |
| 2006/0292080 A1 | 12/2006 | Abram et al. | DE | 1926796 | 11/1965 |
| 2007/0009607 A1 | 1/2007 | Jones | DE | 4140474 | 6/1993 |
| 2007/0017696 A1 | 1/2007 | Lin et al. | DE | 10009233 | 8/2000 |
| 2007/0020213 A1 | 1/2007 | Tamarkin et al. | DE | 10138495 A1 | 2/2003 |
| 2007/0020304 A1 | 1/2007 | Tamarkin et al. | DE | 102004016710 | 10/2005 |
| 2007/0027055 A1 | 2/2007 | Koivisto et al. | DE | 2 608 226 | 9/2007 |
| 2007/0036831 A1 | 2/2007 | Baker | EP | 0156507 A1 | 10/1985 |
| 2007/0059253 A1 | 3/2007 | Popp et al. | EP | 0186453 A2 | 7/1986 |
| 2007/0069046 A1 | 3/2007 | Eini et al. | EP | 211550 | 2/1987 |
| 2007/0071688 A1 | 3/2007 | Illel et al. | EP | 0214865 A2 | 3/1987 |
| 2007/0098647 A1 | 5/2007 | Neubourg | EP | 0216856 | 4/1987 |
| 2007/0134174 A1 | 6/2007 | Irwin et al. | EP | 0270316 | 6/1988 |
| 2007/0140999 A1 | 6/2007 | Puglia et al. | EP | 297436 A2 | 1/1989 |
| 2007/0142263 A1 | 6/2007 | Stahl et al. | EP | 326196 | 8/1989 |
| 2007/0148112 A1* | 6/2007 | Dingley et al. | EP | 336812 | 10/1989 |
| 2007/0148194 A1 | 6/2007 | Amiji et al. | EP | 0404376 | 12/1990 |
| 2007/0154402 A1 | 7/2007 | Trumbore et al. | EP | 414920 | 3/1991 |
| 2007/0160548 A1 | 7/2007 | Riccardi et al. | EP | 0484530 A1 | 5/1992 |
| 2007/0237724 A1 | 10/2007 | Abram et al. | EP | 485299 | 5/1992 |
| 2007/0253911 A1 | 11/2007 | Tamarkin et al. | EP | 0488089 A1 | 6/1992 |
| 2007/0264317 A1 | 11/2007 | Yosha et al. | EP | 504301 | 9/1992 |
| 2007/0271235 A1 | 11/2007 | Frank et al. | EP | 0506197 A1 | 9/1992 |
| 2007/0280891 A1 | 12/2007 | Tamarkin et al. | EP | 0 528 190 | 2/1993 |
| 2007/0281999 A1 | 12/2007 | Fox et al. | EP | 0535327 A1 | 4/1993 |
| 2007/0292355 A1 | 12/2007 | Tamarkin et al. | EP | 0 552 612 | 7/1993 |
| 2007/0292359 A1 | 12/2007 | Friedman et al. | EP | 0569773 A2 | 11/1993 |
| 2007/0292461 A1 | 12/2007 | Tamarkin et al. | EP | 0598412 A2 | 5/1994 |
| 2008/0008397 A1 | 1/2008 | Kisilev | EP | 0 662 431 | 7/1995 |
| 2008/0015263 A1 | 1/2008 | Bolotin et al. | EP | 0676198 | 10/1995 |
| 2008/0015271 A1 | 1/2008 | Abram et al. | EP | 0 738 516 | 10/1996 |
| 2008/0031907 A1 | 2/2008 | Tamarkin et al. | EP | 0 757 959 | 2/1997 |
| 2008/0031908 A1 | 2/2008 | Aubrun-Sonneville et al. | EP | 0824911 | 2/1998 |
| 2008/0035155 A1 | 2/2008 | Dahl | EP | 829259 | 3/1998 |
| 2008/0044444 A1 | 2/2008 | Tamarkin et al. | EP | 928608 | 7/1999 |
| 2008/0058055 A1 | 3/2008 | LeMay et al. | EP | 0979654 A1 | 2/2000 |
| 2008/0063682 A1* | 3/2008 | Cashman et al. ............. 424/423 | EP | 0993827 A1 | 4/2000 |
| 2008/0069779 A1 | 3/2008 | Tamarkin et al. | EP | 1025836 A1 | 8/2000 |
| 2008/0131378 A1 | 6/2008 | Keller et al. | EP | 1055425 A2 | 11/2000 |
| 2008/0138293 A1 | 6/2008 | Tamarkin et al. | EP | 1215258 | 6/2002 |
| 2008/0138296 A1 | 6/2008 | Tamarkin et al. | EP | 1287813 | 3/2003 |
| 2008/0152596 A1 | 6/2008 | Friedman et al. | EP | 1308169 | 5/2003 |
| 2008/0153789 A1 | 6/2008 | Dmowski et al. | EP | 1 375 386 | 1/2004 |
| 2008/0166303 A1 | 7/2008 | Tamarkin et al. | EP | 1428521 | 6/2004 |
| 2008/0167376 A1 | 7/2008 | Bar-Or et al. | EP | 1438946 | 7/2004 |
| 2008/0181854 A1 | 7/2008 | Eini et al. | EP | 1189579 | 9/2004 |
| 2008/0188445 A1 | 8/2008 | Muldoon et al. | EP | 1475381 | 11/2004 |
| 2008/0188446 A1* | 8/2008 | Muldoon et al. .............. 514/154 | EP | 1483001 | 12/2004 |
| 2008/0193762 A1 | 8/2008 | Dubertret et al. | EP | 1500385 | 1/2005 |
| 2008/0206155 A1 | 8/2008 | Tamarkin et al. | EP | 1 537 916 | 6/2005 |
| 2008/0206159 A1 | 8/2008 | Tamarkin et al. | EP | 1600185 | 11/2005 |
| 2008/0206161 A1 | 8/2008 | Tamarkin et al. | EP | 1 670 698 | 6/2006 |
| 2008/0241079 A1 | 10/2008 | Neubourg | EP | 1734927 | 12/2006 |
| 2008/0253973 A1 | 10/2008 | Tamarkin et al. | EP | 1758547 | 3/2007 |
| 2008/0255498 A1 | 10/2008 | Houle | EP | 1584324 | 11/2007 |
| 2008/0260655 A1 | 10/2008 | Tamarkin et al. | EP | 1889609 | 2/2008 |
| 2008/0292560 A1 | 11/2008 | Tamarkin et al. | FR | 2 591 331 | 6/1987 |
| 2008/0299220 A1 | 12/2008 | Tamarkin et al. | FR | 2 640 942 | 6/1990 |
| 2008/0311167 A1 | 12/2008 | Oronsky et al. | FR | 2736824 | 1/1997 |
| 2008/0317679 A1 | 12/2008 | Tamarkin et al. | FR | 2774595 A | 8/1999 |
| 2009/0041680 A1 | 2/2009 | Tamarkin et al. | FR | 2 789 371 | 8/2000 |
| 2009/0068118 A1 | 3/2009 | Eini et al. | FR | 2 793 479 | 11/2000 |
| 2009/0093514 A1 | 4/2009 | Statham et al. | FR | 2 814 959 | 4/2002 |
| 2009/0130029 A1 | 5/2009 | Tamarkin et al. | FR | 2 833 246 | 6/2003 |
| 2009/0131488 A1 | 5/2009 | Harel et al. | FR | 2 843 373 | 2/2004 |
| 2009/0175799 A1 | 7/2009 | Tamarkin et al. | FR | 2 845 672 | 4/2004 |
| 2009/0180970 A1 | 7/2009 | Tamarkin et al. | FR | 2 848 998 | 6/2004 |
| 2009/0291917 A1 | 11/2009 | Akama et al. | FR | 2915891 | 11/2008 |
| 2009/0317338 A1 | 12/2009 | Tamarkin et al. | GB | 808104 | 1/1959 |
| 2010/0111879 A1 | 5/2010 | Tamarkin et al. | GB | 808105 A | 1/1959 |
| 2010/0221194 A1 | 9/2010 | Loupenok | GB | 922930 | 4/1963 |
| 2011/0002857 A1 | 1/2011 | Tamarkin et al. | GB | 933486 A | 8/1963 |
| 2011/0002969 A1 | 1/2011 | Serraima et al. | GB | 998 490 | 7/1965 |
| 2011/0212033 A1* | 9/2011 | Tamarkin et al. ............... 424/43 | GB | 1026831 | 4/1966 |
| 2011/0268665 A1* | 11/2011 | Tamarkin et al. ............... 424/43 | GB | 1033299 | 6/1966 |
| | | | GB | 1081949 A | 9/1967 |
| | FOREIGN PATENT DOCUMENTS | | GB | 1121358 | 7/1968 |
| CA | 2422244 | 9/2003 | GB | 1 162 684 | 8/1969 |
| CH | 639913 | 12/1983 | GB | 1170152 A | 11/1969 |

| | | | | | | |
|---|---|---|---|---|---|---|
| GB | 1 201 918 | 8/1970 | | JP | 2006/036317 | 2/2006 |
| GB | 1347950 | 2/1974 | | JP | 2006/103799 | 4/2006 |
| GB | 1 351 761 | 5/1974 | | JP | 2006525145 | 11/2006 |
| GB | 1 351 762 | 5/1974 | | JP | 2007131539 | 5/2007 |
| GB | 1 353 381 | 5/1974 | | JP | S48-92282 | 12/2007 |
| GB | 1376649 | 12/1974 | | KR | 143232 | 7/1998 |
| GB | 1397285 | 6/1975 | | KR | 2001003063 | 1/2001 |
| GB | 1408036 | 10/1975 | | RU | 2277501 | 6/2006 |
| GB | 1 457 671 | 12/1976 | | UA | 66796 | 6/2004 |
| GB | 2004746 A | 4/1979 | | WO | WO-8201821 | 6/1982 |
| GB | 1561423 | 2/1980 | | WO | WO-86/05389 | 9/1986 |
| GB | 2114580 | 8/1983 | | WO | WO-88/01863 | 3/1988 |
| GB | 2153686 | 8/1985 | | WO | WO-8801502 | 3/1988 |
| GB | 2172298 | 9/1986 | | WO | WO-88/08316 | 11/1988 |
| GB | 2 206 099 | 12/1988 | | WO | WO-89/06537 | 7/1989 |
| GB | 2166651 | 5/1996 | | WO | WO-90/05774 | 5/1990 |
| GB | 2337461 | 11/1999 | | WO | WO-91/11991 | 8/1991 |
| GB | 2 367 809 | 4/2002 | | WO | WO-92/00077 | 1/1992 |
| GB | 2 406 330 | 3/2005 | | WO | 92/05763 | 4/1992 |
| GB | 2406791 | 4/2005 | | WO | WO-9205142 A1 | 4/1992 |
| IL | 49491 | 9/1979 | | WO | WO-92/11839 | 7/1992 |
| IL | 0152486 A0 | 5/2003 | | WO | WO-9325189 | 12/1993 |
| JP | 60001113 | 4/1978 | | WO | WO-9406440 | 3/1994 |
| JP | 55069682 | 5/1980 | | WO | WO-96/03115 | 2/1996 |
| JP | 57044429 | 3/1982 | | WO | WO-96/19921 | 7/1996 |
| JP | 56039815 | 4/1984 | | WO | WO-9624325 A1 | 8/1996 |
| JP | 61275395 | 12/1986 | | WO | 96/26711 | 9/1996 |
| JP | 62241701 | 10/1987 | | WO | WO-96/27376 | 9/1996 |
| JP | 6357511 | 3/1988 | | WO | WO-96/39119 | 12/1996 |
| JP | 63119420 | 5/1988 | | WO | WO-9703638 | 2/1997 |
| JP | 01100111 | 4/1989 | | WO | WO-97/39745 | 10/1997 |
| JP | 01156906 | 6/1989 | | WO | WO-9817282 | 4/1998 |
| JP | 02184614 A | 7/1990 | | WO | WO-98/18472 | 5/1998 |
| JP | 2255890 | 10/1990 | | WO | WO-98/19654 | 5/1998 |
| JP | 04282311 | 10/1992 | | WO | WO-98/21955 | 5/1998 |
| JP | 4312521 | 11/1992 | | WO | WO-98/23291 | 6/1998 |
| JP | 5070340 | 3/1993 | | WO | WO-98/36733 | 8/1998 |
| JP | 5213734 | 8/1993 | | WO | 98/52536 | 11/1998 |
| JP | 6100414 | 4/1994 | | WO | WO-99/08649 | 2/1999 |
| JP | H06-263630 | 6/1994 | | WO | WO-99/20250 | 4/1999 |
| JP | 6329532 | 11/1994 | | WO | WO-99/37282 | 7/1999 |
| JP | 2007/155667 | 6/1995 | | WO | WO-9953923 | 10/1999 |
| JP | 7215835 | 8/1995 | | WO | WO-9953923 A1 | 10/1999 |
| JP | 8501529 | 2/1996 | | WO | WO-00/09082 | 2/2000 |
| JP | 2008040899 | 2/1996 | | WO | WO-00/15193 | 3/2000 |
| JP | 8119831 | 5/1996 | | WO | WO-0023051 | 4/2000 |
| JP | 8165218 | 6/1996 | | WO | WO-0033825 | 6/2000 |
| JP | 8277209 | 10/1996 | | WO | WO-0038731 | 7/2000 |
| JP | 09 084855 | 3/1997 | | WO | WO-00/61076 | 10/2000 |
| JP | 9099553 | 4/1997 | | WO | WO-00/76461 | 12/2000 |
| JP | 9110636 | 4/1997 | | WO | 01/05366 | 1/2001 |
| JP | 10114619 | 5/1998 | | WO | WO-01/08681 | 2/2001 |
| JP | 3050289 | 9/1998 | | WO | WO-0110961 A1 | 2/2001 |
| JP | 2010/332456 | 12/1998 | | WO | 01/53198 | 7/2001 |
| JP | 11501045 | 1/1999 | | WO | 01/54212 | 7/2001 |
| JP | 11250543 | 9/1999 | | WO | WO-01/54679 | 8/2001 |
| JP | 2000017174 A | 1/2000 | | WO | WO-0162209 A2 | 8/2001 |
| JP | 2000080017 | 3/2000 | | WO | WO-01/70242 A2 | 9/2001 |
| JP | 2000128734 | 5/2000 | | WO | 01/82890 | 11/2001 |
| JP | 2000191429 | 7/2000 | | WO | WO-01/82880 | 11/2001 |
| JP | 2000239140 | 9/2000 | | WO | WO-0185102 A2 | 11/2001 |
| JP | 2000351726 | 12/2000 | | WO | WO-0185128 | 11/2001 |
| JP | 2000354623 | 12/2000 | | WO | WO-0195728 A1 | 12/2001 |
| JP | 2001002526 | 1/2001 | | WO | WO-02/00820 | 1/2002 |
| JP | 2001019606 | 1/2001 | | WO | WO-0215860 | 2/2002 |
| JP | 2001072963 | 3/2001 | | WO | WO-0215873 | 2/2002 |
| JP | 2002012513 | 1/2002 | | WO | WO-02/28435 | 4/2002 |
| JP | 2002047136 | 2/2002 | | WO | WO-02/41847 | 5/2002 |
| JP | 2002/524490 | 8/2002 | | WO | WO-02/43490 | 6/2002 |
| JP | 2002302419 | 10/2002 | | WO | WO-02/062324 | 8/2002 |
| JP | 2003/012511 | 1/2003 | | WO | WO-02078667 A1 | 10/2002 |
| JP | 2003055146 | 2/2003 | | WO | WO-02087519 | 11/2002 |
| JP | 2004047136 A | 2/2004 | | WO | WO-03000223 A1 | 1/2003 |
| JP | 2004250435 | 9/2004 | | WO | WO-03002082 | 1/2003 |
| JP | 2004/348277 | 12/2004 | | WO | 03/013984 | 2/2003 |
| JP | 2005314323 | 11/2005 | | WO | WO-03051294 A2 | 6/2003 |
| JP | 2005/350378 | 12/2005 | | WO | WO-03/055445 | 7/2003 |
| JP | 2005350378 | 12/2005 | | WO | WO-03053292 A1 | 7/2003 |
| JP | 2006008574 | 1/2006 | | WO | WO-03055454 | 7/2003 |

| | | |
|---|---|---|
| WO | 03/070301 | 8/2003 |
| WO | 03/071995 | 9/2003 |
| WO | WO-03075851 A2 | 9/2003 |
| WO | 03/097002 | 11/2003 |
| WO | WO-03092641 A1 | 11/2003 |
| WO | WO-2004017962 | 3/2004 |
| WO | WO-2004037197 | 5/2004 |
| WO | WO-2004037225 A2 | 5/2004 |
| WO | 2004/003284 | 8/2004 |
| WO | WO-2004064769 | 8/2004 |
| WO | WO-2004064833 A1 | 8/2004 |
| WO | WO-2004071479 A1 | 8/2004 |
| WO | WO-2004078158 | 9/2004 |
| WO | WO-2004078896 A1 | 9/2004 |
| WO | WO-2004093895 | 11/2004 |
| WO | WO-2004112780 A1 | 12/2004 |
| WO | WO-2005011567 A2 | 2/2005 |
| WO | WO-2005018530 A2 | 3/2005 |
| WO | WO-2005032522 A1 | 4/2005 |
| WO | 2005/065652 | 7/2005 |
| WO | WO-2005063224 | 7/2005 |
| WO | WO-2005065652 A1 | 7/2005 |
| WO | WO-2005076697 A2 | 8/2005 |
| WO | WO-2005097068 A1 | 10/2005 |
| WO | WO-2005102282 A1 | 11/2005 |
| WO | WO-2005102539 A1 | 11/2005 |
| WO | WO-2005117813 A1 | 12/2005 |
| WO | WO-2006003481 A2 | 1/2006 |
| WO | WO-2006010589 A2 | 2/2006 |
| WO | WO-2006011046 | 2/2006 |
| WO | WO-2006020682 A1 | 2/2006 |
| WO | WO-2006028339 A1 | 3/2006 |
| WO | WO-2006031271 A2 | 3/2006 |
| WO | WO-2006045170 A2 | 5/2006 |
| WO | WO-2006079632 A1 | 8/2006 |
| WO | WO-2006081327 | 8/2006 |
| WO | WO-2006091229 A2 | 8/2006 |
| WO | WO-2006100485 A1 | 9/2006 |
| WO | WO-2006120682 A2 | 11/2006 |
| WO | WO-2006121610 A2 | 11/2006 |
| WO | WO-2006122158 | 11/2006 |
| WO | WO-2006129161 A2 | 12/2006 |
| WO | WO-2006131784 A1 | 12/2006 |
| WO | WO-2007007208 A2 | 1/2007 |
| WO | WO-2007012977 A2 | 2/2007 |
| WO | WO-2007023396 A2 | 3/2007 |
| WO | WO-2007031621 A2 | 3/2007 |
| WO | WO-2007039825 A2 | 4/2007 |
| WO | WO-2007050543 A2 | 5/2007 |
| WO | WO-2007054818 A2 | 5/2007 |
| WO | WO-2007072216 A2 | 6/2007 |
| WO | WO-2007085899 A2 | 8/2007 |
| WO | WO-2007085902 A2 | 8/2007 |
| WO | WO-2007099396 A2 | 9/2007 |
| WO | WO-2007111962 A2 | 10/2007 |
| WO | WO-2008008397 A2 | 1/2008 |
| WO | WO-2008010963 | 1/2008 |
| WO | 2008/041045 | 4/2008 |
| WO | WO-2008038147 A2 | 4/2008 |
| WO | WO-2008075207 A2 | 6/2008 |
| WO | WO-2008087148 A2 | 7/2008 |
| WO | WO-2008110872 A2 | 9/2008 |
| WO | 2008/152444 | 12/2008 |
| WO | WO-2009007785 A2 | 1/2009 |
| WO | WO-2009069006 A2 | 6/2009 |
| WO | WO-2009072007 A2 | 6/2009 |
| WO | WO-2009087578 A2 | 7/2009 |
| WO | WO-2009090495 A2 | 7/2009 |
| WO | WO-2009090558 A2 | 7/2009 |
| WO | WO-2009098595 A2 | 8/2009 |
| WO | WO-2011039637 | 4/2011 |
| WO | WO-2011039638 | 4/2011 |

OTHER PUBLICATIONS

Austria, et al., "Stability of Vitamin C Derivatives in Solution and Arct, et al., "Common Cosmetic Hydrophilic Ingredients as Penetration Modifiers of Flavonoids", International Journal of Cosmetic Science, 24(6):357-366 (2002)—Abstract, 1 page.
Arisan, www.arisankimya.com/kozmetik.htm Accessed Dec. 10, 2008, 8 pages.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631. Topical Formulations", Journal of Pharmaceutical and Biomedical Analysis, 15:795-801 (1997).
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfactants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstract, 1 page.
Bronopol. Revtrieved online on Jun. 4, 2011. <chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (3 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carbowax 1000MSDS; http://www.sciencelab.com/xMSDS-Polyethylene.sub.--glycol.sub.--1000-9926- 622. Accessed Dec. 13, 2008, 6 pages.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Cheshire, et al., Disorders of Sweating, www.medscape.com, Semin Neurol 23(4):399-406, 2003.
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
Colloidal Silica. Retrieved online on Jun. 4, 2011. www.grace.com/engineeredmaterials/materialsciences/colloidalsilica/default.aspx >. Copyright 2011. 2 pages.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Dawber, et al., "Hypertrichosis in Females Applying Minoxidil Topical Solution and in Normal Controls", JEADV, 17:271-275 (2003).

Denatonium Benzoate www.newdruginfo.com/pharmaceopeia/usp28/v28230/usp28nf23s0.sub.--m- 22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

disorder. (2007). In the American Heritage Dictionary of the English Language. Retrieved from www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006 111(2): 145-51.

Edwards, "Imiquimod in Clinical Practice", J. Am Acad Dermatol., 43(1, Pt 2):S12-S17 (2000)—Abstract, 1 page.

Emulsifiers with HLB values. www.theherbarie.com/files/resources-center/formulating/Emulsifiers- .sub.--HLB.sub.--Values.pdf accessed Aug. 5, 2009 (3 pps).

English machine translation of JP-08165218 (1996) 9 pages.

English translation of abstract for Japanese Patent Publication No. 4892282 (1992) 1 page.

Esposito, E. et al. "Nanosystems for Skin Hydration: A Comparative Study." International Journal of Cosmetic Science. 29. 2007. pages. 39-47.

Ethanol, Accessed www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.

Ethylene Oxide Derivatives: An Essence of Every Industry. A definition of Emulsifier. www.emulsifiers.in/ethylene_oxide_derivatives2.htm. Accessed Jul. 12, 2011. 3 pages.

European Official Action, European Patent Application No. 06831721.3, Feb. 3, 2009, 9 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fonatana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irradiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Hall, Karla, "Diaper Area Hemangiomas: A Unique Set of Concerns," members.tripod.com/.about.Michelle.sub.--G/diaper.html, Dec. 1, 2008, 8 pages.

Hallstar. Retrieved online on Jun. 4, 2011. www.hallstar.com/pis.php?product=1H022>. 1 page.

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Imiquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hashim, et al. "Tinea versicolor and visceral leishmaniasis," Int J Dermatol., Apr. 1994; 33(4), pp. 258-259 (abstract only). 2 pages.

Heart Failure, The Merck Manual, 2008 www.merck.com/mmhe/sec03/ch025/ch025a.html>> 12 pages.

Hepburn, NC., "Cutaneous leishmaniasis," Clin Exp Dermatol, Jul. 2000; 25(5), pp. 363-370 (abstract only), 2 pages.

Hill, Randall M. (Ed.) Silicone Surfactants, Table of Contents and Chapter 7, "Silicone Surfactants: Applicants in the Personal Care Industry," by David T. Floyd, 1999 (30 Pages).

ibabydoc.com/online/diseaseeczema.asp., Atopic Dermatitis, Copyright 2000, 6 pages.

web.archive.org/web/20000106225413/http://pharmacy.wilkes.edu/kibbeweb/lab7.html, Characteristics of Surfactants and Emulsions, Jan. 29, 2010, 5 pages.

www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. it03.net/com/oxymatrine/down/1249534834.pdf>. Aug. 15, 2009. 3 pages.

Innocenzi, Daniele et al., "An Open-Label Tolerability and Efficacy Study of an Aluminum Sesquichlorhydrate Topical Foam in Axillary and Palmar Primary Hyperhidrosis," Dermatologic Therapy, vol. 21, S27-S30, 2008.

Izquierdo, P. et al. "Formation and Stability of Nano-Emulsions Prepared Using the Phase Inversion Temperature Method." University of Barcelona. Sep. 17, 2001. 3 page.

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5, Abstract, 1 page.

Kang, et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kathon.TM. CG (product information sheet by Rohm and Haas, Jun. 2006). 9 pages.

Kim, "Stability of Minoxidil in Aqueous Solution", Yakhak Hoechi, 30(5):228-231 (1986)—Abstract, 2 pages.

Kinnunen, Contact Dermatitis Sep. 1989; 21(3): 154-8, Abstract, 2 pages.

Kleber, M.D., H.D. et al., "Treatment of Patients with Substance Use Disorders, Second Edition," pp. 1-276, 2006.

Koerber, S., "Humectants and Water Activity," Water Activity News, 2000, ISSN No. 1083-3943. 8 pages.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery" in *Water-Soluble Polymers*, American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck Index, An Encyclopedia of Chemicals, Drugs, and Biologicals. $13^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," //mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
"Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate www.makingcosmetics.com/sunscreens/OM-Cinnamate-p102.html accessed Sep. 26, 2009, 1 page.

Pakpayat, et al., "Formulation of Ascorbic Acid Microemulstions with Alkyl Polyglycosides", European Journal of Pharmaceutics and Biopharmaceutics, 72:444-452 (2009).
Paula. ww.cosmeticscop.com/cosmetic-ingredient-dictionary/definition/259/c12-15-alkyl-benzoate.aspx. Printed Oct. 24, 2010. 1 page.
Pendergrass, Gynecol Obstet. Invest. 1996:42(3):178-82, Abstract, 2 pages.
Prescription Information for Aldara, Mar. 2007 (29 pages).
prevent. (2007). In the American Heritage Dictionary of the English Language. Retrieved from www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Raymond, Iodine as an Aerial Disinfectant, Journal of Hygiene, vol. 44, No. 5 (May 1946), pp. 359-361.
Receptacle. Merriam Webster. www.merriam-webster.com/dictionary/receptacle. Accessed Jul. 12, 2011. 1 page.
Richwald, "Imiquimod", Drugs Today, 35(7):497 (1999)—Abstract, 1 page.
Rosacea, clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "*Malassezia furfur*: a fungus belonging to the physiological skin flora and its relevance in skin disorders," Curtis., Jan. 1997; 59(1), pp. 21-4 (abstract), 2 pages.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only). 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Sigma Aldrich, "HLB-Numbers in Lithography Nanopatterning," www.sigmaaldrich.com/materials-science/micro-and-nanoelectronics/l-ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from www.oxforddictionaries.com/definition/silicone?view=uk. 1 page.
Simovic, S. et al., "The influence of Processing Variables on Performance of O/W Emulsion Gels Based on Polymeric Emulsifier (Pemulen ÒTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, web.archive.org/web/20030810230608/http://www.skinbio.com/cpserum.- html, Dec. 1, 2008, 21 pages.
Skin Deep Cosmetics. PPG-40-PEG-60 Lanolin Oil www.cosmeticsdatabase.com/ingredient/722972/PPG-40-PEG-60__Lanolin_Oil/?ingred06=722972. Accessed May 19, 2010, 3 pages.

Sonneville-Aubrun, O. et al. "Nanoemulsions: A New Vehicle for Skincare Products." Advances in Colloid and Interface Science. 108-109.. 2004. pp. 145-149.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only). 1 page.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle, et al., "Uptake of Minoxidil from a New Foam Formulation Devoid of Propylene Glycol to Hamster Ear Hair Follicles", Abstract 606, 1 page.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Surfactant. Wikipedia—wikipedia.org/wiki/surfactant. Printed Oct. 24, 2010. 7 pages.

Sweetman, Sean C. Martindale: The Complete Drug Reference. 33rd Edition. London. Pharmaceutical Press. Jun. 21, 2002. pags. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate-1. Acute toxicity of hydrocortisone 17-butyrate 21-propionate and its analogues in mice, rats and dogs (author's trans), J Toxicol Sci., Jul. 1981; 6 Suppl: 1-16, Abstract, 1 page.

Tata, et al., "Penetration of Minoxidil from Ethanol Propylene Glycol Solutions: Effect of Application Volume on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Torres-Rodriguez, JM., "New topical antifungal drugs," Arch Med Res. 1993 Winter; 24(4), pp. 371-375 (abstract), 2 pages.

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Tzen, Jason T.C. et al. "Surface Structure and Properties of Plant Seed Oil Bodies." Department of Botany and Plant Sciences, University of California, Riverside, California 92521. Journal of Cell Biology, 117(2):327-335, Apr. 15, 1992. 9 pages.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 4, 2010, Tamarkin.
U.S. Appl. No. 61/363,577, filed Jul. 12, 2010, Eini.

"Burn patients need vitamin D supplements." *Decision News Media,* Jan. 23, 2004, http://www.nutraingredients.com/Research/Burn-patients-need-vitamin-D-supplements, Accessed: May 5, 2010.

'Niram Chemicals' [online]. Niram Chemicals, [retrieved on Jul. 17, 2012]. Retrieved from the Internet: <URL: http://www.indiamart.com/niramchemicals/chemicals.html>, 7 pages.

Barry and Badal, "Stability of minocycline, doxycycline, and tetracycline stored in agar plates and microdilution trays," *Current Microbiology,* 1978, 1:33-36.

Hargreaves, "Chemical Formulation, An Overview of Surfactant-Based Preparations Used in Everyday Life", *The Royal Society of Chemistry,* pp. 114-115 (2003).

Hormones. http://www.greenwillowtree.com/Page.bok?file=libido.html. Jan. 2001.

hydroxyethylcellulose. http: //terpconnect.umd.edu/-choi/MSDS/Sigma-Aldrich/HYDROXYETHYL%20CELLULOSE, 5 pages, Jan. 14, 2004.

Jan. "Troubled Times: Detergent Foam." http://zetatalk.com/health/theall7c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Lebwohl et al., "A randomized, double-blind, placebo-controlled study of clobestasol propionate 0.05% foam in the treatment of nonscalp psoriasis," *International Journal of Dermatology,* 2002, 41(5): 269-274.

Martindale. 33 ed. London, Bath Press, 2002. pp. 1073 and 1473.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Neutrogena. http://www.cosmetoscope.com/2010/04/neutrogena-clinical-with-johnson-johnsons-cytomimic-techology/. Published Apr. 28, 2010. Accessed Sep. 11, 2010, 5 pages.

Nietz, "Molecular orientation at surfaces of solids," *J. Phys. Chem.,* 1928, 32(2): 255-269.

Oil. Dictionary of Chemistry. Editor: DWA Sharp. Copyright 1990.

Padhi et al., "Phospho-olicines as positive-electrode materials for rechargeable lithium batteries," *J. Electrochemical Soc.,* 1997, 144(4): 1188-1194.

Ravet et al., "Electroactivity of natural and synthetic triphylite," *J. of Power Sources,* 2001, 97-98: 503-507

Shrestha et al., Forming properties of monoglycerol fatty acid esters in nonpolar oil systems, *Langmuir,* 2006, 22: 8337-8345.

Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.

Stehle et al., Uptake of minoxidil from a new foam formulation devoid of propylene glycol to hamster ear hair follicles, *J. Invest. Dermatol.,* 2005, 124(4), A101.

Surfactant. Chemistry Glossary. http://chemistry.about.com/od/chemistryglossary/g/surfactant.htm, 2012, 1 page.

Third Party Submission for U.S. Appl. No. 12/014,088, Feb. 4, 2009, 4 pages, cited by other.
Yamada and Chung, "Crystal Chemistry of the Olivine-Type Li(Mn$y$Fe$_{1-y}$)PO$_4$ and (Mn$y$Fe$1-y$)PO$_4$ as Possible 4 V Cathode Materials for Lithium Batteries," J. Electrochemical Soc., 2001, 148(8): A960-967.
"Coal tars and coal-tar pitches," Report on Carcinogens, Twelfth Edition, 2011, 3 pages.
Adisen et al. "Topical tetracycline in the treatment of acne vulgaris," J Drugs Dermatol., 2008, 7:953-5.
Baskaran et al., "Poloxamer-188 improves capillary blood flow and tissue viability in a cutaneous burn wound," J. Surg. Res., 2001, 101(1):56-61.
Bell-Syer et al. "A systematic review of oral treatments for fungal infections of the skin of the feet," J. Dermatolog. Treat., 2001, 12:69-74.
Boehm et al. 1994, "Synthesis of high specific activity [.sup.3 H]-9-cis-retinoic acid and its application for identifying retinoids with unusual binding properties," J. Med. Chem., 37:408-414.
Carapeti et al., "Topical diltiazem and bethanechol decrease anal sphincter pressure and heal anal fissures without side effects," Dis Colon Rectum, 2000, 43(10):1359-62.
Cook and Mortensen, "Nifedipine for treatment of anal fissures," Dis Colon Rectum, 2000, 43(3):430-1.
Dumortier et al., "A review of poloxamer 407 pharmaceutical and pharmacological characteristics," Pharmaceutical Res., 2006, 23(12):2709-2728.
Ebadi et al., "Healing effect of topical nifedipine on skin wounds of diabetic rats," DARU, 2003, 11(1):19-22.
Effendy and Maibach. "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, pp. 103-120.
Fantin et al., "Critical influence of resistance to streptogramin B-type antibiotics on activity of RP 59500 (Quinupristin-dalfopristin) in experimental endocarditis due to Staphylococcus aureus,"Antimicrob Agents and Chemothery, 1999, 39:400-405.
Fluhr et al., "Glycerol accelerates recovery of barrier function in vivo," Acta Derm. Venereol,. 1999, 79:418-21.
Garti et al. "Sucrose Esters microemulsions," J. Molec. Liquids, 1999, 80:253-296.
Hammer et al. "Anti-Microbial Activity of Essential Oils and other Plant extracts," J. Applied Microbiology, 1999, 86:985-990.
Hwang et al. "Isolation and identification of mosquito repellents in Artemisia vulgaris,"J. Chem. Ecol., 11: 1297-1306, 1985.
Knight et al., "Topical diltiazem ointment in the treatment of chronic anal fissure," Br. J. Surg., 2001, 88(4):553-6.
Kucharekova et al., "Effect of a lipid-rich emollient containing ceramide 3 in experimentally induced skin barrier dysfunction," Contact Dermatitis, Jun. 2002, pp. 331-338.
Leive et al, "Tetracyclines of various hydrophobicities as a probe for permeability of Escherichia coli outer membrane," Antimicrobial Agents and Chemotherapy, 1984, 25:539-544.
Luepke and Kemper, "The HET-CAM Test: An Alternative to the Draize Eye Test," FD Chem. Toxic., 1986, 24:495-196.
Osborne and Henke, "Skin Penetration Enhancers Cited in the Technical Literature," Pharm. Technology, Nov. 1997, pp. 58-86.
Padi. "Minocycline prevents the development of neuropathic pain, but not acute pain: possible anti-inflammatory and antioxidant mechanisms," Eur J. Pharmacol, 2008, 601:79-87.
Palamaras and Kyriakis, "Calcium antagonists in dermatology: a review of the evidence and research-based studies," Derm. Online Journal, 2005, 11(2):8.
Passi et al., Lipophilic antioxidants in human sebum and aging, Free Radical Research, 2002, pp. 471-477.
Perrotti et al., "Topical Nifedipine With Lidocaine Ointment vs. Active Control for Treatment of Chronic Anal Fissure," Dis Colon Rectum, 2002, 45(11):1468-1475.
Repa et al. "All-trans-retinol is a ligand for the retinoic acid receptors," Proc. Natl. Acad Sci, USA, 90: 7293-7297, 1993.

Ruledge, "Some corrections to the record on insect repellents and attractants," J. Am. Mosquito Control Assoc, 1988, 4(4): 414-425.
Sakai et al., "Characterization of the physical properties of the stratum corneum by a new tactile sensor," Skin Research and Technology, Aug. 2000, pp. 128-134.
Schaefer, "Silicone Surfactants," Tenside, Surfactants, Deterg., 1990, 27(3): 154-158.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Smith, "Hydroxy acids and skin again," Soap Cosmetics Chemical Specialties, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," European J. Pharm. Biopharm., 1998, 46(3):265-71.
Todd et al. "Volatile Silicone Fluids for Cosmetics," 91 Cosmetics and Toiletries, 1976, 27-32.
Torma et al., "Biologic activities of retinoic acid and 3, 4-dehydroretinoic acid in human keratinoacytes are similar and correlate with receptor affinities and transactivation properties," J. Invest. Dermatology, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," J. Chem., Biol. 1922, 52:525.
Van Cutsem et al., "The antiinflammatory efects of ketoconazole," J. AM. ACAD. Dermatol., 1991, (2 pt 1):257-61.
Wang and Chen, "Preparation and surface active properties of biodegrabable dextrin derivative surfactants," Colloids and Surfaces A: Physicochemical and Engineering Aspects, 2006, 281(1-3): 190-193.
Weindl et al., "Hyaluronic acid in the treatment and prevention of skin diseases: molecular biological, pharmaceutical and clinical aspects," Skin Pharmacology and Physiology, 2004, pp. 207-213.
Xynos et al., "Effect of nffedipine on rectoanal motility," Dis Colon Rectum, 1996, 39(2):212-6.
Yamada et al., "Candesartan, an angiotensin II receptor antagonist, suppresses pancreatic inflammation and fibrosis in rats," J. Pharmacol. Exp. Ther., 2003, 307(1)17-23.
Paragraph E.3.1 of regulation (EC) No. 2003 (See Directive 67/548/EEC OJ 196, 16.8, 1967, p. 1.
Tzen et al., Lipids, proteins and structure of seed oil bodies from diverse species; Plant Physiol., 1993, 101:267-276.
Brown et al. " Structural dependence of flavonoid interactions with Cu2+ inos: implications for their antioxidant properties," Biochem. J., 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," Int. Immunol., 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its protoprotection of skin," J Invest Dermatol, 2005, 125:826-32.
International Search Report/Written Opinion and International Preliminary Report on Patentability in International Application No. PCT/IB2008/003932. International Search Report dated Sep. 25, 2009 and International Preliminary Report on Patentability issued Jun. 8, 2010. 12 pages.

* cited by examiner

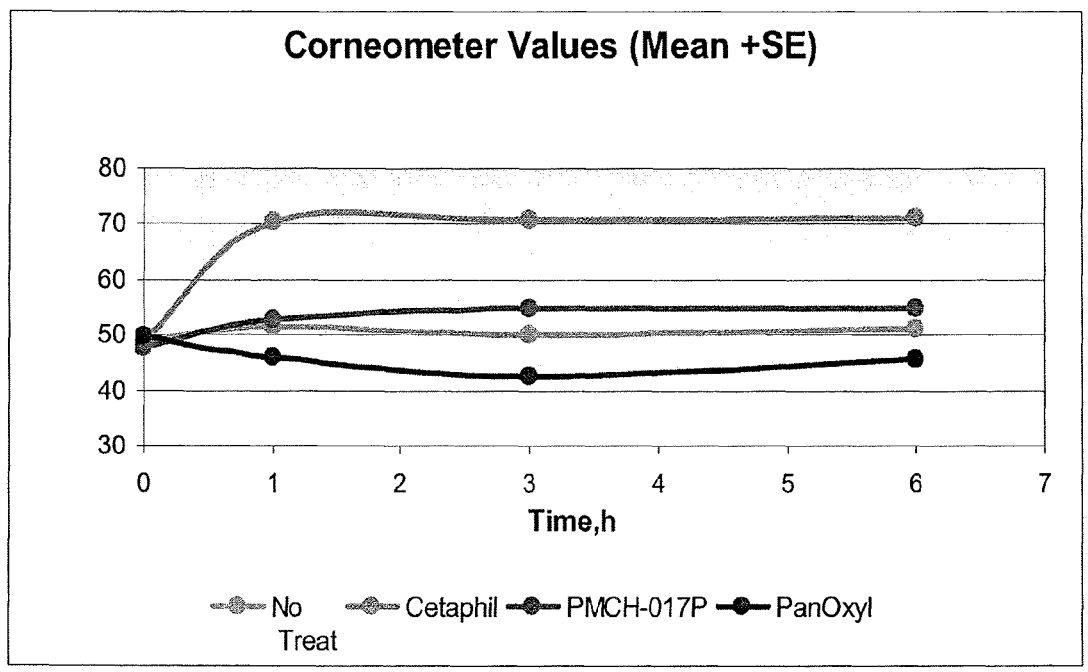

CARRIERS, FORMULATIONS, METHODS FOR FORMULATING UNSTABLE ACTIVE AGENTS FOR EXTERNAL APPLICATION AND USES THEREOF

CROSS REFERENCE TO RELATED APPLICATIONS

This application is a continuation under 35 U.S.C. §120 of PCT/IB2008/03932, filed on Dec. 8, 2008, which claims priority under 35 U.S.C. §119(e) of U.S. Provisional Patent Application No. 61/012,414, filed on Dec. 7, 2007, entitled "Carriers, Formulations, Methods for Formulating Unstable Active Agents for External Application and Uses Thereof", and U.S. Provisional Patent Application No. 61/103,500, filed on Oct. 7, 2008 entitled "Oil and Liquid Silicone Carriers and Formulations for External and Body Cavity Application of Active Agents and Uses Thereof".

FIELD

This disclosure relates to materials, carriers, formulations and methods for formulating unstable active agents in topical compositions, which are suitable, inter alia, for applying to the skin or to mucosal surfaces and can be used for treating topical, mucosal and or systemic disorders in mammals. The disclosure further relates to vehicles which are suitable, inter alia, for delivery for a wide range of active pharmaceutical and cosmetic agents and methods for their use.

BACKGROUND

The skin is the largest organ of a mammalian body, serving many important functions, such as regulating body temperature, maintaining water and electrolyte balance, and sensing painful and pleasant stimuli. The skin is adapted to keep dangerous substances from entering the body and provides a shield from the harmful effects of the sun. Any deterioration in skin health may have important consequences on a person's physical and mental health. Many teenagers suffer from acne, which is an inflammatory disease of the skin, caused by changes in the pilosebaceous units and results in scarring or hyperpigmentation of the skin. Several types of skin disorder manifest themselves as rashes and lead to itching. The itching and rashes may develop as the result of infection or irritation or from an immune system reaction. Additionally, the skin is prone to microbial infection and parasitic infestation.

External topical administration is an important route for the administration of drugs in both systemic and topical disease treatment. Many groups of drugs, including, for example, antibiotic, anti-fungal, anti-inflammatory, anesthetic, analgesic, anti-allergic, corticosteroid, retinoid and anti-proliferative medications are preferably administered in hydrophobic media, namely ointment. However, ointments often form an impermeable barrier, thus in the treatment of a topical wound, metabolic products and excreta from these wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds. A further problem of non aqueous compositions is achieving formulations in which the active agent is stable.

Some active agents are known to be generally unstable or susceptible to isomerisation or to breakdown, resulting in loss of activity and the use of stabilizers, anti oxidants antimicrobials and buffers and the like in aqueous compositions to protect active or cosmetic agents is known. The problems of protecting active pharmaceutical and cosmetic agents in waterless environments, such as polar compositions are multifold and can vary according to the type of waterless environment and the nature of the agent being used. It has been surprisingly found that factors like small levels of acid residues in the raw materials can be significant in influencing agent stability. Similarly, the presence of low levels of metal ions can act to catalyze reactions or breakdown. Likewise, the presence of agents in a waterless environment that results in ionization or leads to oxidation can act to cause reactions or breakdown. There is therefore a need for simple and elegant solutions to stabilize active ingredients in a waterless or substantially environment.

It would be particularly advantageous and there is an unmet need to have a waterless vehicle additive that is suitable for use not merely one type of active pharmaceutical ingredient (API) but is adaptable for use with one or more API's from a wide range of different types of API's with relatively minimal or minor adjustment.

Foams and, in particular, foam emulsions are complicated systems which do not form under all circumstances. Changes in foam emulsion composition, such as by the addition of active ingredients may destabilize the foam. There is, therefore, a need for a foam composition, which provides desirable properties to the skin and can remain stable whilst accommodating a variety of active ingredients.

Formulations based on oil or ointment or emollients have a number of useful attributes making them suitable candidates for topical pharmaceutical and cosmetic compositions including foamable compositions. They are inherently stable and inert which are clearly desirable characteristics. They are able to moisturize and soften the skin and in appropriate amounts can act as a protective or barrier layer and can form a barrier to water. By appropriate formulation they can act to improve drug delivery to the skin and yet remain resistant to being washed off. On the other hand they are by their nature greasy materials and can be difficult to formulate particularly into a topical foamable composition that can deliver substantially uniform and stable composition or foam that ameliorates or overcomes the look and feel of a greasy material, especially where that composition is waterless or substantially so. It is further a problem to incorporate into such a vehicle pharmaceutically effective amounts of one or more active pharmaceutical ingredients such that they are uniformly present throughout the formulation and are effectively delivered without the use of an alcohol in the formulation.

On one level it is far from simple or obvious to produce waterless foamable compositions that when released produce foams of quality suitable for pharmaceutical or cosmetic application. On a further level having realized a carrier that will produce a waterless foam of quality there is an additional difficulty to be overcome, namely how to adapt the formula and achieve a formulation, which can accept a range of various active pharmaceutical and cosmetic agents such that the composition and active agent are stable and the foam produced remains of quality. Specifically, one of the challenges in preparing such waterless or substantially waterless foamable compositions is ensuring that the active pharmaceutical or therapeutic agent does not react, isomerizes or otherwise break down to any significant extent during is storage and use.

Particularly, there remains an unmet need for improved, easy to use, stable and non-irritating foam formulations, with unique therapeutic or beneficial properties containing a stable or stabilized active pharmaceutical or cosmetic agent.

There remains an unmet need for improved, easy to use, stable and non-irritating topical foam formulations containing a stable or stabilized active pharmaceutical or cosmetic agent having a therapeutic or beneficial effect, intended for treatment of dermal and mucosal tissues.

Systemic administration of active agents often leads to allergic responses, side effects and bacterial resistance to the active agents. There thus remains an unmet need for improved, easy to use, stable and non-irritating anti-infective foam formulations comprising active agents, intended for treatment, inter alia, of dermal and mucosal tissues. Particularly, there remains an unmet need for improved, easy to use, stable and non-irritating anti-infective foam formulations, with unique therapeutic properties.

Foams are complex dispersion systems which do not form under all circumstances. Slight shifts in foam composition, such as by the addition of active ingredients, may destabilize the foam. Foams are very complex and sensitive systems and are not formed at will. Mere addition of basic ingredients like oil, surfactant and propellant is far from sufficient to produce foams of quality that are homogenous, stable, breakable upon mechanical force and can be used to provide a shelf stable pharmaceutical or cosmetic composition. Small deviations may lead to foam collapse. Much consideration needs to be given to facilitate the introduction of an active agent, such as examining compatibility and non reactivity with the various excipients and container and determining shelf life chemical stability.

Neubourg (US 2006/0099151), for example, notes that the stability of foam is strongly dependent on the specific composition of the foam forming components, so that even small deviations in the composition may lead to a collapse of the foam. Gordon et al. (U.S. Pat. No. 3,456,052). also teaches that one cannot generate a good quality foam by simply adding a propellant to a mixture of components:

The term "foam" is a general term that encompasses a range of substances. Accordingly, the context in which "foam" is discussed must be examined carefully. The type and quality of the foam is of critical importance. There are many different types of foams and within each foam type there are many levels of qualities. For example, the froth on the head of beer, lather of shampoo, and lather of shaving cream have been loosely described as foam but all are different from one another. At one end of the cosmetic or pharmaceutical foam spectrum the foam can be long lasting and essentially not readily breakable like shaving foams. At the other end of the spectrum the foam can be quick breaking and collapses upon release.

Thermolabile foams are an example of type of quick breaking foam. They can contain significant amounts of thermolabile substances that aid their collapse upon being exposed to an increased temperature for example when applied to a body surface at 37 C. Upon being exposed to the higher temperature they collapse rapidly. Examples are foam formulations that comprise significant amounts of volatile solvents.

Breakable foam is a specialized type of foam. It is a low density foam that is stable on release at least in the short time span of several minutes, which facilitates application to a target area; but can break readily upon the application of shear force such as gentle rubbing to spread easily over a target surface. It is not thermolabile (and does not melt at skin temperature) and nor does it display late or long delayed expansion over minutes.

Some foams expand slowly whilst others do so quickly. Some foams foam immediately and some demonstrate delayed foaming. Some require mechanical lathering and some expulsion by propellant. Whilst they all fall under the so called term "foam" and may appear to have some common ingredients the results and properties of these products are different.

A suitable foamable formulation for a particular application may present challenges at several levels. For example, a foam formulation may require a stable pre foam formulation; a stable pre foam propellant formulation and ultimately delivery an effective measured amount of active agent to a target. Each of these objectives poses its own unique challenges.

The pharmaceutical and cosmetic foams discussed herein are generated in general terms by manufacturing a suitable foamable carrier composition and loading the carrier in a pressurized valved canister with an appropriate propellant. Upon expelling the canister contents a foam can be released. The type, nature and quality of the foam depends inter alia on the carrier composition, the active agent, the propellant and the method of manufacture and storage. Making a stable (physically and chemically) formulation that can be stored in a canister with a propellant that remains stable and can produce a breakable foam of quality on release is far from trivial.

An additional difficulty frequently encountered with propellant foams is their inability to dispense a uniform application of the medically active ingredient throughout the use of the entire aerosol container. This is particularly due to the fact that the active material is not stably dispersed in the foamable composition so that it will have a tendency to settle to the bottom. Further, the dispersed material will sometimes clog the spray dispensing valve to further interfere with the uniform dispensing of the medicament.

SUMMARY

In one aspect, the present disclosure relates to a topical antibiotic composition comprising a foamable pharmaceutical composition and a propellant, the foamable pharmaceutical composition comprising: a) about 0.1% to about 10% by weight of a tetracycline antibiotic; b) about 60% to about 95% by weight of: at least one oily emollient; at least one oil, wherein the oil is a liquid hydrocarbon-based oil; or a combination of at least one oily emollient and at least one oil; c) about 0.01% to about 15% by weight of at least one surfactant, wherein the surface active agent is an ester of a C8-C24 saturated hydrocarbon; d) optionally 0.01% to about 10% by weight of at least one foam adjuvant, wherein the foam adjuvant is a 14C to 18C fatty alcohol; and wherein the tetracycline antibiotic is chemically stable in the foamable pharmaceutical composition when stored for 72 hours at about at least 25° C. after mixing with the pharmaceutical composition; and wherein the weight ratio of the foamable pharmaceutical composition to the propellant is about 100:5 to about 100:35.

In another aspect, the present disclosure relates to a topical antibiotic composition comprising a foamable pharmaceutical composition and a propellant, the foamable pharmaceutical composition comprising: a) about 0.1% to about 10% by weight of minocycline hydrochloride; b) about 60% to about 95% by weight of: at least one emollient selected from the group consisting of PPG-15 stearyl ether, octyldodecanol, diisopropyl adipate, and Cetearyl Octanoate; at least one oil selected from the group consisting of Light mineral oil, MCT oil, Hydrogenated Castor Oil, jojoba oil, and peppermint oil; or a combination of at least one emollient and at least one oil; c) about 0.01% to about 15% by weight of at least one surfactant selected from the group consisting of Glycerol monostearate, Sorbitan monostearate (Span 60), PEG 40 Stearate (Myrj 52), and PEG 100 Stearate (Myrj 59); d) optionally about 0% to about 10% by weight of at least one foam adjuvant selected from the group consisting of Oleyl alcohol, Stearyl alcohol, Myristyl alcohol and Cocoglycerides; and wherein the minocycline hydrochloride is chemically stable in the foamable pharmaceutical composition when stored for 72 hours at about at least 25° C. after mixing with the carrier or with the agent; and wherein the weight ratio of the foamable pharmaceutical composition to the propellant is about 100:5 to about 100:35.

In another aspect, the present disclosure relates to a topical antibiotic composition comprising a foamable pharmaceutical composition and a propellant, the foamable pharmaceutical composition comprising: a) about 0.1% to about 10% by weight of doxycycline hyclate; b) about 60% to about 95% by weight of: at least one emollient selected from the group consisting of PPG-15 stearyl ether, diisopropyl adipate, and Cetearyl Octanoate; at least one oil selected from the group consisting of mineral oil and MCT oil; or a combination of at least one emollient and at least one oil; c) about 0.01% to about 15% by weight of at least one surfactant selected from the group consisting of Glycerol monostearate, Sorbitan monostearate (Span 60), hydrogenated castor oil, and PEG 100 Stearate (Myrj 59); d) optionally about 0% to about 10% by weight of at least one foam adjuvant selected from the group consisting of steryl alcohol, oleyl alcohol, isostearic acid and myrystyl alcohol, wherein the doxycycline hyclate is chemically stable in the foamable pharmaceutical composition when stored for 72 hours at about at least 25° C. after mixing with the foamable pharmaceutical composition; and wherein the weight ratio of the foamable pharmaceutical composition to the propellant is about 100:5 to about 100:35.

In another aspect, the present disclosure relates to a topical antibiotic composition comprising a foamable pharmaceutical composition and a propellant, the foamable pharmaceutical composition comprising: a) about 0.1% to about 10% by weight of doxycycline monohydrate; b) about 60% to about 95% by weight of: at least one emollient selected from the group consisting of Cetearyl Octanoate, Cyclomethicone, PPG-15 Stearyl Ether, Propylene glycol, Octyldodecanol, Glycerol, Diisopropyl adipate, and isostearic acid; at least one oil selected from the group consisting of Light mineral oil, MCT Oil, and hydrogenated castor oil; or a combination of at least one emollient and at least one oil; c) about 0.01% to about 15% by weight of at least one surfactant selected from the group consisting of Glycerol monostearate, Sorbitan monostearate (Span 60), and PEG 100 Stearate (Myrj 59); d) about 1% to about 10% by weight of at least one foam adjuvant selected from the group consisting of oleyl alcohol, stearyl alcohol, myristyl alcohol and stearic acid wherein the doxycycline monohydrate is chemically stable in the foamable pharmaceutical composition when stored for 72 hours at about at least 25° C. after mixing with the foamable pharmaceutical composition; and wherein the weight ratio of the foamable pharmaceutical composition to the propellant is about 100:5 to about 100:35.

In some embodiments, the oily emollient is selected from the group consisting of Cetearyl Octanoate, Cyclomethicone, PPG-15 Stearyl Ether, Propylene glycol, Octyldodecanol, Glycerol, Diisopropyl adipate, and isostearic acid. In other embodiments, the oily emollient is selected from the group consisting of PPG-15 stearyl ether, octyldodecanol, diisopropyl adipate, isostearic acid, and cetearyl octanoate.

As used herein, an oil is a liquid hydrocarbon-based oil. Non-limiting examples of oils include plant-based oils, mineral oils, triglycerides, essential oils, and animal-based oils. Without being limited to any particular theory, oils are believed to be effective in the claimed formulations because they limit the potential for oxidation of the tetracycline antibiotics. In some embodiments of the present disclosure, the oil is selected from the group consisting of plant-based oil, mineral oil, triglyceride, essential oil, and animal-based oil. In other embodiments, the oil is selected from the group consisting of light mineral oil, MCT oil, hydrogenated castor oil, jojoba oil, and peppermint oil.

In some embodiments, the surfactant is a stearic acid derived ester. In other embodiments the surfactant is monoglyceride, diglyceride, or triglyceride, wherein the side chain of the monoglyceride, diglyceride, or triglyceride is a C8-C24 saturated hydrocarbon. In still other embodiments the surfactant is selected from the group consisting of Glycerol monostearate, glycerol palmitostearate, Sorbitan monostearate (Span 60), PEG 40 Stearate (Myrj 52), and PEG 100 Stearate (Myrj 59).

In some embodiments of the present disclosure, the foam adjuvant selected from the group consisting of oleyl alcohol, stearyl alcohol, myristyl alcohol and cocoglycerides.

In some embodiments of the present disclosure, the tetracycline antibiotic is selected from the group consisting of minocycline hydrochloride, doxycycline hyclate, and doxycycline monohydrate.

In some embodiments, the topical antibiotic composition further comprises at least one of ethanol 95%, aluminum starch octenylsuccinate, titanium dioxide, coconut alcohol, and hexylene glycol.

In some embodiments of the present disclosure, chemical stability is determined by observing a color change in the foamable pharmaceutical composition. In some embodiments, chemical stability is determined by measuring at least about 90% by mass of the tetracycline antibiotic at 72 hours compared to time 0. In some embodiments, chemical stability is determined by measuring less than about 1% by mass of 4-epiminocylcine at 72 hours compared to time 0.

In some embodiments of the present disclosure, the topical antibiotic composition further comprises at about 0.1% to about 5% of a silicone oil. In some embodiments the silicone oil is cyclomethicone.

In some embodiments of the present disclosure, the topical antibiotic composition further comprises at least one additional active agent.

Also disclosed herein are methods of treating a bacterial infection comprising topically administering the topical antibiotic composition to a subject in need of treatment. In some embodiments, the topical antibiotic composition is administered to the skin, a mucosal membrane, or a body cavity. In other embodiments, the topical antibiotic composition is administered to a wound, an ulcer, or a burn.

Also disclosed herein are methods of treating and preventing post-surgical adhesions, the method comprising topically administering the topical antibiotic composition to a surgical site of a subject.

In some embodiments of the methods disclosed herein, the topical antibiotic composition further comprises at least one additional active agent.

In some embodiments of the present disclosure, the tetracycline antibiotic is chemically stable in the foamable pharmaceutical composition when stored for 72 hours at about at least 40° C., or at least about 50° C., after mixing with the pharmaceutical composition. In still other embodiments, the tetracycline antibiotic is chemically stable in the foamable pharmaceutical composition when stored for about 3 weeks at about at least 25° C., about at least 40° C., or about at least 50° C.

BRIEF DESCRIPTION OF THE DRAWINGS

FIG. 1 is a graph presenting corneometer values generated using Cetaphil, PanOxyl, PMCH-017P, and no treatment on the skin of healthy volunteers.

DETAILED DESCRIPTION

Many classes of materials may be used in topical pharmaceutical formulations, including emollients, oils, silicone oils, polymeric agents, surface-active agents (i.e., surfactants), solid matter agents, foam adjuvants, solvents, skin penetration enhancers, potent solvents, modulating agents, anti-oxidants, and radical scavengers. However, tetracycline antibiotics are susceptible to oxidation, and are thus generally chemically unstable in topical formulations. Therefore, chemically stable topical formulations of tetracycline antibiotics are generally challenging to prepare. To achieve foamable formulations using propellant that are both physically and chemically stable is a highly complex and unpredictable challenge.

Some embodiments of the present disclosure are directed to a waterless foamable pharmaceutical composition suitable for external administration of minoycline, including:
  at least one least one minocycline-compatible (MC) oily carrier; and
  at least one least one minocycline-compatible (MC) stabilizing agent;
  wherein the stabilizing agent selected from the group consisting of about 0.01% to about 25% by weight of at least one surface-active agent alone or in combination with a foam adjuvant; about 0% to about 5% by weight of at least one polymeric agent and mixtures thereof, wherein MC is defined by minocycline remaining substantially chemically stable, 72 hours after mixing with the carrier or with the agent.

By waterless is meant that the composition contains no or substantially no, free or unassociated or absorbed water. It will be understood by a person of the art that to the extent the waterless solvents and substances miscible with them of the present disclosure are hydrophilic they can contain water in an associated or unfree or absorbed form and may absorb water from the atmosphere and the ability to do so is its hygroscopic water capacity.

In one or more embodiments the carrier comprises an active pharmaceutical or cosmetic agent, which degrades in the presence of water, and in such cases the present of water in the composition is clearly not desirable. Thus, in certain preferred embodiments, the composition is waterless. In other embodiments the active agent may tolerate the presence of a small amount of water and the waterless composition is substantially non-aqueous. The term "substantially non-aqueous" is intended to indicate that the waterless composition has water content preferably below about 2%, such as below about 1.5%.

In some cases the foamable carrier further includes a liquefied or compressed gas propellant at a concentration of about 3% to about 25% by weight.

The waterless foamable pharmaceutical composition may be substantially chemically stable, defined as demonstrating substantially no or minimal color change due to oxidation 72 hours after mixing with the carrier or agent when stored at about at least 25° C.

Additionally, "chemically stable" or "chemical stability" may be defined as demonstrating substantially no or minimal breakdown from oxidation 72 hours after mixing with the carrier or agent when stored at about at least 25° C. Substantially no or minimal breakdown may be determined using HPLC methods disclosed herein or other methods, where the mass of the compound is determined at time 0 (i.e., within about 1 hour after mixing with the carrier or foamable pharmaceutical composition) and about 72 hours after mixing, and wherein at least about 90% by mass of the compound is detected at about 72 hours compared to time 0. Alternatively, degradation products may be determined using HPLC methods disclosed herein or other methods, where the mass of the degradation products is determined at time 0 and about 72 hours after mixing, and wherein less than about 1% by mass of the compound in the mixture is degradation products. When the compound is minocycline, a suitable degradation product for purposes of determining "chemical stability" or "chemically stable" is 4-epiminocycline.

The minocycline may be provided in a substantially homogenous insoluble suspension.

The waterless foamable pharmaceutical composition may further include about 1 to about 2% minocycline hydrochloride.

The at least one oily carrier may be selected from an emollient, an oil and a foam adjuvant.

The emollient may be selected from cyclomethicone; isopropyl myristate, PPG-15 stearyl ether; octyldodecanol; Isohexadecanol, diisopropyl adipate; and Cetearyl Octanoate.

According to some embodiments, the oil is selected from hydrogenated castor oil and MCT oil.

Additionally, the foam adjuvant is selected from Oleyl alcohol, Stearyl alcohol, Myristyl alcohol and Cocoglycerides.

The surfactant may be selected from Glycerol monostearate, Polysorbate 80, Polysorbate 60, Sucrose distearate, Polyoxyl 20 Stearyl Ether, Polyoxyl 2 Stearyl Ether, Sorbitan monostearate, Ester HLB 11, GMS-PEG 100 Stearate, Polysorbate 80, Polysorbate 60, Sorbitan monostearate (Span 60), Methy Glucose Sesquistearate, PEG 40 Stearate (Myrj 52), PEG 100 Stearate (Myrj 59), Montanov S, Glyceryl monostearate, and Sepigel 305.

Some embodiments include a waterless foamable pharmaceutical composition including:
  6% to 80% by weight of at least one oily carrier selected from the group consisting of Cyclomethicone, PPG-15 Stearyl Ether, Octyldodecanol, Isohexadecanol, Diisopropyl adipate, Cetearyl Octanoate, Light mineral oil, and Hydrogenated Castor Oil; and
  0.01% to 25% by weight of at least one stabilizing agent selected from the group consisting of Glycerol monostearate, Polysorbate 60, Polysorbate 80, Sucrose distearate, Polyoxyl 20, Stearyl Ether, Polyoxyl 2 Stearyl Ether, Sorbitan monostearate (Span 60), Methy Glucose Sesquistearate, Myrj 52, Myrj 59, Montanov S, Glyceryl monostearate and Sepigel 305.

A waterless foamable pharmaceutical composition may include:
  10% to 80% by weight of at least one oily carrier selected from the group consisting of Cyclomethicone, PPG-15 Stearyl Ether, Propylene Glycol, Octyldodecanol, Glycerol, Diisopropyl adipate, Cetearyl Octanoate, Light Mineral oil, and MCT oil; and
  0.01% to 6% by weight of at least one stabilizing agent selected from the group consisting of Glycerol monostearate, Sucrose Ester HLB 11, GMS-PEG 100 Stearate, Polysorbate 80, Polysorbate 60, Polysorbate 20, Sorbitan monostearate, Methy Glucose Sesquistearate, PEG 40 Stearate (Myrj 52), PEG 100 Stearate (Myrj 59), Hydrogenated Castor Oil, Steareth-2, Steareth-20, Steareth-21 and Poloxamer 407 (20% gel).

Some embodiments of the present disclosure are directed to a waterless foamable pharmaceutical composition which is substantially chemically stable, defined as demonstrating substantially no or minimal color change due to oxidation 72 hours after mixing with the carrier or agent.

According to some embodiments, the waterless foamable pharmaceutical composition is chemically stable, defined by showing substantially no or minimal breakdown one week after mixing with the carrier or agent.

According to some embodiments, the minocycline is in a substantially homogenous insoluble suspension.

The waterless foamable pharmaceutical composition may further include 3% to 25% by weight of a liquefied or compressed gas propellant.

According to some embodiments, the waterless foamable pharmaceutical composition may further include about 1 to about 2% minocycline hydrochloride.

Additionally, the at least one oily carrier is selected from an emollient, an oil and a foam adjuvant.

According to some embodiments, the emollient is selected from cyclomethicone, isopropyl myristate, PPG-15 stearyl ether; octyldodecanol, Isohexadecanol, diisopropyl adipate, and Cetearyl Octanoate.

According to some embodiments, the oil is selected from hydrogenated castor oil and MCT oil.

According to some embodiments, the foam adjuvant is selected from Oleyl alcohol, Stearyl alcohol, Myristyl alcohol and Cocoglycerides.

According to some embodiments, the surfactant is selected from Glycerol monostearate, Polysorbate 80, Polysorbate 60, Sucrose distearate, Polyoxyl 20 Stearyl Ether, Polyoxyl 2 Stearyl Ether, Sorbitan monostearate, Ester HLB 11, GMS-PEG 100 Stearate, Polysorbate 80, Polysorbate 60, Sorbitan monostearate (Span 60), Methy Glucose Sesquistearate, PEG 40 Stearate (Myrj 52), PEG 100 Stearate (Myrj 59), Montanov S, Glyceryl monostearate, and Sepigel 305.

Some embodiments of the present disclosure are directed to a waterless foamable pharmaceutical composition including:
  6% to 80% by weight of at least one oily carrier selected from the group consisting of Cyclomethicone, PPG-15 Stearyl Ether, Octyldodecanol, Isohexadecanol, Diisopropyl adipate, Cetearyl Octanoate, Light mineral oil, and Hydrogenated Castor Oil; and
  0.01% to 25% by weight of at least one stabilizing agent is selected from the group consisting of Glycerol monostearate, Polysorbate 60, Polysorbate 80, Sucrose distearate, Polyoxyl 20, Stearyl Ether, Polyoxyl 2 Stearyl Ether, Sorbitan monostearate (Span 60), Methy Glucose Sesquistearate, Myrj 52, Myrj 59, Montanov S, Glyceryl monostearate and Sepigel 305.

Other embodiments include a waterless foamable pharmaceutical composition including:
  10% to 80% by weight of at least one oily carrier selected from the group consisting of Cyclomethicone, PPG-15 Stearyl Ether, Propylene Glycol, Octyldodecanol, Glycerol, Diisopropyl adipate, Cetearyl Octanoate, Light Mineral oil, and MCT oil; and
  0.01% to 6% by weight of at least one stabilizing agent selected from the group consisting of Glycerol monostearate, Sucrose Ester HLB 11, GMS-PEG 100 Stearate, Polysorbate 80, Polysorbate 60, Polysorbate 20, Sorbitan monostearate, Methy Glucose Sesquistearate, PEG 40 Stearate (Myrj 52), PEG 100 Stearate (Myrj 59), Hydrogenated Castor Oil, Steareth-2, Steareth-20, Steareth-21 and Poloxamer 407 (20% gel).

Yet further embodiments include a waterless foamable pharmaceutical suitable for external administration of doxycycline, including:
  at least one doxycycline-compatible (DC) oily carrier; and
  at least one doxycycline-compatible (DC) stabilizing agent;
  wherein the stabilizing agent is selected from the group consisting of about 0.01% to about 25% by weight of at least one surface-active agent alone or in combination with a foam adjuvant; about 0% to about 5% by weight of at least one polymeric agent and mixtures thereof, and
  wherein DC is defined by doxycycline remaining substantially chemically stable, 72 hours after mixing with the agent.

Further embodiments relate to a waterless foamable pharmaceutical composition wherein substantially chemically stable is defined as demonstrating substantially no or minimal color change due to oxidation 72 hours after mixing with the carrier or agent.

Further embodiments relate to a waterless foamable pharmaceutical composition, wherein substantially chemically stability is defined as demonstrating substantially no or minimal breakdown one week after mixing with the carrier or agent.

The doxycycline is a substantially homogenous insoluble suspension. The waterless foamable pharmaceutical composition may further include 3% to 25% by weight of a liquefied or compressed gas propellant.

In some cases the waterless foamable pharmaceutical composition further includes 0.5-2% doxycycline. For this purpose the at least one oily carrier may be selected from an emollient, an oil and a foam adjuvant. the emollient may be selected from cyclomethicone; isopropyl myristate, PPG-15 stearyl ether; propylene glycol; octyldodecanol; glycerol; diisopropyl adipate; and diisopropyl adipate; and the foam adjuvant may be selected from Oleyl alcohol, Stearic acid, Stearyl alcohol, Myristyl alcohol and Cocoglycerides. The oil may be selected from light mineral oil and MCT oil. The at least one stabilizing agent is selected from a surfactant and a polymeric agent. The surfactant is selected from Glycerol monostearate, Sucrose Ester HLB 11; GMS-PEG 100 Stearate; Polysorbate 80; Polysorbate 60; Polysorbate 20; Sorbitan monostearate; Methy Glucose Sesquistearate; PEG 40 Stearate (Myrj 52); PEG 100 Stearate (Myrj 59); Hydrogenated Castor Oil; Steareth-2; Steareth-20; Steareth-21 and Poloxamer 407 (20% gel).

Preferred solvents for doxycycline and minocycline include octyl dodecanol, oleyl alcohol and PPG 15 stearyl ester. These compounds are monoalcohols and not polyols.

Further embodiments include a waterless foamable pharmaceutical composition, including:
  6% to 80% by weight of the at least one oily carrier; and
  0.01% to 25% by weight of the at least stabilizing agent.

Further embodiments include a waterless foamable pharmaceutical composition:
  10 to 60% by weight of the at least one oily carrier; and
  0.01% to 10% by weight of the at least stabilizing agent.

Further embodiments include a waterless foamable pharmaceutical composition, including:
  10 to 60% by weight of the at least one oily carrier; and
  0.01% to 6% by weight of the at least stabilizing agent.

Some compositions comprise at least one hydrophobic solvent selected from the group consisting of mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; and essential oils.

Some embodiments include silicone oils, such as, cyclomethicone, polyalkyl siloxane, polyaryl siloxane, polyalkylaryl siloxane, a polyether siloxane copolymer and a poly(dimethylsiloxane)-(diphenyl-siloxane) copolymer. In some embodiments, the silicone oil is cyclomethicone, cyclotetrasiloxane, cyclohexasiloxane, phyenyltrimethicone, Dow corning 246 Fluid (d6+d5) (cyclohexasiloxane & cyclopentasiloxane), Dow Corning 244 Fluid (cyclotetrasiloxane), Cyclomethicone 5-NF (cyclopentasiloxane), stearyl dimethicone, phenyltrimethicone, cetyl dimethicone, caprylyl methicone, PEG/PPG 18/18 dimethicone, or dimethiconol.

According to some embodiments, the at least one surface active agent is selected from the group consisting of at least one non-ionic surfactant and at least one ionic surfactant.

In some cases, the at least one surface active agent is selected from the group consisting of polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkylyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol, sorbitan monolaurate, sorbitan monolaurate a monoglyceride, a diglyceride, isoceteth-20 and a sucrose ester.

The foamable carrier may further including a foam adjuvant selected from the group consisting of a fatty alcohol, a fatty acid and a hydroxyl fatty acid.

According to some embodiments, wherein the foam adjuvant component may include at least one of the group consisting of Oleyl alcohol, Stearyl alcohol, Myristyl alcohol and Cocoglycerides.

According to some further embodiments, the foamable carrier may further include an additional component selected from the group consisting of an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin.

According to some embodiments, the foamable carrier may also include an additional active agent is selected from the group consisting of active herbal extracts, acaricides, age spot and keratose removing agents, allergen, analgesics, local anesthetics, antiacne agents, antiallergic agents, antiaging agents, antibacterials, antibiotic agents, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, nonsteroidal anti-inflammatory agents, oxidizing agents, pediculicides, photodynamic therapy agents, retinoids, sanatives, scabicides, self tanning agents, skin whitening agents, asoconstrictors, vasodilators, vitamins, vitamin D derivatives, wound healing agents and wart removers.

According to some embodiments the antibiotic agent is selected from the group consisting of beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroids, sulfonamides, tetracycline, dicarboxylic acids, antibiotic metals including antibiotic metal ions, oxidizing agents, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds: chlorhexidine acetate, chlorhexidine gluconate and chlorhexidine hydrochloride, picloxydine, alexidine, polihexanide, chlorproguanil hydrochloride, proguanil hydrochloride, metformin hydrochloride, phenformin, buformin hydrochloride, abomycin, acetomycin, acetoxycycloheximide, acetylnanaomycin, an actinoplanes sp. compound, actinopyrone, aflastatin, albacarcin, albacarcin, albofungin, albofungin, alisamycin, alpha-R,S-methoxycarbonylbenzylmonate, altromycin, amicetin, amycin, amycin demanoyl compound, amycine, amycomycin, anandimycin, anisomycin, anthramycin, anti-syphilis immune substance, anti-tuberculosis immune substance, antibiotic from *Eschericia coli*, antibiotics from *Streptomyces refuineus*, anticapsin, antimycin, aplasmomycin, aranorosin, aranorosinol, arugomycin, ascofuranone, ascomycin, ascosin, *Aspergillus flavus* antibiotic, asukamycin, aurantinin, an Aureolic acid antibiotic substance, aurodox, avilamycin, azidamfenicol, azidimycin, bacillaene, a *Bacillus larvae* antibiotic, bactobolin, benanomycin, benzanthrin, benzylmonate, bicozamycin, bravomicin, brodimoprim, butalactin, calcimycin, calvatic acid, candiplanecin, carumonam, carzinophilin, celesticetin, cepacin, cerulenin, cervinomycin, chartreusin, chloramphenicol, chloramphenicol palmitate, chloramphenicol succinate sodium, chlorflavonin, chlorobiocin, chlorocarcin, chromomycin, ciclopirox, ciclopirox olamine, citreamicin, cladosporin, clazamycin, clecarmycin, clindamycin, coliformin, collinomycin, copiamycin, corallopyronin, corynecandin, coumermycin, culpin, cuprimyxin, cyclamidomycin, cycloheximide, dactylomycin, danomycin, danubomycin, delaminomycin, demethoxyrapamycin, demethylscytophycin, dermadin, desdamethine, dexylosyl-benanomycin, pseudoaglycone, dihydromocimycin, dihydronancimycin, diumycin, dnacin, dorrigocin, dynemycin, dynemycin triacetate, ecteinascidin, efrotomycin, endomycin, ensanchomycin, equisetin, ericamycin, esperamicin, ethylmonate, everninomicin, feldamycin, flambamycin, flavensomycin, florfenicol, fluvomycin, fosfomycin, fosfonochlorin, fredericamycin, frenolicin, fumagillin, fumifungin, funginon, fusacandin, fusafungin, gelbecidine, glidobactin, grahamimycin, granaticin, griseofulvin, griseoviridin, grisonomycin, hayumicin, hayumicin, hazymicin, hedamycin, heneicomycin, heptelicid acid, holomycin, humidin, isohematinic acid, karnatakin, kazusamycin, kristenin, L-dihydrophenylalanine, a L-isoleucyl-L-2-amino-4-(4'-amino-2', 5'-cyclohexadienyl) derivative, lanomycin, leinamycin, leptomycin, libanomycin, lincomycin, lomofungin, lysolipin, magnesidin, manumycin, melanomycin, methoxycarbonylmethylmonate, methoxycarbonylethylmonate, methoxycarbonylphenylmonate, methyl pseudomonate, methylmonate, microcin, mitomalcin, mocimycin, moenomycin, monoacetyl cladosporin, monomethyl cladosporin, mupirocin, mupirocin calcium, mycobacidin, myriocin, myxopyronin, pseudoaglycone, nanaomycin, nancimycin, nargenicin, neocarcinostatin, neoenactin, neothramycin, nifurtoinol, nocardicin, nogalamycin, novobiocin, octylmonate, olivomycin, orthosomycin, oudemansin, oxirapentyn, oxoglaucine methiodide, pactacin, pactamycin, papulacandin, paulomycin, phaeoramularia fungicide, phenelfamycin, phenyl, cerulenin, phenylmonate, pholipomycin, pirlimycin, pleuromutilin, a polylactone derivative, polynitroxin, polyoxin, porfiromycin, pradimicin, prenomycin, Prop-2-enylmonate, protomycin, *Pseudomonas* antibiotic, pseudomonic acid, purpuromycin, pyrinodemin, pyrrolnitrin, pyrrolomycin, amino, chloro pentenedioic acid, rapamycin, rebeccamycin, resistomycin, reuterin, reveromycin, rhizocticin, roridin, rubiflavin, naphthyridinomycin, saframycin, saphenamycin, sarkomycin, sarkomycin, sclopularin, selenomycin, siccanin, spartanamicin, spectinomycin, spongistatin, stravidin, streptolydigin, *streptomyces arenae* antibiotic complex, streptonigrin, streptothricins, streptovitacin, streptozotocine, a strobilurin derivative, stubomycin, sulfamethoxazol-trimethoprim, sakamycin, tejeramycin, terpentecin, tetrocarcin, thermorubin, thermozymocidin, thiamphenicol, thioaurin, thiolutin, thiomarinol, thiomarinol, tirandamycin, tolytoxin, trichodermin, trienomycin, trimethoprim, trioxacarcin, tyrissamycin, umbrinomycin, unphenelfamycin, urauchimycin, usnic acid, uredolysin, variotin, vermisporin, verrucarin, metronidazole, erythromycin and analogs, salts and derivatives thereof.

According to some preferred embodiments, the antibiotic agent is a tetracycline. The tetracycline may be selected from minocycline and doxycycline.

There is thus provided according to some further embodiments of the present disclosure, a foamable pharmaceutical carrier for external administration of an unstable active agent, the carrier including:
10% to 80% by weight of at least one unstable active agent-compatible (UAAC) solvent, selected from the group consisting of an oily emollient, a higher alcohol, a polyol and a polyol alkyl ether;
10% to 60% by weight of at least one unstable active agent-compatible (UAAC) hydrophobic solvent;
0.01% to 6% by weight of at least one surface-active agent; and
3% to 25% by weight of a liquefied or compressed gas propellant.

There is thus provided according to some additional embodiments of the present disclosure, a foamable pharmaceutical composition for external administration of an unstable active agent, the composition including:
10% to 80% by weight of at least one unstable active agent-compatible (UAAC) solvent, selected from the group consisting of an oily emollient, a higher alcohol, a polyol and a polyol alkyl ether;
10% to 60% by weight of at least one unstable active agent-compatible (UAAC) hydrophobic solvent;
0.01% to 5% by weight of at least one surface-active agent;
0% to 5% by weight of at least one polymeric agent; and
at least one unstable active agent.

In some cases, the foamable pharmaceutical composition includes 3% to 25% by weight of a liquefied or compressed gas propellant.

According to some further embodiments, the at least one unstable active agent includes an antibiotic agent.

Preferably, the disclosed pharmaceutical composition disclosure has the following property: a foam quality of at least good up to excellent; and at least one other property selected from: specific gravity in the range of about 0.02 gr/mL to about 0.5 gr/mL; a foam texture of a very fine creamy foam consistency to a fine bubble structure consistency; a sustainability of more than 95% for at least one minute upon release thereof to a surface from an aerosol can; less than 20% sedimentation following ten minutes of centrifugation at 3000 g; and compatibility with the at least one unstable active agent, wherein the compatibility is defined as less than 20% oxidation of the at least one unstable active agent after 72 hours.

In some cases, the foamable pharmaceutical composition has at least four of the properties. In some other cases, the composition has all of the properties.

There is thus provided according to some additional embodiments of the present disclosure, a method for producing a foamable pharmaceutical carrier suitable for external administration of an unstable active agent, the method including:
testing compatibility of at least one solvent and the unstable active agent so as to determine at least one unstable active agent-compatible (UAAC) solvent; and
formulating the foamable pharmaceutical carrier from the at least one unstable active agent-compatible (UAAC) solvent.

In some cases, the testing step includes determining whether the unstable active agent is at least partially oxidized in the at least one solvent within 72 hours.

There is thus provided, a method for producing a pharmaceutical composition for external administration of an unstable active agent, the method including:
testing compatibility of at least one solvent and the unstable active agent so as to determine at least one unstable active agent-compatible (UAAC) solvent; and
formulating the pharmaceutical composition from the at least one unstable active agent-compatible (UAAC) solvent and the unstable active agent.

In some cases the unstable active agent is an anti-infective agent. The anti-infective agent may be selected from the group consisting of an antibiotic agent, an antibacterial agent, an antifungal agent, an agent that controls yeast, an antiviral agent and an antiparasitic agent.

The pharmaceutical composition may sometimes include a combination of at least two active agents, or sometimes three agents.

There is thus provided, a method of treating a disorder of mammalian subject, including administering to the subject a pharmaceutically effective amount of the foamable pharmaceutical composition as described herein.

In some cases, the administering includes providing the composition to a target site. The target site may be selected from the group consisting of the skin, a body cavity, a mucosal surface, the nose, the mouth, the eye, the ear canal, the respiratory system, the vagina and the rectum.

The disorder may be selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo, chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating the disorder.

According to some embodiments, the active agent is selected from the group consisting of alclometasone dipropionate, amcinafel, amcinafide, amcinonide, beclomethasone, beclomethasone dipropionate, betamethsone, betamethasone benzoate, betamethasone dexamethasone-phosphate, dipropionate, betamethasone valerate, budesonide, chloroprednisone, chlorprednisone acetate, clescinolone, clobetasol, clobetasol propionate, clobetasol valerate, clobetasone, clobetasone butyrate, clocortelone, cortisone, cortodoxone, craposone butyrate, desonide, desoxymethasone, dexamethasone, desoxycorticosterone acetate, dichlorisone, diflorasone diacetate, diflucortolone valerate, difluorosone diacetate, diflurprednate, fluadrenolone, flucetonide, flucloronide, fluclorolone acetonide, flucortine butylesters, fludroxycortide, fludrocortisone, flumethasone, flumethasone pivalate, flumethasone pivalate, flunisolide, fluocinolone, fluocinolone acetonide, fluocinonide, fluocortin butyl, fluocortolone, fluorometholone, fluosinolone acetonide, fluperolone, fluprednidene acetate, fluprednisolone hydrocortamate, fluradrenolone, fluradrenolone acetonide, flurandrenolone, fluticasone, halcinonide, halobetasol, hydrocortisone, hydrocortisone acetate, hydrocortisone butyrate, hydrocortisone cyclopentylpropionate, hydrocortisone valerate, hydroxytriamcinolone, medrysone, meprednisone, .alpha.-methyl dexamethasone, methylprednisolone, methylprednisolone acetate, mometasone furoate, paramethasone, prednisolone, prednisone, pregnenolone, progesterone, spironolactone, triamcinolone, triamcinolone acetonide and derivatives, esters and salts thereof.

According to some further embodiments, the foamable pharmaceutical composition may include, by weight:
10-20% PPG-15 stearyl ether;
10-15% octyldodecanol;
40-70% light mineral oil;
1-5% cyclomethicone;
4-8% glyceryl monostearate;
4-8% stearyl alcohol; and
1-5% myristyl alcohol.

According to some further embodiments, the foamable pharmaceutical composition may include by weight 15% PPG-15 stearyl ether, 12% octyldodecanol, 54.46% light mineral oil, 3% cyclomethicone, 6% glyceryl monostearate, 6% stearyl alcohol, 2.5% myristyl alcohol, and 1.04% doxycycline monohydrate.

In some case, the foamable pharmaceutical composition further includes 3% to 25% by weight of a liquefied or compressed gas propellant.

According to some further embodiments, the foamable pharmaceutical composition includes, by weight:
10-20% PPG-15 stearyl ether;
10-15% octyldodecanol;
40-70% light mineral oil;
2-10% Sepigel 305;
1-5% cyclomethicone;
4-8% glyceryl monostearate;
4-8% stearyl alcohol; and
1-5% myristyl alcohol.

In some cases, the foamable pharmaceutical composition further includes 1-2% minocycline hydrochloride.

According to some additional embodiments, the foamable pharmaceutical composition includes, by weight about 15% PPG-15 stearyl ether, 12% octyldodecanol, 50.5% light mineral oil, 3% cyclomethicone, 6% glyceryl monostearate, 5% Sepigel 305, 6% stearyl alcohol, and 2.5% myristyl alcohol.

According to yet some further embodiments, the foamable pharmaceutical composition includes by weight about 15% PPG-15 stearyl ether; 12% octyldodecanol; 50.5% light mineral oil; 3% cyclomethicone; 6% glyceryl monostearate; 5% Sepigel 305; and 8.0% of Corn starch Derivative Aluminum free (DRY-FLO® AF).

According to some further embodiments, the foamable pharmaceutical composition includes by weight about 15% PPG-15 stearyl ether, 12% octyldodecanol, 49.33% light mineral oil, 3% cyclomethicone, 6% glyceryl monostearate, 3% Sepigel 305, 2.5% Myristyl alcohol and 8.0% of Corn starch Derivative Aluminum free (DRY-FLO® AF).

According to some further embodiments, the foamable pharmaceutical composition includes by weight about 42.21% PPG-15 stearyl ether, 42.21% light mineral oil, 6% glyceryl monostearate, and 2.5% cocoglycerides.

According to some further embodiments, the foamable pharmaceutical composition including, by weight about 42.21% PPG-15 stearyl ether; 42.21% light mineral oil; and 6% glyceryl monostearate.

There is thus provided according to some additional embodiments of the present disclosure, a foamable pharmaceutical composition for external administration of an unstable active agent, including:
at least one least one unstable active agent-compatible (UAAC) solvent, is selected from the group consisting of an emollient, an oil and a foam adjuvant; and
at least one surfactant.

According to yet some further embodiments, the unstable agent is doxycycline.

According to some further embodiments, the emollient is selected from cyclomethicone, isopropyl myristate, PPG-15 stearyl ether, propylene glycol, octyldodecanol, glycerol, diisopropyl adipate, and diisopropyl adipate.

According to yet some further embodiments, the foam adjuvant is selected from Oleyl alcohol, Stearic acid, Stearyl alcohol, Myristyl alcohol and Cocoglycerides.

According to some further embodiments, the oil is selected from light mineral oil and MCT oil.

According to yet some further embodiments, the surfactant is selected from Glycerol monostearate, Sucrose Ester HLB 11, GMS-PEG 100 Stearate, Polysorbate 80, Polysorbate 60, Polysorbate 20, Sorbitan monostearate, Methy Glucose Sesquistearate, PEG 40 Stearate (Myrj 52), PEG 100 Stearate (Myrj 59), Hydrogenated Castor Oil, Steareth-2, Steareth-20, Steareth-21 and Poloxamer 407 (20% gel).

A foamable pharmaceutical composition, wherein the unstable agent is minocycline.

According to yet some further embodiments, the emollient is selected from cyclomethicone; isopropyl myristate, PPG-15 stearyl ether; octyldodecanol; Isohexadecanol, diisopropyl adipate; and Cetearyl Octanoate.

According to yet some further embodiments, the foam adjuvant is selected from Oleyl alcohol, Stearyl alcohol, Myristyl alcohol and Cocoglycerides.

According to yet some further embodiments, the foamable pharmaceutical composition the oil is selected from hydrogenated castor oil and MCT oil.

According to yet some further embodiments, the surfactant is selected from Glycerol monostearate, Polysorbate 80, Polysorbate 60, Sucrose distearate, Polyoxyl 20 Stearyl Ether, Polyoxyl 2 Stearyl Ether, Sorbitan monostearate, Ester HLB 11, GMS-PEG 100 Stearate, Polysorbate 80, Polysorbate 60, Sorbitan monostearate (Span 60), Methy Glucose Sesquistearate, PEG 40 Stearate (Myrj 52), PEG 100 Stearate (Myrj 59), Montanov S, Glyceryl monostearate, and Sepigel 305.

In one or more embodiment, the foregoing formulations including an oily carrier are used with a tetracycline antibiotic such as doxycycline or minocycline for the treatment of acne. The use of an oil-based formulation for the treatment of acne runs counter to conventional approach, which avoid oily bases as exacerbating the underlying acne condition. In contrast, the current formulations moisturize and protect the skin. Initial investigations show that waterless hydrophobic preparations have a good "skin feel," are quickly absorbed and are not tacky.

The present disclosure relates to a foamable pharmaceutical carrier suitable for external administration of an unstable active agent. Carrier pharmaceutical compositions comprising the carriers, methods for production thereof and methods of treatment using these carriers and compositions are described.

According to one or more embodiments of the present disclosure, the foamable carrier, includes:
a) about 10% to about 80% by weight of at least one unstable active agent-compatible (UAAC) solvent selected from the group consisting of an oily emollient, a hydrophobic solvent, a higher alcohol, a foam adjuvant, a polyol and a polyol alkyl ether; and
b) at least one surface-active agent;

All % values are provided on a weight (w/w) basis.

Upon release from an aerosol container, the foamable carrier forms an expanded foam suitable for administration to the skin, a body surface, a body cavity or a mucosal surface. The carrier is suitable for being formulated in a pharmaceutical composition with at least one active agent. In some cases, the at least one active agent comprises at least one unstable active agent.

The term "unstable active agent" means herein, an active agent which is oxidized and/or degraded within less than a day, and in some cases, in less than an hour upon exposure to air, light, skin or water under ambient conditions.

A moiety or phase such as, but not limited to, a molecule and liquid respectively, is deemed herein to be "unstable active agent-compatible (UAAC)" when, upon contact of the unstable active agent with the moiety or phase, the agent does not significantly (e.g., more than 20%) oxidize or degrade at room temperature and pressure (RTP) after one week, preferably three weeks time under ambient conditions.

Alternatively, a moiety or phase such as, but not limited to, a molecule and liquid respectively, is deemed herein to be "unstable active agent-compatible (UAAC)" when, upon contact of the unstable active agent with moiety or phase, the agent does not significantly (e.g., preferably more than 5%) oxidize or degrade after one day preferably one weeks time under ambient conditions.

The identification of a "solvent", as used herein, is not intended to characterize the solubilization capabilities of the solvent for any specific active agent or any other component of the foamable composition. Rather, such information is provided to aid in the identification of materials suitable for use as a part in the foamable compositions described herein. Polypropylene Glycol (PPG) Alkyl Ethers In the context of the present disclosure, a polypropylene glycol alkyl ether (PPG alkyl ether) is a liquid, water-insoluble propoxylated fatty alcohol, having the molecular formula of $RO(CH_2CHOCH_3)_n$; wherein "R" is a straight-chained or branched $C_4$ to $C_{22}$ alkyl group; and "n" is in the range between 4 and about 50.

(PPG alkyl ethers), are organic liquids that function as skin-conditioning agent in pharmaceutical and cosmetic formulations. They possess exceptional emollient effect, side by side with enhanced solvency properties, which facilitates solubilization of active agents in a composition comprising a PPG alkyl ether. PPG alkyl ethers offer the following advantages when used as a component in the foamable composition of the present disclosure:

Due to the polypropylene glycol moiety, PPG alkyl ethers possess certain surface active properties and they assist in the coupling of polar and non-polar oils in an emulsion formulation;

PPG alkyl ethers are non-occlusive; offering a long-lasting and velvety feel;

They are chemically stable at extreme pH conditions;

Excellent solvency properties, particularly with difficult to formulate active agents;

When combined with certain surfactants, such as Brij 72 and Brij 721, PPG alkyl ethers form oleosomes and/or liquid crystal structures, which provide long lasting moisturization, excellent spreading as well as prolonged hydration properties.

Exemplary PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-50 oleyl ether, PPG-11 stearyl ether. Preferred PPG alky ethers according to the present disclosure include PPG-15 stearyl ether (also known as Earlamol E®, Unichema), PPG-2 butyl ether, PPG-9-13 butyl ether and PPG-40 butyl ether. PPG alkyl ethers can be incorporated in the foamable composition of the present disclosure in a concentration between about 1% and about 90%, preferably above 5%, above 10%, above 20%, above 30% and up to 60% PPG. More preferably between about 10% to about 20%.

PPG Stearyl Ethers

PPG stearyl ethers function as skin-conditioning and penetration agents in cosmetic formulations.

Polypropylene glycol stearyl ether 15, also known as polyoxypropylene 15 stearyl ether or as "PPG-15", and having a CAS Registry No. of [25231-21-4], is a stearyl ether having about 15 propylene oxide units incorporated in its structure. PPG-15 stearyl ether is a clear liquid, soluble in mineral oil, isopropyl ethers, cottonseed oil, ethanol, isopropanol and hexadecyl alcohol, to name a few, and is particularly useful as a solvent of difficult to formulate ingredients, such as sunscreens, aluminum chlorhydrate salts and skin toners. It is insoluble in water, propylene glycol and glycerin. PPG-15 stearyl ether is an inert and highly stable compound.

PPG stearyl ether also functions as a coupling agent, allowing, for example, the compatibility of polar and non polar oils with ethanol and perfumes in after shave lotions. It is chemically stable at extreme pH levels and at the same time saturated, providing excellent shelf life stability.

Higher (Fatty) Alcohols

In some embodiments of the present disclosure, the compositions and carriers comprise one or more higher alcohols. These generally exclude "lower alcohols". The fatty alcohols are typically liquid at ambient temperature.

Fatty alcohols may defined as follows:

The fatty alcohols hereof have a melting point of 30° C. or less, preferably about 25° C. or less, more preferably about 22° C. or less.

The unsaturated fatty alcohols hereof are also nonvolatile. By nonvolatile what is meant is they have a boiling point at 1.0 atmospheres of at least about 260° C., preferably at least about 275° C., more preferably at least about 300° C.

Suitable fatty alcohols include unsaturated monohydric straight chain fatty alcohols, saturated branched chain fatty alcohols, saturated C8-C12 straight chain fatty alcohols, and mixtures thereof. The unsaturated straight chain fatty alcohols will typically have one degree of unsaturation. Di- and tri-unsaturated alkenyl chains may be present at low levels, preferably less than about 5% by total weight of the unsaturated straight chain fatty alcohol, more preferably less than about 2%, most preferably less than about 1%.

Preferably, the unsaturated straight chain fatty alcohols will have an aliphatic chain size of from C12-C22, more preferably from C12-C18, most preferably from C16-C18. Especially preferred alcohols of this type include oleyl alcohol and palmitoleic alcohol.

The branched chain alcohols will typically have aliphatic chain sizes of from C12-C22, preferably C14-C20, more preferably C16-C18. Exemplary branched chain alcohols for use herein include isostearyl alcohol, octyl dodecanol, and octyl decanol. Examples of saturated C8-C12 straight chain alcohols include octyl alcohol, caprylic alcohol, decyl alcohol, and lauryl alcohol. Furthermore, the higher alcohols may be selected from straight chain fatty alcohols, having 6 or more carbon atoms, which are liquid at ambient temperature, such as, but not limited to Hexanol, Octanol, Nonanol, Decanol; branched alcohols, such as: 2 Octanol (Capryl Alcohol), Undecanol (Undecyl Alcohol), 2 Butyl Octanol (Isolauryl Alcohol), Tridecyl Alcohol (Isotridecyl Alcohol), 2 Butyl Decanol, 2 Hexyl Octanol, Isomyristyl Alcohol, 2 Hexyl Decanol, Isocetyl Alcohol, 2 Octyl Decanol, 2 Hexyl Dodecanol, Isostearyl Alcohol, Isooctadecanol, Isooleyl Alcohol (unsaturated and branched), Isoarachidyl Alcohol, 2 Decyl Tetradecanol, Isolignoceryl Alcohol, 2 Decyl Tetradecanol, 2 Tetradecyl Octadecanol, 2 Tetradecyl Eicosanol, 2 Hexadecyl Octadecanol, 2 Hexadecyl Eicosanol; additionally unsaturated alcohols, such as Erucyl Alcohol, Linoleyl Alcohol, oleyl alcohol may be employed.

Polymeric Agent

The composition of the present disclosure contains a polymeric agent. It has been documented that the presence of a polymeric agent is necessary for the creation of foam, having fine bubble structure, which does not readily collapse upon release from the pressurized aerosol can. The polymeric agent serves to stabilize the foam composition and to control drug residence in the target organ. Preferably, the polymeric agent is soluble or readily dispersible in the polyol; or in the mixture of a polyol and an additional solvent.

Non-limiting examples of polymeric agents that are soluble or readily dispersible in propylene glycol are Hydroxypropylcellulose and carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981.

Other polymeric agents are suitable for use according to the present disclosure provided that they are soluble or readily dispersible in the polyol; or in the mixture of a polyol and an additional solvent, on a case by case basis.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses. Polyethylene glycol, having molecular weight of 1000 or more (e.g., PEG 1,000, PEG 4,000, PEG 6,000 and PEG 10,000) also have gelling capacity and while they are considered herein as "secondary solvents", as detailed herein, they are also considered polymeric agents.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface-Active Agents

The composition further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants can be significant in producing breakable forms of good quality. It has been further discovered that the generally thought considerations for HLB values for selecting a surfactant or surfactant combination are not always binding for emulsions and moreover for waterless and substantially non aqueous carriers the usual guidelines are less applicable. For oil based waterless systems HLB values may have little significance other than to indicate the proportion of an ampiphilic molecule that is hydrophobic and therefore potentially more at home in an oil single phase environment. Surfactants can play a significant role in foam formation where the foamable formulation is a single phase composition.

In selecting a suitable surfactant or surfactant combination for use in the substantially single phase formulations described herein selection relates to a multiple of factors including but not limited to solubility and miscibility in the liquid oil and in the silicone to produce substantially a single phase; the ability to form foam of quality; the ability to stabilize the extruded foam; a HLB value which preferably suggests potential compatibility with the liquid oil and the silicone; and solubility of surfactant in the formulation.

In certain embodiments the surfactant can have thickening properties. In certain embodiments the surfactant can effect the viscosity of the pre foam formulation (PFF). In certain other embodiments the surfactant has little or no effect. The concentration of the surfactant agent in combination with the oil and silicone and other ingredients should be selected so that the composition, after filling into aerosol canisters, is flowable, and can be shaken in the canister. In one or more embodiments, the concentration of the surfactant agent is selected such that the viscosity of the composition, prior to filling of the composition into aerosol canisters, is less than 13,000 CPs, and more preferably, less than 10,000 CPs, preferably below about 9000, more preferably below about 6000 cps. In one or more embodiments average bubble size of the resultant foam should be below about 200 microns, preferably below 150 and more preferably below 100 microns; In one or more embodiments foam density is below about 0.2 preferably below about 0.1 g/ml. In one or more embodiments hardness of the resultant foam is in the range of about 5 to about 35.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, (preferably about 7 to about 12) or more than one surface active agent and the weighted average of their HLB values is between about 7 and about 14 (preferably about 7 to about 12).

According to one or more other embodiments the composition contains a single surface active agent having an HLB value between about 9 and about 19, or more than one surface active agent and the weighted average of their HLB values is between about 9 and about 19.

In a waterless or substantially waterless environment a wide range of HLB values may be suitable. In one or more embodiments the HLB may not play a role in a single phase system Preferably, the composition contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a fatty acid ester of glycerol, a mono, di or triglyceride of stearic acid, a mono, di or triglyceride of palmitic acid, a diglyceride, isoceteth-20 and mono-, di- and tri-esters of sucrose with fatty acids. In certain embodiments, suitable sucrose esters include those having high monoester content, which have higher HLB values. However, sorbitan esters are not used alone as primary surfactants. In an embodiment if present sorbitan esters are used in combination with one or more primary surfactants and functions as a secondary or co-surfactant.

In one or more embodiments the surfactant is selected to produce a foam of quality being of least of about good quality foam and preferably of excellent quality foam. In one or more embodiments the surfactant includes, a fatty acid ester of glycerol, such as a mono, di or tri fatty ester of stearic acid or palmitic acid or arachidic acid or beheneic acid. In one or more embodiments the surfactant is used on its own with the oil. In certain other embodiments the surfactant is used in combination with one or more other surfactants, such as, those listed below. In an embodiment the combination is, for example, glycerol monostearate and PEG 100 stearate. Other similar combinations are readily envisaged.

Glycerol Fatty Acid Esters

| Ester | Function | Solubility | Fatty acid (main) | Comments |
|---|---|---|---|---|
| Glyceryl Behenate | Thickener, lubricant | Practically insoluble in oil and water | Beheneic (C22) | Not tested |
| Glyceryl monooleate | Non ionic Sufactant | Soluble in oil and practically | Oleic (double bond in side | Fairly Good Foam with |

-continued

| Ester | Function | Solubility | Fatty acid (main) | Comments |
|---|---|---|---|---|
| | | insoluble in water | chain (C18) | mineral oil and silicone |
| Glyceryl monostearate (GMS) | Non ionic emulsifying agent | Soluble in mineral oil and practically insoluble in water | Stearic (C18) | Good - Excellent Foam with mineral oil and silicone oil even though GMS and other fatty acid monoesters are not efficient emulsifiers. |
| Glyceryl Palmitostearate | Sustained release, lubricant | Practically insoluble in mineral oil and water | Mixture of mono (~<17%), di, and triglycerides of C16 and C18 fatty acids | Excellent Foam with mineral oil and silicone oil even though GMS and other fatty acid monoesters are not efficient emulsifiers |

In an embodiment the surfactant is an ether for example polyoxyethylene (26) glycerol ether.

In certain embodiments, surfactants are selected which can provide a close packed surfactant layer. To achieve such objectives combinations of at least two surfactants are selected. Preferably, they should be complex emulgators and more preferably they should both be of a similar molecular type; for example, a pair of ethers, like steareth 2 and steareth 21, or a pair of esters, for example, PEG-40 stearate and polysorbate 80. Ideally, the surfactants can be ethers. In certain circumstances POE esters cannot be used and a combination of sorbitan laurate and sorbitan stearate or a combination of sucrose stearic acid ester mixtures and sodium laurate may be used. All these combinations due to their versatility and strength may also be used satisfactorily and effectively with ether formulations, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenyl-succinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
|---|---|
| steareth 2 | ~4.9 |
| glyceryl monostearate/PEG 100 stearate | Av ~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

Another component of the formulations of the present disclosure is Sepigel 305. Sepigel 305 comprises Polyacrylamide and C13-14 Isoparaffin and Laureth-7. It acts as a surfactant and as a thickening and emulsifying agent, and comes in a liquid, very easy to handle form. It requires neither premixing, nor high rate of shear nor neutralisation. Sepigel 305 can be used to emulsify all types of oil phase without heating, producing gel-cream with a rich, silky texture that are easy to apply and rapidly absorbed by the skin.

More exemplary stabilizing surfactants which may be suitable for use in the present disclosure are found below.

PEG-Fatty Acid Monoester Surfactants, such as:

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants, such as:

| Chemical name | Product example name | HLB |
|---|---|---|
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 | distearate Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 distearate | Cithrol 4DS series (Croda) | >10 |
| PEG-20 glyceryl oleate | Tagat .RTM. O (Goldschmidt) | >10 |

Transesterification Products of Oils and Alcohols, such as:

| Chemical name | Product example name | HLB |
|---|---|---|
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
|---|---|---|
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters, such as:

| Chemical name | Product example name | HLB |
|---|---|---|
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers, such as:

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants, such as:

| Chemical name | Product example name | HLB |
|---|---|---|
| Sucrose distearate | Sisterna SP50, Surfope 1811 | 11 |

Sorbitan Fatty Acid Ester Surfactants, such as:

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable formulation or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TR1 or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain other embodiments the surfactant is a combination of span 60 and GMS. In certain other embodiments the surfactant is a combination of two or all of PEG 40 stearate, sorbitan stearate and polysorbate 60

In certain other embodiments the surfactant is one or more of sucrose stearic acid esters, sorbitan laureth, and sorbitan stearate.

Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the formulation.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid. Moreover for the purposes of formulating with liquid ethers a liquid surfactant is preferred In one or more embodiments the liquid surfactant is a polysorbate, preferably polysorbate 80 or 60.

In one or more embodiments the at least one surface active agent is solid, semi solid or waxy. In a further embodiment they are soluble in oil and in another embodiment have a HLB of less than about 12.

It should be noted that HLB values may not be so applicable to non ionic surfactants, for example, with liquid crystals or with silicones. Also HLB values may be of lesser significance in a waterless or substantially non-aqueous environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier. In a preferred embodiment at least one surfactant is a liquid.

In one or more embodiments, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions of the present disclosure.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1

In one or more embodiments, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

For foams in selecting a suitable surfactant or combination thereof it should be borne in mind that the upper amount of surfactant that may be used may be limited by the shakability of the composition. If the surfactant is non liquid, it can make the formulation to viscous or solid. Subject to its miscibily solid surfactants may be added first, and may require gentle warming and then cooling before being combined with the other ingredients. In general terms, as the amount of non-liquid surfactant is increased the shakability of the formulation reduces until a limitation point is reached where the formulation can become non shakable and unsuitable. Thus in one embodiment, any effective amount of surfactant may be used provided the formulation remains shakable. In other certain limited embodiments the upper limit for foamable formulations may be determined by flowability such that any effective amount can be used provided the formulation is sufficiently flowable to be able to flow through an actuator valve and be released and still expand to form a good quality foam. This may be due without being bound by any theory to one or more of a number of factors such as the viscosity, the softness, the lack of crystals, the pseudoplastic or semi pseudo plastic nature of the composition and the dissolution of the propellant into the composition.

In certain embodiments the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiments the concentration of surface active agent is between about 1% and about 6% or between about 1% and about 4%.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside.

In one or more embodiments, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher HLB values.

In one or more preferred embodiments of the present disclosure the surfactant includes at least one surfactant selected from a polyoxyethylene fatty ether, a polyoxyethylene fatty ester, a carbohydrate ester and a sucrose ester.

In one or more embodiments non limiting examples of non-ionic surfactants include steareth-2, steareth-20, steareth-21, ceteareth 2, PEG-100 stearyl ether, cetearyl glucoside, Methy Glucose Sesquistearate, sorbitan monostearate, GMS NE and span 20.

In one or more embodiments non limiting other examples of surfactant combinations are glyceryl stearate and PEG 100 stearate and laureth4; steareth 2, PEG 100 searate and laureth4; and cetearyl glucoside and cetearyl alcohol.

In an embodiment the surfactant containing formulations are further boosted by a foam adjuvant for example stearyl alcohol.

A non limiting example of a combination of surfactants having a weighted average of their HLB values of 11 is Glyceryl Stearate and PEG-100 Stearate (for example trade name "simulsol 165" from Sepic).

Solid Matter Agents

According to an embodiment of the present disclosure, the at least one active agent comprises solid matter or particulate matter i.e., material that is not soluble in the liquid carrier composition of the foamable composition. For definition purposes, solid matter shall mean material that is not soluble in the foamable composition more than 10% of the concentration intended to be included in said foamable composition. The concentration of the solid matter in the foamable composition is from about 0% to about 20% w/w. In one or more embodiments, the concentration of solid matter in the composition is from about 2% to about 16% w/w.

By way of non-limiting examples, the following classes of solid matter substances are presented:

Metallic oxides, such as titanium dioxide, zinc oxide, zirconium oxide, iron oxide. Preferably, as used in the present disclosure, titanium dioxide has an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. In one embodiment the metal oxides are present in the amount of from about 0.1% to about 20%, preferably from about 0.5% to about 16%, more preferably from about 1% to about 10%, of the composition. In yet another embodiment, such solids are micronized to form particles having primary size of less than 15 nm.

Silicon containing solid matter includes silicone oxide, also termed "silica", "fumed silica" and "silica gel", a white or colorless insoluble solid (SiO2); and talc, which is fine grained mineral consisting of hydrated magnesium silicate;

Carbon, for example in the form of amorphous carbon or graphite;

Oxidizing agents, such as benzoyl peroxide, calcium and magnesium hypochlorite;

Metallic Silver, in small particles, including nanocrystalline silver, which is used for antibacterial and wound healing purposes; other metal particles and mineral particles;

cosmetic scrub materials, including, for example meals of strawberry seeds, raspberry seeds, apricot seeds, sweet almond, cranberry seeds; and pigments, which are insoluble in the foamable composition.

Hydrophobic Solvent

Optionally, the foamable carrier further contains at least one hydrophobic solvent. The identification of a "hydrophobic solvent", as used herein, is not intended to characterize the solubilization capabilities of the solvent for any specific active agent or any other component of the foamable composition. Rather, such information is provided to aid in the identification of materials suitable for use as a part in the foamable compositions described herein.

A "hydrophobic solvent" as used herein refers to a material having solubility in distilled water at ambient temperature of less than about 1 gm per 100 mL, more preferable less than about 0.5 gm per 100 mL, and most preferably less than about 0.1 gm per 100 mL.

In one or more embodiments, the hydrophobic organic carrier is an oil, such as mineral oil, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils; essential oils; and silicone oils, such as cyclomethicone, polyalkyl siloxanes, polyaryl siloxanes, polyalkylaryl siloxanes and polyether siloxane copolymers, and poly(dimethylsiloxane)-(diphenyl-siloxane) copolymers.

One class of hydrophobic solvents includes polyunsaturated oils, containing omega-3 and omega-6 fatty acids, which are know to possess therapeutic properties through different modes of action. Examples of such polyunsaturated fatty acids are linoleic and linolenic acid, gamma-linoleic acid (GLA), eicosapentaenoic acid (EPA) and docosahexaenoic acid (DHA). Thus, in one preferred embodiment of the present disclosure the at least one hydrophobic solvent comprises at least 6% of an oil selected from omega-3 oil, omega-6 oil, and mixtures thereof.

Another preferred class of hydrophobic solvents comprises the essential oils, which are considered "therapeutic oils", which contain active biologically occurring molecules and, upon topical application, exert a therapeutic effect. Examples of such oils are rosehip oil, which contain retinoids and is known to reduce acne and post-acne scars, tea tree oil, which possesses anti-microbial activity including antibacterial, antifungal and antiviral properties. Other examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla, verbena, as well as any other therapeutically beneficial oil known in the art of herbal medication.

Emollients

A further preferred class of solvents are "emollients" that have a softening, refatting, or soothing effect, especially when applied to body areas, such as the skin and mucosal surfaces. Emollients are not necessarily hydrophobic. Without derogating the generality of this definition, examples of suitable emollients for use include but are not limited to mineral oil, lanolin oil, coconut oil, cocoa butter, olive oil, aloe vera extract, jojoba oil, castor oil, fatty acids, fatty alcohols, diisopropyl adipate, hydroxybenzoate esters, benzoic acid esters of C9 to C15 alcohols, isononyl iso-nonanoate, isopropyl myristate, silicone oils, polyethers, C12 to C15 alkyl benzoates, oleic acid, stearic fatty acid, cetyl alcohols, hexadecyl alcohol, dimethyl polysiloxane, polyoxypropylene cetyl ether, polyoxypropylene butyl ether, hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and, and derivatives, esters, salts and mixtures thereof. Examples of other suitable emollients may be found in the Cosmetic Bench Reference, pp. 1.19-1.22 (1996) and in similar publications. In an embodiment of the present disclosure, the oily solvent component is an emollient.

In some embodiments, the emollients used in the present disclosure are oily emollients. Non-limiting examples of oily emollients include Cetearyl Octanoate, Cyclomethicone, PPG-15 Stearyl Ether, Propylene glycol, Octyldodecanol, Glycerol, Diisopropyl adipate, and isostearic acid.

Foam Adjuvant

Optionally, a foam adjuvant is included in the foamable carriers of the present disclosure to increase the foaming capacity of surfactants and/or to stabilize the foam. In one or more embodiments of the present disclosure, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition. In some embodiments, a foam adjuvant is a fatty alcohol having between 14 and 18 carbons in its carbon chain. In some embodiments, the foam adjuvant is oleyl alcohol, stearyl alcohol, or myristyl alcohol. In some embodiments, the foam adjuvant is cocoglycerides.

In one or more embodiments of the present disclosure, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

Polyol

In an embodiment of the present disclosure, the solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2, 56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present disclosure are mannitol, sorbitol, xylitol, maltitol, lactitol. (Maltitol and lactitol are not completely hydrogenated compounds—they are a monosaccharide combined with a polyhydric alcohol). Mixtures of polyols, including (1) at least one polyol selected from a diol and a triol; and (2) a saccharide are contemplated within the scope of the present disclosure.

Polyethylene Glycol

In an embodiment of the present disclosure, the solvent consists of a polymerized ethylene glycol, namely polyethylene glycol, which is also termed "PEG". Exemplary PEGs are provided in the following table.

| Composition | Av. Molecular weight | Appearance | Melting point (° C.) |
|---|---|---|---|
| PEG 200 | 190~210 | Oily liquid | ? |
| PEG 300 | 285~315 | Oily liquid | |
| PEG 400 | 380~420 | Oily liquid | ? |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present disclosure, the PEG is selected from the group consisting of PEG 200, PEG 300, PEG 400, PEG 600, PEG 1000, PEG 4000, PEG 6000 and PEG 8000. The foamable carrier according to the present disclosure can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site. The concentration of the PEG should be in a level that results in viscosity, prior to filling of the composition into aerosol canisters, of less than 12,000 CPs, and more preferably, less than 10,000 CPs.

Secondary Solvent

Optionally, a secondary solvent is added to the foamable composition of the present disclosure. The secondary solvent is selected from a variety of organic solvents that are typically miscible on both water and oil. Examples of solvent that can be contained in the foamable carrier of the present disclosure include dimethyl isosorbide, tetrahydrofurfuryl alcohol polyethyleneglycol ether (glycofurol), DMSO, pyrrolidones, (such as N-Methyl-2-pyrrolidone and 1-Methyl-2-pyrrolidinone), ethyl proxitol, dimethylacetamide (DMAc), PEG-type surfactants and alpha hydroxy acids, such as lactic acid and glycolic acid.

Solubilization and Penetration Enhancement

In many cases, polyols, PEGs and solvents possess a high solubilizing power and thus, they can enable increased concentrations of a pharmaceutical active agent. Polyols, PEGs and solvents are also known for their skin penetration enhancement properties. These properties enable high drug bioavailability in the target area of treatment, resulting in an enhanced therapeutic effect. Occasionally, combinations of a polyol, PEGs and a secondary solvent, exhibit an increased permeability across the skin, as suggested, for example, in Eur J Pharm Biopharm. 1998 November; 46(3):265-71.

Thus, in one or more embodiments, the foamable carrier contains (1) at least one solvent, selected from a polyol (selected from a diol and a triol) and PEG; and (2) at least one secondary solvent.

In one or more embodiments, the foamable carrier contains (1) a mixture of at least two polyols; and (2) at least one secondary solvent. In additional embodiments, the foamable carrier contains a mixture of at least one polyol and at least one PEG; yet in other embodiments the foamable carrier contains (1) a mixture of at least one polyol and at least one PEG and (2) at least one secondary solvent.

According to certain embodiments the ratio between the polyol and/or PEG and the secondary solvent is between 9:1 and 1:1.

In certain embodiments, the polyol is selected from the group consisting of propylene glycol, hexylene glycol and glycerin (and mixtures thereof); and the secondary solvent is selected from the group consisting of dimethyl isosorbide, diethylene glycol monoethyl ether, a liquid polyethylene glycol and glycofurol.

In certain embodiments, the foamable carrier contains (1) at least one polyol; and (2) dimethyl isosorbide.

Substantially Alcohol Free

Lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the composition is substantially alcohol-free i.e., free of short chain alcohols. In other embodiments, the composition comprises less than about 5% final concentration of lower alcohols, preferably less than 2%, more preferably less than 1%.

Skin Penetration Enhancer

A "skin penetration enhancer", also termed herein "penetration enhancer," is an organic solvent, typically soluble in both water and oil. Examples of penetration enhancer include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, hexylene glycol, other glycols, sulfoxides, such as dimethylsulfoxide (DMSO), dimethylformanide, methyl dodecyl sulfoxide, dimethylacetamide, dimethylisosorbide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the penetration enhancer is a polyethylene glycol (PEG) or PEG derivative that is liquid at ambient temperature.

Suitable skin penetration enhancers include but are not limited to acetone, acyl lactylates, acyl peptides, acylsarcosinates, alkanolamine salts of fatty acids, alkyl benzene sulphonates, alkyl ether sulphates, alkyl sulphates, anionic surface-active agents, benzyl benzoate, benzyl salicylate, butan-1,4-diol, butyl benzoate, butyl laurate, butyl myristate, butyl stearate, cationic surface-active agents, citric acid, cocoamidopropylbetaine, decyl methyl sulfoxide, decyl oleate, dibutyl azelate, dibutyl phthalate, dibenzyl sebacate, dibutyl sebacate, dibutyl suberate, dibutyl succinate, dicapryl adipate, didecyl phthalate, diethylene glycol, diethyl sebacate, diethyl-m-toluamide, di(2-hydroxypropyl)ether, diisopropyl adipate, diisopropyl sebacate, N,N-dimethyl acetamide, dimethyl azelate, N,N-dimethyl formamide, 1,5-dimethyl-2-pyrrolidone, dimethyl sebacate, dimethyl sulphoxide, dioctyl adipate, dioctyl azelate, dioctyl sebacate, 1,4 dioxane, 1-dodecylazacyloheptan-2-one, dodecyl dimethyl amine oxides, ethyl caprate, ethyl caproate, ethyl caprylate, 2-ethylhexyl pelargonate, ethyl-2-hydroxypropanoate, ethyl laurate, ethyl myristate, 1-ethyl-2-pyrrolidone, ethyl salicylate, hexyl laurate, 2-hydroxyoctanoic acid, 2-hydroxypropanoic acid, 2-hydroxypropionic acid, isethionates, isopropyl isostearate, isopropyl palmitate, guar hydroxypropyltrimonium chloride, hexan-2,5-diol, khellin, lamepons, lauryl alcohol, maypons, metal salts of fatty acids, methyl nicotinate, 2-methyl propan-2-ol, 1-methyl-2-pyrrolidone, 5-methyl-2-pyrrolidone, methyl taurides, miranol, nonionic surface-active agents, octyl alcohol, octylphenoxy polyethoxyethanol, oleic ethanolamide, pleyl alcohol, pentan-2,4-diol, phenoxyethanol, phosphatidyl choline, phosphine oxides, polyalkoxylated ether glycollates, poly(diallylpiperidinium chloride), poly (dipropyldiallylammonium chloride), polyglycerol esters, polyoxyethylene lauryl ether, polyoxy:polyoxyethylene stearate, polyoxypropylene 15 stearyl ether, poly(vinyl pyridinium chloride), propan-1-ol, propan-2-ol, propylene glycol dipelargonate, pyroglutamic acids, 2-pyrrolidone, pyruvic acids, Quaternium 5, Quaternium 18, Quaternium 19, Quaternium 23, Quaternium 31, Quaternium 40, Quaternium 57, quartenary amine salts, quaternised poly (dimethylaminoethylmethacryl-ate), quaternised poly (vinyl alcohol), sapamin hydrochloride, sodium cocaminopropionate, sodium dioctyl sulphonsuccinate, sodium laurate, sodium lauryl ether sulphate, sodium lauryl sulphate, sugar esters, sulphosuccinate, tetrahydrofuran, tetrahydrofurfural alcohol, transcutol, triethanolamine dodecyl benzene sulphonate, triethanolamine oleate, urea, water and derivatives, esters, salts and mixtures thereof.

Potent Solvent

In one or more embodiments of the present disclosure, the foamable composition includes a potent solvent, in addition to or in place of one of the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments of the present disclosure, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition of the present disclosure; or even more than about 60%.

Non-limiting examples of pairs of active agent and potent solvent include: Betamethasone valerate: Practically insoluble in mineral oil (<0.01%); soluble more than 1% in glycofurol; Hydrocortisone butyrate: Practically insoluble in mineral oil (<0.01%); soluble more than 1% in glycofurol; Metronidazole: Practically insoluble in mineral oil (<0.01%); soluble more than 1% in dimethyl isosrbide; Ketoconazole: Practically insoluble in mineral oil (<0.01%); soluble more than 1% in glycofurol, propylene glycol and dimethyl isosrbide; Mupirocin: Practically insoluble in mineral oil (<0.01%); soluble more than 1% in glycofurol, hexylene glycol, dimethyl isosorbide, propylene glycol and polyethylene glycol 400 (PEG 400); Meloxicam, a nonsteroidal anti-inflammatory agent: Practically insoluble in mineral oil (<0.001%); soluble in propylene glycol: 0.3 mg/mL; and in PEG 400: 3.7 mg/mL; and Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butaneediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

The use of a potent solvent in a foam composition provides an improved method of delivering poorly soluble therapeutic agents to a target area. It is known that low drug solubility results in poor bioavailability, leading to decreased effectiveness of treatment. Foam compositions of the present disclosure, for which the solvent includes a potent solvent, increase the levels of the active agent in solution and thus, provide high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams of the present disclosure, which are drip-free, provide a superior vehicle for such active agents, enabling convenient usage and accurate effective dosing.

In one or more embodiments of the present disclosure the present disclosure the foamable pharmaceutical composition may additionally include a mixture of two or more of the solvents selected from the group of hydrophobic solvents, silicone oils, emollients, polar solvents and potent solvents in an appropriate proportion as would be appreciated to a person skilled in the art.

In one or more embodiments of the present disclosure, the PPG alkyl ether may act as a potent solvent Modulating Agent The term modulating agent is used to describe an agent which can improve the stability of or stabilize a carrier or a foamable composition and or an active agent by modulating the effect of a substance or residue present in the carrier or composition. The substance or residue may for example be acidic or basic and potentially alter an artificial pH in a waterless or substantially non aqueous environment or it may be one or more metal ions which may act as a potential catalyst in a waterless or substantially non aqueous environment or it may be an ionisation agent or it may be an oxidizing agent.

In one or more other embodiments the modulating agent is used in a waterless composition. In one or more embodiments the modulating agent is used in a substantially non aqueous composition In one or more embodiments the modulating agent is used to describe an agent which can affect pH in an aqueous solution.

The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions.

In the embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of a waterless or substantially non aqueous carrier, composition, foamable carrier or foamable composition or resultant foam of the present disclosure.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the artificial pH in a waterless environment should be lower. In contrast, if one residue was acid and the other basic the net effect in the formulation may be significantly reduced. In some circumstances the active ingredient may favor an acidic pH or more significantly may need to be maintained at a certain acidic pH otherwise it may readily isomerize, chemically react or breakdown, in which case introducing acidic components might be of help. Likewise in some circumstances the active ingredient may favor a basic pH or more significantly may need to be maintained at a certain basic pH otherwise it may readily hydrolyse, undergo rearrangement, isomerize, chemically react or breakdown, in which case introducing basic components might be of help. In an embodiment of the present disclosure sufficient modulating agent is added to achieve an artificial pH in which the active agent is preferably stable. Such artificial pH may be acidic, may be basic or may be neutral.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present disclosure. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

A buffer, as defined by Van Slyke [Van Slyke, J. Biol. Chem. 52, 525 (1922)], is "a substance which by its presence in solution increases the amount of acid or alkali that must be added to cause unit change in pH".

A buffer solution is a solution of a definite pH made up in such a way that this pH alters only gradually with the addition of alkali or acid. Such a solution consists of a solution of a salt of the week acid in the presence of the three acid itself. The pH of the solution is determined by the dissociation equilibrium of the free acid.

An acid can be a strong acid or a weak acid. A strong acid is an acid, which is a virtually 100% ionized in solution. In contrast, a week acid is one which does not ionize fully when it is dissolved in water. The lower the value for pKa, the stronger is the acid and likewise, the higher the value for pKa the weaker is the acid.

A base can be a strong base or a weak base. A strong base is something, which is fully ionic with 100% hydroxide ions. In contrast, a weak base is one which does not convert fully into hydroxide ions in solution. The lower the value for pKb, the stronger is the base and likewise, the higher the value for pKb the weaker is the base.

In general terms, three factors, which influence the strength of a base, are firstly the ease with which the lone pair takes up a hydrogen ion; secondly, the stability of ions being formed and thirdly, the way they interact with water such that if they pick up hydrogen ion's more readily it is a stronger base.

In an embodiment of the present disclosure, the modulating or additional component is a pH adjusting agent or a buffering agent.

The modulating agent to the foamable composition of the present disclosure is useful for stabilizing pharmaceutical and cosmetic active agents which are unstable in certain pH conditions. It is known, for example, that active agents, which contain ester bond in their structure tend to undergo hydrolysis of the ester bond at basic pH levels. Therefore, the addition of an agent which avoids the formation of basic pH condition and thus, prevents degradation of such active agents. Many steroid compounds are known to undergo rearrangement at high pH, and again, adding an acidic modulating agent helps prevent such degradation. This is clearly exemplified by the stark difference in stability results for BMV in the absence and presence of a modulating agent as demonstrated in Examples 1 and 2 below. Another example of a pH-sensitive active agent is vitamin D, which degrades at low pH levels. In such a case, the addition of a basic modulating agent, such as triethanol amine is useful to maintain acceptable stability of this active agents as can be seen an exemplified in Example 5 below.

In certain cases, the stability of an active agent may be influenced by small quantities of, for example, metal ions in the waterless compositions. Such metal ions may act as a catalyst in facilitating the reaction or breakdown of the agent. Thus the modulating agent can be a chelating or sequestering or complexing agent on its own. In one or more embodiments of the present disclosure there is provided an effective amount of chelating agent which is sufficiently soluble or functional in the waterless solvent to enable it to "mop up" or "lock" metal ions.

For instance it is known that Polyphenols through the chelation of transition-metal ions, particularly those of iron and copper inhibit free radical formation and the propagation of free radical reactions (Brown et al. in Biochem. J. 330, 1173 1178 (1998)). Citric acid, amino acids, and thylenediaminetetraacetic acid also form chelates with metallic ions such as copper and iron, thus avoiding their catalytic action on the oxidation of lipids. Most of these chelating agents exhibit little or no antioxidant activity when used alone, and therefore they are considered as synergistic agents of other antioxidants. Thus, they increase, to a great extent, the action of primary antioxidants.

In one or more embodiments of the present disclosure the chelating agent is selected from the group consisting of acetyl trihexyl citrate, aminotrimethylene phosphonic acid, beta-alanine diacetic acid, bismuth citrate, calcium disodium edta, citric acid, cyclohexanediamine tetraacetic acid, diammonium citrate, dibutyl oxalate, diethyl oxalate, diisobutyl oxalate, diisopropyl oxalate, dilithium oxalate, dimethyl oxalate, dipotassium edta, dipotassium oxalate, dipropyl oxalate, disodium edta, disodium edta-copper, disodium pyrophosphate, edta, etidronic acid, hedta, methyl cyclodextrin, oxalic acid, pentapotassium, triphosphate, pentasodium aminotrimethylene phosphonate, pentasodium pentetate, pentasodium triphosphate, pentetic acid, phytic acid, potassium citrate, sodium citrate, sodium dihydroxyethylglycinate, sodium gluceptate, sodium gluconate, sodium hexametaphosphate, sodium metaphosphate, sodium metasilicate, sodium oxalate, sodium trimetaphosphate, tea-edta, tetrahydroxypropyl ethylenediamine, tetrapotassium etidronate, tetrapotassium pyrophosphate, tetrasodium edta, tetrasodium etidronate, tetrasodium pyrophosphate, tripotassium edta, trisodium edta, trisodium hedta, trisodium nta, trisodium phosphate, malic acid, fumaric acid, maltol, succimer, penicillamine, dimercaprol, and desferrioxamine mesilate.]

Other authorized chelating agents are listed pursuant to annex 1, paragraph E.3.1 of regulation (EC) No 2003 (See Directive 67/548/EEC OJ 196, 16.8 1967, p1) and are also incorporated herein by reference.

In one or more preferred embodiments of the present disclosure the chelating agent is selected from the group consisting of ethylenediaminetetraacetic acid ("EDTA") and salts thereof such as disodium EDTA, tetrasodium EDTA and calcium disodium EDTA; diethylenetriaminepentaacetic acid ("DTPA") and salts thereof; hydroxyethlethylenediaminetriacetic acid ("HEDTA") and salts thereof and nitrilotriacetic acid ("NTA"); more preferably EDTA, HEDTA and their salts; most preferably EDTA and its salts.

In one or more embodiments of the present disclosure a preferred non limiting example of the chelating agent is EDTA. Typically, the chelating and sequestering agent is present in the composition at a level of up to about 5.0%, preferably 1.0 percent, by weight, of the composition.

Combinations of Modulating Agents may be a useful aspect of the present disclosure. For example, as will be appreciated by a man of the art combinations of a strong acid and a weak base; a weak acid and a strong base: a weak acid and a strong acid; a weak base and a strong base; a weak base and a second weak base; and a weak acid and a second weak acid; may prove more effective in protecting or stabilizing an active agent in the waterless solvents of the present disclosure than a base or acid on its own. It will be understood that each of the active agents may have an artificial pH at which it can be more stable in a waterless composition. For example, ascorbic acid in aqueous solution is known to be more stable at an acidic pH of about 5.4. It is therefore desirable to add a combination of modulating agents in a waterless composition that will generate an artificial pH approximately of the order of or equivalent to that at which ascorbic acid is more stable in a waterless medium. In order to do so it will be appreciated a man of the art that that some adjustment will have to be made as ascorbic acid is itself a strong acid and displays the characteristics of a modulating agent. Similarly chelating agents may be usefully used in combination with another modulating agent such as an acid, a base or a buffer system or with various combinations of modulating agents.

The modulating agent to the foamable composition of the present disclosure is further useful for adjusting the pH of the target area of application. Skin is the first line of defense against all elements, such as microorganisms, wind, and pollutants, and it's the acid mantle, a fine film with a slightly acidic pH on the surface of the skin that provides protection for the skin. It plays a very important role as an integral part of the barrier function of the stratum corneum. Recent studies have demonstrated that increased enzyme activity of phospholipase A2 is related to the formation of the acid mantle in the stratum corneum. This combination makes the skin less permeable to water and other polar compounds. Normal skin surface pH is between 4 and 6.5 in healthy people, though it varies among the different areas of the skin. Newborn infants do have a higher skin surface pH compared to adults, but this normalizes within three days. Therefore, it is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since the best protection against vaginal infection is attained in pH lower than 4.

While the organic modulating agent can serve to stabilize an active agent in the foam composition, it often provides additional therapeutic properties to the composition. The following table exemplifies, in a non-limiting fashion, the therapeutic benefits expected from an organic modulating agent. It is to be understood that this table provides a non-exhaustive list of modulating agents that possess therapeutic effects, however, many other compounds listed in the present specification also possess therapeutic benefits.

| Class | Examples | Exemplary therapeutic properties |
| --- | --- | --- |
| Alpha hydroxy acids | Lactic acid | Humectant |
| | Glycolic acid | Keratnocyte growth modifier |
| | | Anti-psoriasis |
| | | Anti acne |
| Beta hydroxyl acid | Salicylic acid | Keratolytic |
| | | Antiinflammatory |
| Short chain carboxylic acid | Propionic acid Butyric acid | Antiinfective |
| Fatty acids | Nonanoic acid | Hair growth stimulant |
| | Behenic acid | Antiinflammatory |
| | | Antiinfective |
| | | Humectant |
| | | Skin protection |
| Unsaturated fatty acids | Omega-3 fatty acids | Radical scavenger |
| | Omega-6 fatty acids | Anti-oxidant |
| Aromatic acids | Benzoic acid | Antiinflammatory |
| | Phthalic acid | Anti-acne |
| | Nicotinic acid | Anti-pigmentation |
| | | Antiinfective |
| | | Insect repellant |
| Dicarboxylic acids | Malonic acid, succinic acid, glutaric acid, adipic acid, pimelic acid, suberic acid, azelaic acid, sebacic acid | Antiinflammatory Keratolytic Anti-acne Anti-rosacea Anti-pigmentation |
| Amino acids | | Keratnocyte growth modifier |
| | | Hair growth stimulant |
| | | Sebum control |
| Retinoids | Retinoic acid | Antiinflammatory |
| | Isotretinoin | Keratolytic |
| | | Anti-acne |
| | | Anti-rosacea |
| | | Anti-pigmentation |
| Nitrogen containing | Urea | Humectant |
| | | Keratolytic |
| | | Anti-psiriasis |

In an embodiment where the modulating agent is a buffer or pH adjuster surprisingly such modulating agents have been found to be incompatible with minocycline although they may in certain embodiments be compatible with doxycycline. In an embodiment the modulating agent is other than a buffer or pH modifier.

Anti-Oxidants/Radical Scavengers

In one or more embodiments, the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

A safe and effective amount of an anti-oxidant/radical scavenger may be added to the compositions of the subject disclosure, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox.sup.R), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

In one or more embodiments the modulating agent is a flavonoid.

Flavonoids (or bioflavonoids) are a large group of polyphenolic antioxidant compounds, which often occur as glycosides and are ubiquitously present in foods of plant origin. Some flavonoids (e.g. quercetin, rutin) are available as dietary supplements. Flavonoids can be further subdivided into:
  flavonols (e.g. kaempferol, quercetin and myricetin)
  flavones (e.g. apigenin and luteolin)
  flavonones (e.g. hesperetin, naringenin, eriodictyol)
  flavan-3-ols (e.g. (+)-catechin, (+)-gallocatechin, (−)-epicatechin, (−)-epigallocatechin)
  anthocyanins (e.g. cyanidin, delphinidin, malvidin, pelargonidin, peonidin, petunidin)
  proanthocyanidins.

More than 4000 flavonoids have been identified, and many have been studied. Most are colorless but some are responsible for the bright colors of many fruit and vegetables. Flavonoids are distinguished from the carotenoids.

Flavonoids appear to
  act as scavengers of free radicals, including superoxide anions, singlet oxygen, and lipid peroxyl radicals (they have antioxidant properties);
  sequester metal ions;
  inhibit in vitro oxidation of LDL cholesterol;
  inhibit cyclo-oxygenase, leading to lower platelet aggregation, decreased thrombotic tendency and reduced anti-inflammatory activity;
  inhibit histamine release;
  improve capillary function by reducing fragility of capillary walls and thus preventing abnormal leakage; and
  inhibit various stages of tumor development (animal studies only).

The activities of flavonoids are dependent on their chemical structure. Estimates of dietary flavonoid intake vary from 10 to 100 mg daily, but may be several hundreds of milligrams a day. Dietary supplements of quercetin and rutin provide around 500 mg in a single dose.

Flavonoids may have a potential role in the prevention of CVD, cancer and cataracts and possibly other diseases, for anti-viral activity, and they may be useful in treating ulcers. include hemorrhoids, allergy, asthma, menopausal symptoms and the prevention of habitual abortion.

Quercetin

As a dietary supplement, quercetin is promoted for prevention and treatment of atherosclerosis and hyperlipidaemia, diabetes, cataracts, hay fever, peptic ulcer, inflammation, prevention of cancer and for treating prostatitis. A preliminary, double-blind, placebo-controlled trial in chronic non-bacterial prostatitis showed that quercetin reduced pain and improved quality of life, but had no effect on voiding dysfunction.

Rutin

As a dietary supplement, rutin is used to reduce capillary permeability and treat symptoms of varicose veins. In combination with bromelain and trypsin, rutin is used to treat osteoarthritis.

A non limiting list of flavonoid compounds is: benzquercin, diosmin, ethoxazorutoside, flavodate, sodium hesperidin, leucocianido, monoxerutin, oxerutin, quercetin, rutoside, rosmarinic acid. The above information was noted from Dietary Supplements, Electronic Version, Pharmaceutical Press 2007.

In an embodiment a single flavonoid is provided and in a further embodiment a combination of two or more flavonoid are provided. In certain embodiments the flavonoids act synergistically. In an embodiment water soluble flavonoids are combined with water insoluble flavonoids. It is known for example that whole polyphenolic extracts have greater antioxidant effect than their known individual components. In an embodiment flavonoids are used in combination with other phenolics. In an embodiment one or more flavonoids are provided in combination with one or more vitamins. In an embodiment flavonoids are provided that are more reactive than the vitamins. In an embodiment the flavonoids act as a conservational agent.

Microsponges

The Microsponges are rigid, porous and spongelike round microscopic particles of cross-linked polymer beads (e.g., polystyrene or copolymers thereof), each defining a substantially noncollapsible pore network. The Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Miciponges with a waterless carrier described herein which may comprise a modulating agent.

Humectant

A humectant, is a substance that helps retain moisture and also prevents rapid evaporation. Non limiting examples of suitable heumectants are propylene glycol, propylene glycol derivatives, and glycerin. Further humectants include but are not limited to guanidine, urea, glycolic acid, glycolate salts, ammonium glycolate, quaternary alkyl ammonium glycolate, lactic acid, lactate salts, ammonium lactate, quaternary alkyl ammonium lactate, aloe vera, aloe vera gel, allantoin, urazole, alkoxylated glucose, hyaluronic acid, lactamide monoethanolamine, acetamide monoethanolamine and derivatives, esters, salts and mixtures thereof.

Other examples of humectants and moisturizers may be found in the Handbook of Pharmaceutical Additives published by Gower. Suitable ones for use with and soluble in the waterless compositions of the present disclosure may be selected as will be appreciated by a person skilled in the art.
Moisturizers A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Glycerine and sodium pCA work in combination. Other examples may be found in the *Handbook of Pharmaceutical Additives* published by Gower.

Pharmaceutical compositions of the present disclosure may in one or more embodiments usefully comprise in addition a humectant or a moisturizer or combinations thereof.
Additional Components In an embodiment of the present disclosure, a composition of the present disclosure includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

In an embodiment of the present disclosure, the additional component is a pH adjusting agent or a buffering agent. Suitable buffering agents include but are not limited to acetic acid, adipic acid, calcium hydroxide, citric acid, glycine, hydrochloric acid, lactic acid, magnesium aluminometasilicates, phosphoric acid, sodium carbonate, sodium citrate, sodium hydroxide, sorbic acid, succinic acid, tartaric acid, and derivatives, salts and mixtures thereof.

In an embodiment of the present disclosure, the additional component is a humectant.

In an embodiment no preservative is added since the formulation is a waterless oil base formulation having an Aw (Water Activity) value of less than 0.5 which is below the level of microbial proliferation. In certain limited an embodiments, the additional component is an oil soluble preservative. Suitable preservatives include but are not limited to C12 to C15 alkyl benzoates, alkyl p-hydroxybenzoates, aloe vera extract, ascorbic acid, benzalkonium chloride, benzoic acid, benzoic acid esters of C9 to C15 alcohols, butylated hydroxytoluene, castor oil, cetyl alcohols, chlorocresol, citric acid, cocoa butter, coconut oil, diazolidinyl urea, diisopropyl adipate, dimethyl polysiloxane, DMDM hydantoin, ethanol, fatty acids, fatty alcohols, hexadecyl alcohol, hydroxybenzoate esters, iodopropynyl butylcarbamate, isononyl iso-nonanoate, jojoba oil, lanolin oil, methylparaben, mineral oil, oleic acid, olive oil, polyoxypropylene butyl ether, polyoxypropylene cetyl ether, potassium sorbate, silicone oils, sodium propionate, sodium benzoate, sodium bisulfite, sorbic acid, stearic fatty acid, vitamin E, vitamin E acetate and derivatives, esters, salts and mixtures thereof.

In an embodiment of the present disclosure, the additional component is a skin penetration enhancer.
Propellants Examples of suitable propellants include volatile hydrocarbons such as butane, propane, isobutane and fluorocarbon gases, or mixtures thereof.

In an embodiment the propellant is 1681, which is a mixture of propane, isobutene and butane. In another embodiment it is AP 70, which is a mixture of propane, isobutene and butane with a higher pressure.

The propellant makes up about 5-25 wt % of the foamable composition. In some circumstances the propellant may be up to 35%. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMCs), which are non-ozone-depleting propellants, are particularly useful in the production of a non-flammable foamable composition. A test according to European Standard prEN 14851, titled "Aerosol containers-Aerosol foam flammability test" revealed that compositions containing an organic carrier that contains a hydrophobic organic carrier and/or a solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the disclosure include propellants made by DuPont under the registered trademark Dymel, such as 1,1,1,2 tetrafluorethane (Dymel 134), and 1,1,1,2,3,3,3 heptafluoropropane (Dymel 227) 1,1, difluoro ethane (Dymel 152) and 1,1,1,3,3,3 hexafluoropropane HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butane or mixtures of hydrocarbon propellants such as propane, isobutane and butane.
Hygroscopic Property of the Composition A hydroscopic substance is a substance that absorbs water readily from its surroundings. Microorganisms require water to grow and reproduce, and such water requirements are best defined in terms of water activity of the substrate. The water activity of a solution is expressed as $A_w=P/Po$, where P is the water vapor pressure of the solution and Po is the vapor pressure of pure water at the same temperature. Addition of a hygroscopic substance to an aqueous solution in which a microorganism is growing will have the effect of lowering the Aw, with a consequent effect upon cell growth. Every microorganism has a limiting Aw, below which it will not grow, e.g., for streptococci, *klebsiella* spp., *escherichia coli, clostridium perfringens*, and *pseudomonas* spp. the $_Aw$ value is 0.95. *Staphylococcus aureus* is most resistant and can proliferate with an $A_w$ as low as 0.86.

The water activity of a product can be determined from the relative humidity of the air surrounding the sample when the air and the sample are at equilibrium. Measurement is performed by placing a sample in an enclosed space where this equilibrium can take place. Once this occurs, the water activity of the sample and the relative humidity of the air are equal. The measurement taken at equilibrium is called an equilibrium relative humidity or ERH. The relationship between the water activity and ERH is in accordance with the following formula:

$$A_w = ERH/100$$

Various types of water activity instruments are commercially available. One exemplary instrument uses chilled-mirror dewpoint technology while other instruments measure relative humidity with sensors that change electrical resistance or capacitance.

Polyols, PEGs and other solvents have a great affinity for water, and as such, they exhibit hygroscopic properties. The concentration of the polyol, the PEG and/or other solvents determines the Aw of the carrier. In one or more embodiments, the polyols, the PEG and/or the secondary solvent is contained in the composition of the present disclosure at a sufficient concentration to provide an $A_w$ value of the hygroscopic carrier of less than 0.9. In other embodiments, the concentration of the polyol, the PEG and/or secondary solvent in the composition is selected to provide an $A_w$ value selected from the ranges of (1) about 0.8 and about 0.9; (2) about 0.7 and about 0.8; and (3) less than about 0.7.

As such, a composition containing a polyol, a PEG with or without a secondary solvent can be used as topical treatment of superficial infectious conditions.

The advantage of providing a hygroscopic composition in a pressurized packaging presentation is readily perceived. The usage of all other presentations, such as solutions, creams, lotions, ointments and the like involves repeated opening of the package closure, resulting in absorption of water from the surrounding environment and a subsequent elevation of the $A_W$ (thus lowering the hygroscopicity of the product, and therefore decreasing its anti-infective potential. By contrast, a pressurized packaging does not allow for any humidity to be absorbed by the preparation, and therefore, the hygroscopic character of the composition cannot be damaged.

In one or more embodiments, the hygroscopic composition of the present disclosure further contains an anti-infective agent, selected from the group of an antibiotic agent, an antibacterial agent, an antifungal agent, an agent that controls yeast, an antiviral agent and an antiparasitic agent. Combining the anti-infective effect of a hygroscopic composition, which acts through a dehydration mechanism, together with an additional anti-infective agent, that acts through alternate mechanisms, results in a synergistic effect and consequently higher success rate of the treatment.

Composition and Foam Physical Characteristics and Advantages

A pharmaceutical or cosmetic composition manufactured using the foamable carrier of the present disclosure is very easy to use. When applied onto the body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present disclosure is stable, having an acceptable shelf-life of at least one year, or preferably, at least two years at ambient temperature, as revealed in accelerated stability tests. Organic carriers and propellants tend to impair the stability of emulsions and to interfere with the formation of stable foam upon release from a pressurized container. It has been observed, however, that the foamable compositions according to the present disclosure are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Quantitative and Qualitative

Foam Quality

Foam quality can be graded as follows:

Grade E (excellent): very rich and creamy in appearance, does not show any bubble structure or shows a very fine (small) bubble structure, does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

Foam Physical Characteristics

In terms of foam consistency and texture an acceptable foam is one, that exhibits the following characteristics:

Upon release from an aerosol can, creates a foam mass, which is sustained on a surface for at least one minute, more preferably at least two minutes, and yet more preferably for at least 5 minutes.

Foam texture should vary from a very fine creamy foam to a fine bubble structure.

Foam has to have specific gravity in the range of about 0.02 gr/mL to about 0.5 gr/mL, more preferably between about 0.04 gr/mL and about 0.2 gr/mL In terms of spreadability and absorption an acceptable foam is one, that does not readily collapse upon dispensing on the skin; spreads easily on a skin surface; at least partially absorbed following rubbing onto the skin, and more preferably, substantially absorbed following rubbing on the skin.

In terms of tactile properties an acceptable foam is one, that: creates a pleasant feeling after application; leaves minimal oily residue; and leaves minimal shiny residual look.

Foam Collapse

A further aspect of the foam is breakability. Thermally sensitive foams immediately collapse upon exposure to skin temperature and, therefore, cannot be applied on the hand and afterwards delivered to the afflicted area.

The foam of the present disclosure has several notable advantages, when compared with hydroalcoholic foam compositions, such as (1) Breakability. The foam of the present disclosure is thermally stable and breakable under sheer force but is not "quick breaking which allows comfortable application and well directed administration to the target area;

(2) Skin drying and skin barrier function. Short chain alcohols are known to dry the skin and impair the integrity of the skin barrier. By contrast, including a film forming agent in the composition of the present disclosure foes not cause unwanted skin barrier damage.

(3) Irritability. Due to the lack of lower alcohols (C1-C5) and improvement in skin barrier function, skin irritability is eliminated.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable composition of the present disclosure (also referred to herein as the foamable pharmaceutical composition) is an ideal vehicle for active pharmaceutical ingredients and/or active cosmetic ingredients. In the context of the present disclosure, active pharmaceutical ingredients and active cosmetic ingredients are collectively termed "active agent" or "active agents". The silicone and oil waterless formulations optionally coupled with the use of modulating agents can uniquely be adapted to protect and preserve active agents when stored in compatible sealed canisters with propellant A foamable composition, comprising an active agent has the following advantages:

1. The foamable composition provides a preferred solvent for active agents, particularly for poorly soluble or water-insoluble agents.
2. The provision of an essentially single phase foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily. Oils with a secondary solvent can act as skin penetration enhancers, thus, increasing drug residence time in the target area and increasing clinical efficacy, as detailed above.
   Similarly, the inclusion of a polyol and/or a PEG and/or a polyol ether and in the foamable composition facilitates a co-solvent effect, resulting increased concentrations of soluble active agent in the dosage form, thus facilitating enhanced skin penetration of the active agent. In many cases, increased penetration is positively correlated with improved clinical outcome. In certain case, attaining an increased drug penetration into the target site of action enables a decrease of treatment frequency, for example, from twice or three times daily to once daily.
3. Polyols, polyol ethers and PEGs; and combinations of a polyol and/or PEG with a secondary solvent are known as skin penetration enhancers, thus, increasing drug residence time in the target area and increasing clinical efficacy, as detailed above.
4. The fact that the composition contains no or little water, minimizes the probability of degradation of water-sensitive active agents. Furthermore, as exemplified herein, a foam containing a polyol, a polyol ether and/or PEG with no water at all can be formed in accordance with the composition and process of the present disclosure. Such compositions ensure high stability of water sensitive active agents.
5. Combining the anti-infective effect of a hygroscopic composition, which acts through a dehydration mechanism, with an additional anti-infective agent, selected from the group of an antibiotic agent, an antibacterial agent, an antifungal agent, an agent that controls yeast, an antiviral agent and an antiparasitic agent, that acts through alternate mechanisms results in a synergistic effect and consequently higher success rate of the treatment.
6. The foamable polyol composition in contained in an impermeable pressurized packaging presentation is impermeable and thus, the active agent is not exposed to environmental degradation factors, such as light and oxidating agent during storage.

Thus, in one or more embodiments, the foamable composition includes at least one therapeutic agent, in a therapeutically effective concentration. Therapeutic agents are described herein. In addition, compounds disclosed in International Patent Publication No. WO 2004/03284, which is incorporated by reference in its entirety are suitable for use in the pharmaceutical compositions described herein.

In an embodiment the therapeutic agent is soluble in the foamable composition. In alternative embodiments the therapeutic agent is partially soluble and in further embodiments the therapeutic agent is insoluble in the formulation. Where the agent is insoluble or partially soluble it is provided as a homogenous suspension. In certain embodiments the homogeneous suspension remains homogenous over a substantial period of time suitable for pharmaceutical use. In other embodiments the agent may cram or separate out but homogeneity is fully reversible on shaking.

Oil soluble active agents may be readily used in the oil/silicone surfactant compositions described herein. A short list of non limiting examples of oil soluble active agents include calcipotriol, calcitriol, ciclopirox olamine, benzocaine. Other examples are terbinofine, diclofenac, tacrolimus and pimecrolimus and also oil soluble vitamins. Estradiol, progesterone are non limiting examples of sparingly oil soluble agents.

Because the prefoam formulations can provide a substantially waterless, high oil content environment, particular classes of active pharmaceutical ingredients (APIs) will benefit from their inclusion in the composition. For example, active agents that are water sensitive, such as minocycline, doxycycline and other tetracycline drugs, vitamin D (e.g., calcipotriol and calcitriol), can have improved stability in the waterless composition. API's that are esters or amides are generally prone to hydrolysis by water and would benefit from a water free oil environment. API's that are sensitive to free radical attack or oxidation also would benefit from a water free oil environment. Similarly, active agents that are sensitive to specific pH level (which prevails in the presence of water) will also benefit. Exemplary APIs that would benefit from the silicone waterless compositions according to one or more embodiments include Vitamin D analogs and derivatives that degrade at low pH and corticosteroids that degrade at high pH. Oil soluble drugs can also be included in the compositions, such as corticosteroids, immunomodulators, such as tacrolimus and pimecrolimus, oil-soluble vitamins, e.g., vitamin A and derivatives thereof, other retinoids, vitamin E. Certain APIs may possess more than one of the above features, and thereby benefit even further from the silicone waterless compositions.

Thus, in a preferred embodiment of the present disclosure, the composition includes at least one active agent.

a. a therapeutically effective concentration of an active agent;
b. 10% to 30% by weight of at least one unstable active agent-compatible (UAAC) excipient selected from the group consisting of (1) a polyol and (2) a polyol ether;
c. 10% to 60% by weight of at least one unstable active agent-compatible (UAAC) emollient and or hydrophobic solvent;
d. A stabilizing agent selected from the group consisting of about 0.01% to about 25% by weight of at least one surface-active agent; and about 0% to about 5% by weight of at least one polymeric agent and mixtures thereof;
e. about 0 to about 10% by weight of at least one alcohol; and
f. a liquefied or compressed gas propellant at a concentration of about 3% to about 25% by weight of the total composition.

Antibiotics

In the context of the present disclosure, an antibiotic agent is a substance, that has the capacity to inhibit the growth of or to destroy bacteria and other microorganisms.

In one or more embodiments, the antibiotic agent is selected from the classes consisting beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, dicarboxylic acids, antibiotic metals including antibiotic metal ions, oxidizing agents, a periodate, a hypochlorite, a permanganate, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds including non classified antibiotic compounds analogs, derivatives, salts, ions, complexes and mixtures thereof:

Tetracyclines

The tetracyclines (also referred to herein as "tetracycline antibiotics") are a group of antibacterials, originally derived from certain *Streptomyces* spp., having the same tetracyclic nucleus, naphthacene, and similar properties. They are usually bacteriostatic but act by interfering with protein synthesis in susceptible organisms. Tetracycline antibiotics are susceptible to degradation by oxidation.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Chlortetracycline, oxytetracycline, tetracycline, demeclocycline are all natural products that have been isolated from *Streptomyces* spp. The more recent tetracyclines, namely methacycline, doxycycline, and minocycline, are semisynthetic derivatives. Methacycline, like demeclocycline, has a longer half-life than tetracycline. Minocycline is active against some tetracycline-resistant bacteria, including strains of staphylococci. Both doxycycline and minocycline are more lipid-soluble than the other tetracyclines and they penetrate well into tissues. They are thus more suitable for incorporating into oily or emollient containing formulations. However, they have a place in the treatment of chlamydial infections, rickettsial infections such as typhus and the spotted fevers, mycoplasmal infections such as atypical pneumonia, pelvic inflammatory disease, Lyme disease, brucellosis, tularaemia, plague, cholera, periodontal disease, and acne. The tetracyclines have also been useful in the treatment of penicillin-allergic patients suffering from venereal diseases, actinomycosis, bronchitis, and leptospirosis. Minocycline may sometimes be used in multidrug regimens for leprosy. Doxycycline may be used for the treatment and prophylaxis of malaria; it is also used in the management of anthrax.

In an embodiment the active ingredient may be any one of the following non limiting examples chlortetracycline, demeclocycline, doxycycline, lymecycline, meclocycline, methacycline, minocycline, oxytetracycline, rolitetracycline, tetracycline. In a preferred embodiment they are doxycyline or minocycline.

Tetracyclines and Skin Infections

Tetracyclines have been used in ophthalmic ointments for the prevention or treatment of infections of the eye caused by susceptible bacteria. Although minor skin infections and wounds usually heal without treatment, some minor skin wounds do not heal without therapy and it is impossible to determine at the time of injury which wounds will be self-healing. Therefore, some experts believe that, by reducing the number of superficial bacteria, topical anti-infectives are useful for preventing infection in minor skin injuries (e.g., cuts, scrapes, burns).

Tetracycline hydrochloride may be used topically in the treatment of inflammatory acne vulgaris. Tetracyclines are usually bacteriostatic in action, but may be bactericidal in high concentrations or against highly susceptible organisms.

Tetracyclines appear to inhibit protein synthesis in susceptible organisms primarily by reversibly binding to 30S ribosomal subunits, thereby inhibiting binding of aminoacyl transfer-RNA to those ribosomes. In addition, tetracyclines appear to reversibly bind to 50S ribosomal subunits. There is preliminary evidence that tetracyclines also alter cytoplasmic membranes of susceptible organisms resulting in leakage of nucleotides and other intracellular components from the cell. At high concentrations, tetracyclines also inhibit mammalian protein synthesis.

The exact mechanisms by which tetracyclines reduce lesions of acne vulgaris have not been fully elucidated; however, the effect appears to be partly the result of the antibacterial activity of the drugs. Following topical application to the skin of a 0.22% solution of tetracycline hydrochloride in a vehicle containing n-decyl methyl sulfoxide (Topicycline®; no longer commercially available in the US), the drug inhibits the growth of susceptible organisms (principally *Propionibacterium acnes*) on the surface of the skin and reduces the concentration of free fatty acids in sebum. The reduction in free fatty acids in sebum may be an indirect result of the inhibition of lipase-producing organisms which convert triglycerides into free fatty acids or may be a direct result of interference with lipase production in these organisms. Free fatty acids are comedogenic and are believed to be a possible cause of the inflammatory lesions (e.g., papules, pustules, nodules, cysts) of acne. However, other mechanisms also appear to be involved because clinical improvement of acne vulgaris with topical tetracyclines does not necessarily correspond with a reduction in the bacterial flora of the skin or a decrease in the free fatty acid content of sebum. (Martindale Electronic Version 2007)

Doxycyline

Doxycycline is a tetracycline antibiotic and also has anti-inflammatory and immunomodulatory effects. Doxycycline is a semisynthetic tetracycline antibiotic derived from oxytetracycline. In addition to antimicrobial activity, the drug has anti-inflammatory and immunomodulatory effects. It is available as Doxycycline calcium, doxycycline hyclate and doxycycline monohydrate. Doxycycline hyclate and doxycycline monohydrate occur as yellow, crystalline powders. The hyclate is soluble in water and slightly soluble in alcohol; the monohydrate is very slightly soluble in water and sparingly soluble in alcohol. Doxycycline calcium is formed in situ during the manufacturing process. Following reconstitution of doxycycline hyclate powder for IV administration with sterile water for injection, solutions have a pH of 1.8-3.3.

The mechanism(s) by which doxycycline reduces inflammatory lesions (papules and pustules) in patients has not been elucidated, but these effects may result at least in part from the anti-inflammatory actions of the drug; other mechanisms may be involved.[2]

Doxycycline is used for the treatment of rosacea treatment or prophylaxis of anthrax (including inhalational anthrax [postexposure]), treatment of presumed or confirmed rickettsial infections, including Rocky Mountain spotted fever (RMSF), fever, ehrlichiosis, and anaplasmosis, and for the treatment of *Bartonella* infections, for the treatment of brucellosis, for the treatment of *Burkholderia* Infections, Chlamydial Infections, Lymphogranuloma venereum Psittacosis, Ehrlichiosis and Anaplasmosis, Gonorrhea and Associated Infections, Epididymitis, Proctitis, Granuloma Inguinale (Donovanosis,) *Legionella* Infections, Leptospirosis, Lyme Disease, Prophylaxis of Lyme Disease, Erythema Migrans, Early Neurologic Lyme Disease, Lyme Carditis, or Borrelial Lymphocytoma, Lyme Arthritis, Malaria, and prevention, Mycobacterial Infections, *Mycobacterium marinum* Infections, Pelvic Inflammatory Disease, Parenteral Regimens, Plague, pleural Effusion, Rickettsial Infections, Q Fever, Syphilis, Tularemia, Treatment, Postexposure Prophylaxis When reconstituted and diluted with 0.9% sodium chloride or 5% dextrose, doxycycline hyclate IV solutions containing 0.1-1 mg of doxycycline per mL are stable for 48 hours at 25° C.; when reconstituted and diluted with Ringer's, 10% invert sugar, Normosol-M® in D5W, Normosol-R® in D5W, Plasma-Lyte® 56 in 5% dextrose, or Plasma-Lyte® 148 in 5% dextrose, doxycycline hyclate IV solutions containing 0.1-1 mg/mL are stable for 12 hours at room temperature. The manufacturer states that doxycycline hyclate solutions prepared with any of these infusion solutions are stable for 72 hours at 2-8° C. when protected from direct sunlight and artificial light; however, after storage in this manner, infusion of these solutions must be completed within 12 hours Doxycycline hyclate IV solutions diluted to a concentration of 0.1-1 mg/mL with lactated Ringer's injection or 5% dextrose in lactated Ringer's injection must be infused within 6 hours to ensure stability. During infusion, all doxycycline hyclate IV solutions must be protected from direct sunlight. (Martindale 2007 Electronic Version). Thus it can be seen that Doxycycline is not stable for more than short periods of a matter of hours.

Preparations of doxycycline hyclate have an acid pH and incompatibility may reasonably be expected with alkaline preparations or with drugs unstable at low pH.

Doxycycline is more active than tetracycline against many bacterial species including *Streptococcus pyogenes*, enterococci, *Nocardia* spp., and various anaerobes. Cross-resistance is common although some tetracycline-resistant *Staphylococcus aureus* respond to doxycycline. Doxycycline is also more active against protozoa, particularly *Plasmodium* spp.

Doxycycline is a tetracycline derivative with uses similar to those of tetracycline. It may sometimes be preferred to other tetracyclines in the treatment of susceptible infections because of its fairly reliable absorption and its long half-life that permits less frequent (often once daily) dosing. It also has the advantage that it can be given (with care) to patients with renal impairment. However, relatively high doses may need to be given for urinary-tract infections because of its low renal excretion.

For relapsing fever and louse-borne typhus, for the prophylaxis of leptospirosis, for periodontiti, for Lymphatic filariasis, for Musculoskeletal and joint disorders and for the treatment of acne.

Minocycline Hydrochloride

Minocycline hydrochloride is a semisynthetic tetracycline antibiotic derived from tetracycline. The drug is usually bacteriostatic in action; it exerts its antimicrobial activity by inhibiting protein synthesis. It is a yellow crystalline powder that is sparingly soluble in water; slightly soluble in alcohol; practically insoluble in chloroform and in ether; soluble in solutions of alkali hydroxides and carbonates. pH of a solution in water containing the equivalent of minocycline 1% is between 3.5 and 4.5. Preparations of minocycline hydrochloride have an acid pH and incompatibility may reasonably be expected with alkaline preparations or with drugs unstable at low pH.

It is highly sensitive and should be stored in airtight containers and protected from light. Therefore use in foamable formulations stored in airtight sealed containers under pressure with propellant may contribute to preserving stability subject to selection of compatible canisters and accessories Photosensitivity, manifested as an exaggerated sunburn reaction on areas of the body exposed to direct sunlight or ultraviolet light, has occurred with tetracyclines and Minocycline has been associated with pigmentation of the skin and other tissues Minocycline has a spectrum of activity and mode of action similar to that of tetracycline but it is more active against many species including *Staphylococcus aureus*, streptococci, *Neisseria meningitidis*, various enterobacteria, *Acinetobacter*, *Bacteroides*, *Haemophilus*, *Nocardia*, and some mycobacteria, including *M. leprae*. Partial cross-resistance exists between minocycline and other tetracyclines but some strains resistant to other drugs of the group remain sensitive to minocycline, perhaps because of better cell-wall penetration. Minocycline is a tetracycline derivative with uses similar to those of tetracycline. It is also a component of multidrug regimens for the treatment of leprosy and has been used in the prophylaxis of meningococcal infection to eliminate the carrier state, but the high incidence of vestibular disturbances means that it is not the drug of choice for the latter. It has neuroprotective properties. It is being investigated for motor neurone disease, for the management of Huntington's chorea. It is used in the treatment of rheumatoid arthritis and in the treatment of various skin disorders, including acne.

Additional Therapeutic Agent and Antibiotics

Several disorders of the target site (such as the skin, a body surface, a body cavity, a mucosal surface, the nose, the mouth, the eye, the ear canal, the respiratory system, the vagina and the rectum), involve a combination of etiological factors, some of which are related to a microbiological infection (that can be affected by an antibiotic agent); and other etiological factors that require an additional therapeutic modality. For example, impetigo involves bacterial infection as well as inflammation, and therefore combined treatment with an antibiotic agent and an anti-inflammatory agent would be beneficial. Likewise, chronic ulcers involve poor blood supply and potential bacterial, fungal and viral infections, which warrants a beneficial effect of a combination of an antibiotic agent and a vasoactive agent.

Additional non-limiting examples of combinations of an antibiotic agent and an additional active agent are provided in the following table:

| Disorder | Exemplary Additional Active Agent |
|----------|-----------------------------------|
| acne | At least one agent selected from the group consisting of a retinoid; a keratolytic acid, an alpha-hydroxy acid and derivatives thereof, a beta-hydroxy acid and derivatives thereof, a skin-drying agent, an anti-seborrhea agent, a corticosteroid and a non-steroidal anti-inflammatory agent.. |
| Rosacea | At least one agent selected from the group consisting of a retinoid; a keratolytic acid, an alpha-hydroxy acid, a beta-hydroxy acid and derivatives thereof. |
| Otitis | At least one agent selected from the group of an antifungal agent, a local anesthetic agent, a corticosteroid and a non-steroidal anti-inflammatory agent. |
| Psoriasis | At least one agent selected from the group consisting of a corticosteroid, coal tar, anthralin and a photodynamic therapy agent |

Hence, in many cases, the inclusion of an additional therapeutic agent in the foamable composition of the present disclosure, contributes to the clinical activity of the antibiotic agent.

Thus, in one or more embodiments, the foamable composition further includes at least one additional therapeutic agent, in a therapeutically effective concentration.

In one or more embodiments, the at least one additional therapeutic agent is selected from the group consisting of a steroidal antiinflammatory agent, a nonsteroidal anti-inflammatory drug, an immunosuppressive agent, an immunomodulator, an immunoregulating agent, a hormonal agent, an antifungal agent, an antiviral agent, an antiparasitic agent, a vasoactive agent, a vasoconstrictor, a vasodilator, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an anti-allergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, an antibiotic agent, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

Fields of Applications

The foamable carrier of the present disclosure is suitable for treating any infected surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

By selecting a suitable active agent, or a combination of at least two active agents, the foamable composition of the present disclosure is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present disclosure is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present disclosure, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present disclosure, the composition is useful for the treatment of wound, ulcer and burn. This use is particularly important since the composition of the present disclosure creates a thin, semi-occlusive layer, which coats the damaged tissue, while allowing exudates to be released from the tissue.

The composition of the present disclosure is also suitable for administering a hormone to the skin or to a mucosal membrane or to a body cavity, in order to deliver the hormone into the tissue of the target organ, in any disorder that responds to treatment with a hormone.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or solvents due to their skin-irritating effect. Thus, the composition is substantially alcohol-free and includes less than about 5% final concentration of lower alcohols, preferably less than about 2%, more preferably less than about 1%.

Shakability

'Shakability' means that the composition contains some or sufficient flow to allow the composition to be mixed or remixed on shaking. That is, it has fluid or semi fluid properties. In some very limited cases it may still be possible to have a foamable composition which is flowable but not apparently shakable.

Breakability

A breakable foam is thermally stable or substantially so, yet breaks under sheer force. The breakable foam of the present disclosure is not "quick breaking", i.e., it does not readily collapse upon exposure to body temperature environment. Sheer-force breakability of the foam is clearly advantageous over thermally induced breakability, (due to, for example, the presence of alcohol) since it allows comfortable application and well directed administration to the target area.

Chemical Instability and Stability

By chemical instability of one or more active agents is meant that at least one of the one or more active agents is susceptible to one or more of inter alia reaction, breakdown, ionization or oxidation or the rate thereof is increased when incorporated into a pharmaceutical or cosmetic carrier that is non aqueous or substantially non aqueous.

Conversely by chemical stability of one or more active agents is meant that at least one of the one or more active agents is less susceptible to one or more of inter alia reaction, breakdown, ionization or oxidation or the rate thereof is impeded when incorporated into a pharmaceutical or cosmetic carrier that is non aqueous or substantially non aqueous.

"Chemically stable" or "chemical stability" may be defined as demonstrating substantially no or minimal breakdown from oxidation 72 hours after mixing with the carrier or agent when stored at about at least 25° C. Substantially no or minimal breakdown may be determined using HPLC methods disclosed herein or other methods, where the mass of the compound is determined at time 0 (i.e., within about 1 hour after mixing with the carrier or foamable pharmaceutical composition) and about 72 hours after mixing, and wherein at least about 90% by mass of the compound is detected at about 72 hours compared to time 0. Alternatively, degradation products may be determined using HPLC methods disclosed herein or other methods, where the mass of the degradation products is determined at time 0 and about 72 hours after mixing, and wherein less than about 1% by mass of the compound in the mixture is degradation products. When the compound is minocycline, a suitable degradation product for purposes of determining "chemical stability" or "chemically stable" is 4-epiminocycline.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. Publication No. 2007-0292355 published on Dec. 20, 2007 and entitled ANTI-INFECTION AUGMENTATION OF FOAMABLE COMPOSITIONS AND KIT AND USES THEREOF; U.S. Publication No. 2008-0069779 and entitled DICARBOXYLIC ACID FOAMABLE VEHICLE AND PHARMACEUTICAL COMPOSITIONS THEREOF; U.S. Publication 20080206159, published on Aug. 28, 2008 and entitled COMPOSITIONS WITH MODULATING AGENTS; U.S. patent application Ser. No. 11/767,442, filed on Jun. 22, 2007, entitled FOAMABLE COMPOSITIONS AND KITS COMPRISING ONE OR MORE OF A CHANNEL AGENT, A CHOLINERGIC AGENT, A NITRIC OXIDE DONOR, AND RELATED AGENTS AND THEIR USES; U.S. Publication 2008-0069779, published on Mar. 20, 2008 and entitled FOAMABLE VEHICLE AND VITAMIN AND FLAVONOID PHARMACEUTICAL COMPOSITIONS THEREOF, all of which are incorporated herein by reference in their entirety. More particularly any of the active ingredients; the solvents; the surfactants; foam adjuvants; penetration enhancers; humectants; moisturizers; and other excipients as well as the propellants listed therein can be applied herein and are incorporated by reference.

The present disclosure is described with reference to the following examples. This disclosure is not limited to these examples and experiments. Many variations will suggest themselves and are within the full intended scope of the appended claims.

Methodology

The formulas of the present disclosure may be made in the following general way with appropriate adjustments for each formulation as will be appreciated by someone skilled in the art. Polymers, if any, are mixed, swelled and solubilized in the waterless medium, when necessary, with appropriate heat until it forms a clear solution. Stabilizing surfactants added usually with heat, until a homogeneous mixture is obtained, the mixture is then allowed to cool. The remainder of the ingredients, are then added with mixing until they have dissolved in the medium. The active agent is usually added at the end once the modulating agent, if present, has been incorporated. For foam the canisters are then filled with the above waterless formula, sealed and crimped with a valve and pressurized with the propellant.

A general procedure for preparing foamable compositions is set out in WO 2004/037225, which is incorporated herein by reference.

Waterless Foam
1. Dissolve the polymers, if any, in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

Note that for substantially waterless foam a small amount of water is added before step 2.

Oily Waterless Foam
1. Mix all ingredients excluding polymers and heat to 75° C. to melt and dissolve and obtain homogeneous mixture.
2. Mix well and cool to below 40° C. and add the polymers, if any, and sensitive ingredients with moderate mixing.
3. Cool to room temperature.

Note that for substantially waterless foam a small amount of water is added before step 2.

Oily Foam with Phospholipids
1. Swell the phospholipids in the main oily solvent under mixing for at least 20 minutes until uniform suspension is obtained.
2. Add all other ingredients excluding polymers and heat to 75° C. to melt and dissolve and obtain homogeneous mixture.
3. Mix well and cool to below 40° C. and add the polymers, if any, and sensitive ingredients with moderate mixing.
4. Cool to room temperature.
5. In case of polymers dissolved or organic solvent, dissolve the polymers in the solvent with heating or cooling as appropriate for specific polymer and add to the oily mixture under vigorous mixing at ~40° C.

Note that for substantially waterless foam a small amount of water is added step 5. For more details of procedures please see the specific descriptions in the Examples.

Production Under Vacuum

Optionally, the foamable formulation may be produced under nitrogen and under vacuum. Whilst the whole process can be carried out under an oxygen free environment, it can be sufficient to apply a vacuum after heating and mixing all the ingredients to obtain an emulsion or homogenous liquid. Preferably the production chamber is equipped to apply a vacuum but if not the formulation can be for example placed in a dessicator to remove oxygen prior to filing and crimping.

Canisters Filling and Crimping

Each aerosol canister is filled with PFF and crimped with valve using vacuum crimping machine. The process of applying a vacuum will cause most of the oxygen present to be eliminated. Addition of hydrocarbon propellant may without being bound by any theory further help to reduce the likelihood of any remaining oxygen reacting with the active ingredient. It may do so, without being bound by any theory, by one or more of dissolving in the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing

Propellant Filling

Pressurizing is carried out using a hydrocarbon gas or gas mixture. Canisters are filled and then warmed for 30 sec in a warm bath at 50° C. and well shaken immediately thereafter.

Closure Integrity Test.

Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.

Tests

By way of non limiting example the objectives of hardness, collapse time and FTC stability tests are briefly set out below as would be appreciated by a person of the art.

Hardness

LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can affect the degree of dermal penetration, efficacy, spreadability and acceptability to the user. The results can also be looked at as an indicator of softness. Note: the foam sample is dispensed into an aluminum sample holder and filled to the top of the holder.

Collapse Time

Collapse time (CT) is examined by dispensing a given quantity of foam and photographing sequentially its appearance with time during incubation at 36° C. It is useful for evaluating foam products, which maintain structural stability at skin temperature for at least 1 min.

Viscosity

Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

FTC (Freeze Thaw Cycles)

To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.

Chemical Stability

The amount of active agent present is analyzed in foam expelled from various pressurized canisters containing foam formulations using HPLC. Analysis is carried out at zero time and at appropriate time intervals thereafter. The canisters are stored in controlled temperature incubators at 5° C., at 25° C., at, 40° C. and at 50° C. At appropriate time intervals canisters are removed and the amount of active agent in the foam sample is measured.

Analysis

Analysis of Antibiotic Concentrations in Formulations i) Minocycline Formulations:

About 0.5 g foam or pre-foam formulation is dissolved with diluent (65% phosphate buffer: 35% Acetonitrile (ACN)) in a 25 mL volumetric flask. The sample is shaken for 30 min on an inverted shaker stand for 10 min at room temperature. The resulting suspension is centrifuged for 5 minutes at 4000 rpm. The supernatant is separated by vacuum pump and filtered thereafter through a 0.45 µm PTFE+GL filter. The first few drops of the filtrate are discarded. The resultant clear solution layer is analyzed by HPLC using columnRP-8. The content of MCH is calculated against an MCH standard 0.4 mg/mL (concentration). The content of 4-epiminocycline is calculated against MCH standard 0.02 mg/mL (concentration).

The details of the method conditions are as follows:

| Column: | Purosphere STAR RP-8 endcapped 5µ Merck 250 x |
|---|---|
| Cat. | 4.6 |
|  | 1.50032.0001 |
| Flow: | 1.2 mL/min |
| Detector: | UV at 254 nm |
| Injection volume: | 10 µL |
| Autosampler temp.: | 5° C. |
| Column temp.: | 40° C. |
| Mobile phase: | 78 buffer: 22 ACN |
| Diluent: | 65 buffer: 35 ACN |
| Approximate RT: | 11.5 min for minocycline HCl |
|  | 8 min for 4-epiminocycline | ii) Doxycycline (Dox) Formulations:

About 1 g of pre-foam formulation or foam is weighed into 50 ml plastic centrifuge tube. 25 ml of 0.01N HCl (diluent) and 15 ml of dichloromethane are added. The mixture is shaken for 1 hour an inverted shaker stand and thereafter centrifuged for 5 minutes at 4000 rpm. The supernatant is separated by vacuum pump and filtered thereafter through a 0.45 µm PTFE+GL filter. The first few drops of the filtrate are discarded. The resultant clear solution layer is sampled and injected into an HPLC, using a C-8 column. The content of MCH is calculated against DOX prepared in 1 g placebo with AN 0.2 mg/mL standard.

The details of the method conditions are as follows:
Column: Thermo Hypersil GOLD C-8 250×4.6 mm 5µ cat: 25205-254630.
Column temp: 35° C.
Flow 1.0 ml/min,
Injection volume 10 µL.
Detector: UV at 270 nm
Gradient for 25 min with post time: 15 min.

Visual Stability Tests

Spillability

In most formulations, addition of Minocycline HCl per se causes to loss of fluidity (the formulation becomes a thickened mass). This is undesirable phenomenon. Therefore an objective in designing lead formulations it to formulate so the compostion does not lose fluidity, and stays spillable after the incorporation of active agent. Spillability means free moving or rotating of formulation inside the glass bottle upon inversion.

Chemical Oxidation

Chemical oxidation of the active ingredient in the foam formulation can be noticed visually (e.g. changing the color from yellow to orange). See color test. Oxidation results in a lower assay. Degradation of minocycline can be an epimerization chemical process (4-epiminocycline).

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DG HSM). Pictures obtained are cropped to keep a squared region of 400 pixels×400 pixels.

Microscope Size:

The light microscope enables observing and measuring particles from few millimeters down to one micron. Light microscope is limited by the visible light wavelength and therefore is useful to measuring size of particles above 800 nanometers and practically from 1 micron (1,000 nanometers).

Color

Color is tested by visual observation and in particular by comparison to "Pantone® formula guide solid uncoated" colors. The preferable color is Yellow-bright yellow 600U-601 U-602U according to the Pantone acceptable colors. Minocycline changes color to orange/greenish with oxidation or complexation. These oxidized colors are not desirable. Colors such as 609U/608U/610U are indicative of degradation by the tetracycline antibiotic.

Shakability

Shakability represents the degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non shakable. This property may be of particular importance in cases where shaking is required for affecting proper dispersion of the contents.

Shakability Scoring:

| Shakability | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Centrifugation

Aging by centrifugation:

1. Principle of Test

The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion. The test may be less meaningful for waterless suspensions and compositions comprising a single phase since the suspensions will sediment and as there is not an emulsion the formulations can more readily separate.

2. Procedure
   2.1 Following preparation of the experimental formulation/s, allow to stand at room temperature for 24 h.
   2.2 Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
   2.3 Transfer each mixture to 1.5 mL microtubes. Tap each microtube on the table surface to remove entrapped air bubbles.
   2.4 Place visually balanced microtubes in the centrifuge rotor and operate the centrifuge at one or more of 10,000 rpm for 10 min, 3,000 rpm for 10 min or at 1,000 rpm for 10 min.

Uniformity

Intra-Canister Uniformity

1. Representative product containers are collected, sample test solutions are prepared and the content of the analyte is determined according to standard methods in the art. Variability of content is characterized as percent difference or relative standard deviation, as appropriate, according to the number of samples evaluated.
2. The results ascertain variability or uniformity within a given container in content of analytes (primarily active pharmaceutical ingredients, but also preservatives) taken from different parts of a pressurized canister drug products
3. Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

$$\frac{\text{Difference between content determined in initial \& final portions}}{\text{Mean of content of initial \& final portions}} \times 100$$

and the intra canister uniformity evaluated from the results.

Stock Compositions

Non-limiting examples of how stock solutions are made up with and without API are illustrated. Other stock solutions may be made using the same methodology by simply varying adding or omitting ingredients as would be appreciated by one of the ordinary skills in the art.

EXAMPLES

The present disclosure is described with reference to the following examples. For the purpose of the Examples below it was sufficient to apply a vacuum only at the crimping stage although for long term stability preferably any vacuum should be applied during manufacture as well at a sufficient pressure so that any oxygen remaining in the formulation is virtually negligible. This disclosure is not limited to these examples and experiments. Many variations will suggest themselves and are within the full intended scope of the appended claims.

Two major groups of experiments were performed to find suitable topical formulations comprising either minocycline (minocycline hydrochloride) or doxycycline ("DOX") (doxycycline hyclate or monohydrate).

Table A shows at least some of the components used in formulating minocycline hydrochloride ("MCH") and Table B shows some of the components used in formulating doxycycline hyclate.

TABLE A

Components used in formulating carriers and compositions for Minocycline hydrochloride
MCH

| surfactants | foam adjuvant | emollients | Oils | Anti-greasiness agent |
|---|---|---|---|---|
| Glycerol monostearate | Oleyl alcohol | Cyclomethicone | Light mineral oil | Aluminum Starch Octenylsuccinate (ASOS) |
| Polysorbate 60 | Stearyl alcohol | PPG-15 Stearyl Ether | Hydrogenated Castor Oil | |
| Polysorbate 80 | Myristyl alcohol | Octyldodecanol | | |
| Sucrose distearate | Cocoglycerides | Isohexadecanol | | |
| Steareth 2(Polyoxyl 2 Stearyl Ether) | | Diisopropyl adipate | | |
| Steareth 20(Polyoxyl 20 Stearyl Ether) | | Cetearyl Octanoate | | |
| Steareth | | | | |

TABLE A-continued

Components used in formulating carriers and compositions for Minocycline hydrochloride MCH 21(Polyoxyl 21 Stearyl Ether)
Sorbitan monostearate (Span 60)
Metyl Glucose Sesquistearate
Myrj 52(Polyoxyl 40 stearate)
Myrj 59(Polyoxyl 100 stearate)
Montanov S (cetearyl alcohol and coconut alcohol)
Glyceryl monostearate
Sepigel 305(Polyacryl amide + isoparaffin + Laureth-7)

Full list

Titanium Dioxide
Cyclomethicone
PPG-15 Stearyl Ether
Octyldodecanol
Light mineral oil
Oleyl alcohol
Isohexadecanol
Glycerol monostearate
Diisopropyl adipate
Stearyl alcohol
Myristyl alcohol
Hydrogenated Castor Oil
Polysorbate 60/80
Cetearyl Octanoate/Sucrose distearate
Steareth 20(Polyoxyl 20 Stearyl Ether)
Steareth 2 (Polyoxyl 2 Stearyl Ether)
Aluminum Starch Octenylsuccinate
Cocoglycerides
Sorbitan monostearate (Span 60)
Metyl Glucose Sesquistearate
Myrj 52(Polyoxyl 40 stearate)
Myrj 59(Polyoxyl 100 stearate)
Montanov S(cetearyl alcohol and coconut alcohol)
Carbopol 934
Minocycline HCL
Sepigel 305(Polyacrylamide + isoparaffin + Laureth-7)
Bentone PTM
Bentone VS-5 PC V
Ethocel 7 FP
Ethocel 100 FP
Aerosil
Dry-flo AF
Glyceryl monostearate

TABLE B

Components used in formulating compositions for doxycycline hyclate.

| | DOX | | | |
|---|---|---|---|---|
| surfactants | foam adjuvants | emollients | Oils | Anti-greasiness |
| Glycerol monostearate | Oleyl alcohol | Cyclomethicone | Light Mineral Oil | Aluminum Starch Octenylsuccinate (ASOS) |
| Sucrose Ester HLB 11 | Stearic acid | PPG-15 Stearyl Ether | MCT oil | |
| GMS-PEG 100 Stearate | Stearyl alcohol | Propylene Glycol | | |
| Polysorbate 80 | Myristyl alcohol | Octyldodecanol | | |
| Polysorbate 60 | Cocoglycerides | Glycerol | | |
| Polysorbate 20 | | Diisopropyl adipate | | |
| Sorbitan monostearate | | Cetearyl Octanoate | | |
| Methy Glucose Sesquistearate | | | | |
| PEG 40 Stearate (Myrj 52) | | | | |
| PEG 100 Stearate (Myrj 59) | | | | |
| Hydrogenated Castor Oil | | | | |
| Steareth-2 | | | | |
| Steareth-20 | | | | |
| Steareth-21 | | | | |
| Poloxamer 407(20% gel) | | | | |

Full list

Cyclomethicone
PPG-15 Stearyl Ether
Propylene Glycol
Oleyl alcohol
Cetearyl Octanoate
Octyldodecanol
Light Mineral Oil
Glycerol
Klucel EF
Stearic acid
Stearyl alcohol
Myristyl alcohol
Glycerol monostearate
Sucrose Ester HLB 11
GMS-PEG 100 Stearate
Cocoglycerides
Methocel A4
Xanthan Gum
Polysorbate 80
Polysorbate 60
Polysorbate 20
Sorbitan monostearate
Methy Glucose Sesquistearate
PEG 40 Stearate (Myrj 52)
PEG 100 Stearate (Myrj 59)
Hydrogenated Castor Oil
Steareth-2
Steareth-20
MCT oil
Steareth-21

TABLE B-continued

Components used in formulating compositions for doxycycline hyclate.

| | DOX | | |
|---|---|---|---|
| foam adjuvants | emollients | Oils | Anti-greasiness |

Aluminum Starch octenylsuccinate (AS0S)
Diisopropyl adipate
Poloxamer 407(20% gel)
Dry-Flo AF
Aerosil
Ethocel 7 FP
Doxycycline Hyclate
Doxycycline Monohydrate A list of the chemical constituents of the Brand names of some of the ingredients of the present disclosure, used in some of the formulations of the present disclosure appears in the following "Ingredients Table" Table C.

INGREDIENTS TABLE C

| Name | Brand name |
|---|---|
| PPG-15 Stearyl Ether | Sympatens ASP/150 |
| Octyldodecanol | Eutanol G PH |
| Light mineral oil | Pionier 2076P |
| Cyclomethicone | DC 345 fluid |
| Diisopropyl adipate | Isoadipate |
| Oleyl Alcohol | HD-EUTANOL VPH |
| Glyceryl monostearate | Cutina GMS VPH |
| Stearyl alcohol | Speziol C18 PH |
| Hydrogenated Castor Oil | Cutina HR PH |
| Cetearyl Octanoate | Levitol EHO |
| Polyoxyl 20 stearyl Ether | Brij 78 P |
| Polyoxyl 2 stearyl Ether | Brij 72 |
| Myristyl Alcohol | Speziol C14 |
| Methyl glucose sesquistearate | Tego Care PS |
| Aluminum starch octenylsuccinate (ASOS) | Dry flo Plus |
| Cocoglycerides | Novata A |
| Doxycycline Hyclate | Doxycycline Hyclate |
| Propellant | PIB 1681 |

EXAMPLES

Example 1

Foamable Carriers for Doxycycline Hyclate/Monohydrate

Foamable carriers were prepared as follows:
Prefoam formulations (PFFs) were prepared according to a typical protocol (exemplified for DOX-026, See Section "General Manufacturing Procedure for DOX formulations" hereinbelow). Numerous changes were made to the composition in order to find a PFF which, after addition of the propellant and expelled from a pressurized canister, has the following property:
 a foam quality of at least good up to excellent;
 and at least one of the following properties:
 specific gravity in the range of about 0.02 gr/mL to about 0.5 gr/mL;
 a foam texture of a very fine creamy foam consistency to a fine bubble structure consistency;
 a sustainability of more than 95% for at least one minute upon release thereof to a surface from an aerosol can;
 less than 20% sedimentation following ten minutes of centrifugation at 3000 g; and
 compatibility with said at least one unstable active agent, wherein said compatibility is defined as less than 20% oxidation of said at least one unstable active agent.

As can be seen in Table 1, the DOX-001 formulation was only FG (fairly good) and therefore did not meet the quality standard. Experimental steps were performed, including:
 other additives to improve foam quality
 change of surfactants and polymers to improve foam quality.

Thus, as can be seen in Table 1, the foam quality was improved from fairly good to good from batch DOX-001 to DOX-017 (see Table 22 for additional formulations).

TABLE 1

Development of a foamable carrier for doxycycline hyclate.

| | Lot: | | | |
|---|---|---|---|---|
| | DOX-001 % w/w | DOX-010 % w/w | DOX-013 % w/w | DOX-017 % w/w |
| Cyclomethicone | 1.49 | 2.00 | 3.00 | 3.00 |
| PPG-15 Stearyl Ether | 9.90 | 8.00 | 15.00 | 15.00 |
| Propylene Glycol | 58.91 | | | |
| Oleyl alcohol | 9.90 | 9.70 | 10.00 | 10.00 |
| Cetearyl Octanoate | | | 3.00 | 2.00 |
| Octyldodecanol | | 9.70 | 12.00 | 12.00 |
| Light Mineral Oil | | | 17.84 | 16.84 |
| Glycerol | | 51.20 | | |
| Stearic acid | 1.98 | | | |
| Stearyl alcohol | | 1.00 | 4.00 | 6.00 |
| Myristyl alcohol | 1.98 | | 1.00 | 2.50 |
| GMS (glycerol monostearate) | | 2.00 | 4.00 | 6.00 |
| Sucrose Ester HLB 11 | | 2.00 | | |
| Cocoglycerides | | | | 6.00 |
| Polysorbate 20 | | 0.90 | | |
| Methy Glucose Sesquistearate | | | 3.00 | |
| Hydrogenated Castor Oil | | | 1.50 | 3.50 |
| Steareth-2 | 4.95 | 1.50 | 5.00 | |
| Steareth-20 | | | 2.50 | |
| Aluminum Starch | | | 10.00 | 10.00 |

TABLE 1-continued

Development of a foamable carrier for doxycycline hyclate.

| | Lot: | | | |
|---|---|---|---|---|
| | DOX-001 % w/w | DOX-010 % w/w | DOX-013 % w/w | DOX-017 % w/w |
| Octenylsuccinate (ASOS) | | | | |
| Diisopropyl adipate | 9.90 | 9.00 | 8.00 | 8.00 |
| Doxycycline Hyclate | 0.99 | | 1.16 | 1.16 |
| Control | 100.00 | 100.00 | 100.00 | 100.00 |
| Propellant 1681 | 8.00 | 8.00 | 8.00 | 10.00 |
| Control II | 108.00 | 108.00 | 108.00 | 110.00 |
| Date manufacture | Jan. 23 | Feb. 15 | May 8 | May 21 |
| Foam quality | FG separated at room temperature | FG | G | G |
| Shakability | NT | 2 | 2 | 2 |
| Collapse Time (s) | NT | NT | 150 | 240 |
| Hardness(g) | NT | NT | 14.23 | 23.05 |
| Viscosity (cPs) 10 RPM | NT | NT | 1213 | 4700 |
| Density (g/ml) | NT | NT | Not tested | 0.168 |

FG—fairly good foam quality
G—Good foam quality
NT—not tested due to fairly good foam quality Comments: It was observed that the combination of two surfactants glycerol monostearate and methyl glucose sesquistearate with foam adjuvants provided an improvement in foam quality. DOX-013 and DOX-017 showed good foam quality. In contrast fairly good quality was observed in formulations DOX-001 and DOX-010. However, formulations 13 and 17 when subject to centrifugation at 3000 rpm or 10,000 rpm for 10 mins resulted in sedimentation of the suspension and some separation.

Formulations DOX-001, DOX-017, DOX-010 and DOX-013 were prepared by heating of oils to 65-70° C. and addition of surfactants by mixing. The mixture was cooled down to 55-60° C. and emollients were added by thorough mixing. Aluminum Starch Octenylsuccinate was added to DOX-010 and DOX-013 at 40° C. After homogenization all the formulations were cooled down to the room temperature. API was added with stirring when the temperature fell below 30° C.

Tables 2 to 4 shows further development of foamable carrier for doxycycline, in which the concentrations of surface active agents and the types of surface active agents were changed.

TABLE 2

Further Development of a foamable carrier for doxycycline hyclate and doxycycline monohydrate

| | Lot: | | | | |
|---|---|---|---|---|---|
| | DOX-022 % w/w | DOX-025 % w/w | DOX-026 % w/w | DOX-027 % w/w | DOX-033 % w/w |
| Cyclomethicone | 3.00 | 3.00 | 3.00 | 3.00 | 3.00 |
| PPG-15 Stearyl Ether | 15.00 | 15.00 | 15.00 | 15.00 | 15.00 |
| Oleyl alcohol | 10.00 | 10.00 | 10.00 | 10.00 | NA |
| Cetearyl Octanoate | NA | NA | 2.00 | NA | NA |
| Octyldodecanol | 12.00 | 12.00 | 12.00 | 12.00 | 12.00 |
| Light Mineral Oil | 26.33 | 28.96 | 17.84 | 18.00 | 54.46 |
| Stearyl alcohol | 4.00 | 4.00 | 4.00 | 6.00 | 6.00 |
| Myristyl alcohol | 1.00 | 1.00 | 1.00 | 2.50 | 2.50 |
| Glycerol Monostearate | 4.00 | 3.00 | 4.00 | 6.00 | 6.00 |
| MCT OIL | NA | NA | NA | 6.00 | NA |
| Cocoglycerides | 2.00 | NA | NA | NA | NA |
| Methy Glucose Sesquistearate | NA | NA | 3.00 | NA | NA |
| PEG 100 Stearate (Myrj 59) | NA | 0.50 | NA | NA | NA |
| Hydrogenated Castor Oil | 3.50 | 3.50 | 1.50 | 3.50 | NA |
| Steareth-2 | NA | NA | 5.00 | NA | NA |
| Steareth-20 | NA | NA | 2.50 | NA | NA |
| Aluminum Starch Octylsuccinate | 10.00 | 10.00 | 10.00 | 10.00 | NA |
| Diisopropyl adipate | 8.00 | 8.00 | 8.00 | 8.00 | NA |
| Doxycycline Hyclate | 1.17 | NA | 1.16 | 1.16 | NA |
| Doxycycline Monohydrate | NA | 1.04 | NA | NA | 1.04 |
| Control | 100.00 | 100.00 | 100.00 | 100.00 | 100.00 |
| Propellant 1681 | 12.00 | 12.00 | 12.00 | 12.00 | 12.00 |
| Control II | 112.00 | 112.00 | 112.00 | 112.00 | 112.00 |
| Date manufacture | 18-June-2007 | 20-June-2007 | 31-July-2007 | 01-August-2007 | 12-September-2007 |

TABLE 2-continued

Further Development of a foamable carrier for doxycycline hyclate and doxycycline monohydrate

| | Lot: | | | | |
|---|---|---|---|---|---|
| | DOX-022 % w/w | DOX-025 % w/w | DOX-026 % w/w | DOX-027 % w/w | DOX-033 % w/w |
| Foam quality | G | FG to G | FG to G | FG to G | G |
| Shakability | 1 | 2 | 1 | 1 | 2 |
| Expansion Time(sec) | Not tested | 97 | Not tested | Not tested | Not tested |
| Collapse Time (sec) | >300 | 150 | 150 | 150 | 240 |
| Hardness (g) | 24.59 | 10.92 | Not tested | Not tested | 18.46 |
| Viscosity (cPs) 10 RPM tested on PFF only | 6789 | 10710 | 10710 | not tested | 1051 |
| Density(g/ml) | 0.193 | 0.079 | 0.419 | 0.142 | 0.168 |
| Assay at T-0 (% w/w) | | | | | |
| | 0.77-PFF 0.96-foam | 0.82-PFF 0.96-foam | Not tested | Not tested | 0.92-PFF 0.94-foam |
| Assay after 3 months of storage | | | | | |
| 5° C. | 0.85-foam | 0.78 | Not tested | Not tested | 0.89 |
| 25° C. | 0.87-foam | 0.70 | Not tested | Not tested | 0.88 |
| 30° C. | 0.90-foam | 0.68 | Not tested | Not tested | 0.89 |
| 40° C. | 0.82-foam | 0.61 | Not tested | Not tested | 0.87 |

NA—not applicable
G—good
FG—fairly good
PFF—Pre foam formulation

Addition of cocoglycerides to formulation DOX-022 may account for the improved foam quality compared to DOX-025 formulation where surfactant PEG 100 stearate was incorporated instead of cocoglycerides.

Exclusion of cocoglycerides and incroporation of steareth-2, steareth-20 and methyl glucose sesquistearate to DOX-026 did not result in an improvement in the foam quality of the formulation.

The number of ingredients were significantly reduced in formulation DOX-033. This formulation revealed good foam quality.

Formulation DOX-033 appears to be chemically stable during 3 months of storage at different temperatures.

Complex formulations with a high array of ingredients (DOX-022, DOX-025, DOX-26 and DOX-027) were found to be chemically unstable.

General Manufacturing Procedures for DOX Formulations:

In order to prepare an agent free pharmaceutical composition and a pharmaceutical composition comprising an agent, the following steps were followed.

Preparation of a Pre-foam formulation (PFF)
Milling of Doxycycline Hyclate/Monohydrate. The range of the particle size is minimum 2.2 μm-maximum 41 μm.

Addition of Doxycycline Hyclate/Monohydrate
Formulation DOX-026 PFF preparation (see Table 3 for further process details)

Heat up the Light mineral oil to 70° C. Add Oleyl alcohol, Octyldodecanol

Add Hydrogenated Castor Oil under mixing until completely dissolution. Add Myristyl alcohol, Cetearyl Octanoate under mixing.

Add Glyceryl Monostearate, Stearyl alcohol, Steareth-20, Steareth-2, Cyclomethicone and Methyl Glucose Sesquistearate under mixing.

Cool down to 60° C., add the PPG-15 Stearyl Ether, Mix till the ingredients are completely dissolved.

Add Diisopropyladipate under mixing.

Cool down to 40° C., add the Aluminum starch Octenylsuccinate under mixing until complete dispersion.

Cool down to RT.

Mill Doxycycline Hyclate by mortar. This procedure is performed according to MSDS of antibiotic.

Add the Doxycycline Hyclate, mix until homogenous suspension.

TABLE 3

Production Procedure for DOX-026

| | | Required | | |
|---|---|---|---|---|
| | Procedure | Time (min) | Temp (° C.) | Mixing rate (rpm) |
| PFF (pre-foam formulation) preparation | Heating of Light Mineral Oil, Oleyl alcohol, Octyldodecanol | 20 | 70 | 400-600 |
| | Addition of Hydrogenated Castor Oil, Cetearyl Octanoate and Myristyl alcohol | 10-15 | 70 | 400-600 |
| | Addition of Glyceryl monostearate | 10-15 | 70 | 400-600 |

TABLE 3-continued

Production Procedure for DOX-026

|  | Procedure | Required | | |
|---|---|---|---|---|
|  |  | Time (min) | Temp (° C.) | Mixing rate (rpm) |
|  | Stearyl alcohol, Steareth 20, Steareth 2, Methyl Glucose Sesquistearate, Cyclomethicone |  |  |  |
|  | Addition of PPG-15 Stearyl ether | 5-10 | 60 | 400-600 |
|  | Addition of Di-isopropyl adipate and | 15-20 | 70 | 400-600 |
|  | Cooling down and add Aluminum Starch Octenylsuccinate | 10-20 | 40 | 400-600 |
| Addition of Doxycycline Hyclate | Milling of Doxycycline Hyclate by mortar | n/a | r.t. | n/a |
|  | Addition of Doxycycline Hyclate to the PFF | 5-10 | r.t. | 5500-6000 |

One example of the canisters and closures used in this disclosure are presented in Table 4.

TABLE 4

Canister and Packaging of DOX-026

| Bottle kind/closure system | Supplier, supplier address and Product number |
|---|---|
| Pressurized Nussbaum monoblock aluminum canisters 35 × 70 mm, phenol-epoxy lacquer* | Weiss unberdruck NG 35.070Foamix Nussbaum AG |
| Valve | 0064061, Seaquist, France |
| Actutor | 1010274 Seaquist, France |

Experimental Procedure for Batch No. DOX-033

Formulation DOX-033 contains minimal excipients composition and another salt of Doxycycline was used—Doxycycline Monohydrate. In addition, the propellant concentration raised to 12% instead of 8% in previous formulations (see DOX-26 and 27).

TABLE 5

Ingredients for batch DOX-033

| Name | Brand name | Supplier and Address |
|---|---|---|
| PPG-15 Stearyl Ether | Sympatens ASP/150 | Kolb |
| Octyldodecanol | Eutanol G PH | Cognis |
| Light mineral oil | Pionier 2076P | Hansen & Rosenthal |
| Cyclomethicone | 5 NF | DOW |
| Glyceryl monostearate | Cutina GMS VPH | Cognis |
| Stearyl alcohol | Speziol C18 PH | Cognis |
| Myristyl Alcohol | Speziol C14 | Cognis |
| Doxycycline Monohydrate | Doxycycline Monohydrate |  |
| Propellant 1681 |  |  |

Manufacturing Procedure for DOX-033

Step 1-a: Preparation of PFF

Heat up the Light mineral oil to 70° C. Add Octyldodecanol.

Add Myristyl alcohol.

Add Glyceryl Monostearate and Stearyl alcohol under mixing.

Cool down to 60° C., add the PPG-15 Stearyl Ether, Cyclomethicone. Mix till the ingredients are completely dissolved.

Cool down to 30° C.

Step 2: Addition of Doxycycline Monohydrate to Formulation

Milled Doxycycline Monohydrate by mortar. This procedure is performed according to MSDS of antibiotic.

Add the Doxycycline Monohydrate, mix until homogenous suspension.

Cool down to RT.

Production Procedure Record for DOX-033

TABLE 6

Process Details for batch DOX-033

|  | Procedure | Required | | |
|---|---|---|---|---|
|  |  | Time (min) | Temp (° C.) | Mixing rate (rpm) |
| PFF (pre-foam formulation) preparation | Heating of Light Mineral Oil & Octyldodecanol | 20 | 70 | 400-600 |
|  | Addition Myristyl alcohol | 10-15 | 70 | 400-600 |
|  | Addition of Glyceryl monostearate and Stearyl alcohol | 10-15 | 70 | 400-600 |
|  | Addition of PPG-15 Stearyl ether, & | 5-10 | 60 | 400-600 |

TABLE 6-continued

Process Details for batch DOX-033

| | | | Required | |
|---|---|---|---|---|
| | Procedure | Time (min) | Temp (° C.) | Mixing rate (rpm) |
| | Cyclomethicone Cooling down | 10-20 | 40 | 400-600 |
| Addition of Doxycycline Monohydrate | Grinding of Doxycycline Monohydrate by mortar | n/a | RT | n/a |
| | Addition of Doxycycline Monohydrate to the PFF | 5-10 | 40- RT | 5500-6000 | n/a—not applicable
RT—room temperature

Formulation DOX-033 was filled in following packaging configurations:
1. Nussbaum aluminum monoblock canisters, 30±5 g of PFF, crimped and pressurized with 12% propellant.
2. Amber glass bottles filled with 20±5 g of PFF under nitrogen environment and without nitrogen.
3. Canisters were stored in upright or inverted positions for 3 weeks.

Without wishing to be bound to any theory, the formulations produced appeared to be suspensions of solid surfactants in an oily phase. Of all the formulations DOX-001-033, DOX-033 was found to be the most stable. The concentration of doxycycline was monitored over time. There was originally 1.04 g of doxycycline in the composition. Table 7 shows the concentration measured as a function of time and storage conditions:

TABLE 7

Concentration of doxycycline monohydrate in DOX-033 formulation measured over time at different storage temperatures.

| Foam Assay (% w/w) | Specifications | 5° C. Up | 5° C. inv | 25° C. Up | 25° C. inv | 30° C. up | 30° C. inv | 40° C. up | 40° C. inv |
|---|---|---|---|---|---|---|---|---|---|
| T-0 | Labeled conc.-1.0% Range: 0.90-1.10 (90.0-110.0%) | 0.93 | 0.93 | 0.93 | 0.93 | 0.93 | 0.93 | 0.93 | 0.93 |
| 3 weeks storage | labeled conc.- 1.0% Range: 0.90-1.10 (90.0-110.0%) | 0.89 | 0.88 | 0.88 | 0.88 | 0.89 | 0.88 | 0.86 | 0.86 |

Up = upright position
Inv = inverted position

Example 2

Foamable Carriers for Minocycline

A series of experiments was performed to find suitable formulations of foamable carriers for minocycline. Similar steps were taken to those described with respect to Table 1, including:
- other additives to improve foam quality
- change of surfactants and polymers to improve foam quality
- use of unstable agent compatible materials per Table 19

Some of the results appear in Tables 8-11 hereinbelow.

TABLE 8

Development of a foamable carrier for minocycline

| | Lot: MCH-001 % w/w | Lot: MCH-022 % w/w |
|---|---|---|
| Titanium Dioxide | | 2.00 |
| CyclomethiconeCyclomethicone (DC 345 fluid) | | 3.00 |
| PPG-15 Stearyl Ether | 15.00 | 15.00 |
| Octyldodecanol | 12.00 | 12.00 |
| Light mineral oil | 31.93 | 17.93 |
| Oleyl alcohol | 10.00 | 10.00 |
| Glycerol monostearate | 4.00 | 4.00 |
| Diisopropyl adipate | 8.00 | 8.00 |

TABLE 8-continued

Development of a foamable carrier for minocycline

| | Lot: MCH-001 % w/w | Lot: MCH-022 % w/w |
|---|---|---|
| Stearyl alcohol | 4.00 | 4.00 |
| Myristyl alcohol | / | 1.00 |
| Hydrogenated Castor Oil | / | 1.50 |
| Cetearyl Octanoate/Sucrose distearate | 1.50 | 2.00 |
| Polyoxyl 20 Stearyl Ether | 2.50 | 2.50 |
| Polyoxyl 2 Stearyl Ether | 5.00 | 5.00 |
| Aluminum Starch Octenylsuccinate | 5.00 | 10.00 |

TABLE 8-continued

Development of a foamable carrier for minocycline

|  | Lot: | |
| --- | --- | --- |
|  | MCH-001 % w/w | MCH-022 % w/w |
| Metyl Glucose Sesquistearate | / | 3.00 |
| Minocycline HCL | 1.07 | 1.07 |
| Control | 98.93 | 100.00 |
| Propellant | 12.00 | 12.00 |
| Control II | 112.00 | 112.00 |
| Results | | |
| Foam quality | FG | G |
| Viscosity (cPs) 10 RPM | 844 | 4787 |
| Density | N.A | 0.136 |
| Shakability | Good | Good |

FG—Fairly good foam quality
G—good quality

The effect of selected factors on the formulation of a 1% Minocycline HCl foam product and its properties were evaluated.
1. Cyclomethicone: to impart a non-greasy skin feeling.
2. Titanium dioxide: to give a lighter foam color and to impart a sunscreen effect (MCH causes yellow discoloration of the skin and increased photosensitivity).
3. Different proportions of oils as listed below.

Formulation MCH-022 is one of the rational design matrix array.

Formulations were prepared by heating the oils an to 65-70° C. following by addition of surfactants/adjuvant. Minocycline HCl was incorporated at 30° C.

Minocycline HCl is a solid and is presented as a solid suspension in the formulations therefore preferably one or more agents, which can be added that are capable of providing a uniform suspension should be identified.

The effect of Sepigel 305 (polyacrylamide/isoparaffin/Laureth-7) was examined in formulation MCH-087 with and without API.

Addition of Minocycline HCl at concentration of 1.18% w/w changes the physical and chemical properties of formulation.

PFF was packed in Nussbaum aluminum monoblock canisters and Plastic-coated, pressurizable glass aerosol container (LM Wheaton, M-937F, supplied as GK-500 by Aero-Tech Laboratory Equipment

TABLE 9

Development of a foamable carrier for minocycline

| Composition | MCH-087-(Placebo) | MCH-087-071021 |
| --- | --- | --- |
| PPG-15 Stearyl Ether | 15.00 | 15.00 |
| Octyldodecanol | 12.00 | 12.00 |
| Light mineral oil | 50.50 | 48.99 |
| Polyacrylamide/Isoparaffin/Laureth-4 (Sepigel 305) | 5.00 | 5.00 |
| Cyclomethicone | 3.00 | 3.00 |
| Glyceryl monostearate | 6.00 | 6.00 |
| Stearyl alcohol | 6.00 | 6.00 |
| Myristyl alcohol | 2.50 | 2.50 |
| Minocycline Hydrochloride | NA | 1.26 |
| Control: | 100.00 | 100.00 |

TABLE 9-continued

Development of a foamable carrier for minocycline

| Composition | MCH-087-(Placebo) | MCH-087-071021 |
| --- | --- | --- |
| Propellant 1681 | 12.00 | 12.00 |
| Homogeneity test at pressurized glass aerosol container after 1 day storage at 25° C. | separation <5% spillable | homogenous, viscous spillable |
| Homogeneity test at pressurized glass aerosol containers after 1 month storage at 25° C. | separation <5% spillable | homogenous, viscous spillable, shakable: |
| Viscosity (cPs) | 847.82 | 1045.75 |
| Foam quality | G | G |
| Shakability | 2 | 2 |

NA—not applicable
G—good foam quality

Manufacturing Procedure for MCH-087

Step 1-a: Preparation of Light Mineral Oil Mixture

Heat up the Light mineral oil to 70-75° C. Add Octyldodecanol.

Add Myristyl alcohol with mixing.

Add Glyceryl Monostearate and Stearyl alcohol under mixing.

Step 1-b: Premix of Sepigel 305 in Cyclomethicone

Heat the cyclomethicone to 70-75° C. Introduce slowly by portions the Sepigel 305 at 75° C. with mixing.

Step 1-c: Incorporation of Sepigel 305 into the Oil Mixture

Incorporate slowly the Step 1-b product into the Step 1-a mixture at 75° C. at least.

Step 1-d. Addition of PPG-15 Stearyl Ether

Cool down the mixture from Step 1-a to 60° C., add the PPG-15 Stearyl Ether. Mix till the ingredients are completely dissolved.

Cool down to 30° C.

Add Minocycline HCl by continuous mixing.

Formulation was filled in Nussbaum aluminum monoblock canisters, 30±5 g of PFF, crimped and pressurized with 12% propellant.

TABLE 10

Chemical Stability of MCH-087 formulation stored in canisters at upright and inverted positions after three weeks storage at 25° C. and 40° C.

|  | T-0 | | 3 weeks stability 25° C. | | 3 weeks stability 40° C. | |
| --- | --- | --- | --- | --- | --- | --- |
|  | PFF (pre-foam formulation | Foam | Up | inv | up | inv |
| Assay (% w/w) of labeled conc-1.0% ± 0.1 | 1.20 | 1.08 | 1.17 | 1.15 | 1.09 | 1.03 |

Up = upright
Inv = inverted

Formulation was stable following the storage at 40° C. for 3 weeks.

Formulations MCH-075 and MCH-076 contain minimal excipients in compositions. Corn starch derivative aluminum free (Dry-Flo® AF) was added to formulation MCH-105 to reduce the tackiness. Formulation MCH-109 contains Octyldodecanol instead of PPG-15 Stearyl Ether but did not achieve any reasonable foam quality such as MCH-075.

TABLE 11

Development of additional foamable carrier for minocycline

| Composition | MCH-072 | MCH-075 | MCH-076 | MCH-105 | MCH-107 |
|---|---|---|---|---|---|
| PPG-15 Stearyl Ether | 15.00 | 42.21 | 42.21 | 15.00 | 15.00 |
| Octyldodecanol | 12.00 | NA | NA | 12.00 | 12.00 |
| Light mineral oil | 54.32 | 42.21 | 42.21 | 49.83 | 49.33 |
| Polyacrylamide/Isoparaffin/Laureth-4 (Sepigel 305) | NA | NA | NA | 5.00 | 3.00 |
| Cyclomethicone | 3.00 | NA | NA | 3.00 | 3.00 |
| Glyceryl monostearate | 6.00 | 6.00 | 6.00 | 6.00 | 6.00 |
| Stearyl alcohol | 6.00 | 6.00 | 6.00 | NA | NA |
| Myristyl alcohol | 2.50 | NA | NA | NA | 2.50 |
| Cocoglycerides | NA | 2.50 | NA | NA | NA |
| Corn starch derivative (Dry-Flo ® AF) | NA | NA | NA | 8.00 | 8.00 |
| Minocycline Hydrochloride | 1.18 | 1.18 | 1.18 | 1.18 | 1.18 |
| Control: | 100.00 | 100.00 | 100.00 | 100.00 | 100.00 |
| Propellant 1681 | 12.00 | 12.00 | 12.00 | 12.00 | 12.00 |
| Foam quality | Good | Good | Good | Good | Good |
| Shakability | 2 | 2 | 2 | 2 | 2 |

NA—not applicable

Comment: Formulation MCH-75 was repeated using Octyldodecanol instead of PPG-15 Stearyl Ether but did not achieve a reasonable foam quality Example 3

Examples of Compatibility Testing

Part A Minocycline

The physicochemical properties of minocycline HCl are similar to those of other tetracycline antibiotics with the exception of differences resulting from the presence of a second dimethylamino group.

General properties of minocycline HCl:
1. Slightly hygroscopic, yellow crystalline odorless powder with a slight bitter taste.
2. Relatively stable as a solid powder, however, undergoes degradation in aqueous solutions.
3. The major degradative pathways are carbon-4 epimerization and oxidative processes. Since the oxidized products are frequently dark in color, objectionable color changes are often encountered before the loss of activity becomes appreciable. Epimerization continues until equilibrium between minocycline and its epimer is achieved.

It is known from the literature that oxidation of tetracycline antibiotics can occur at any pH.

The compatibility tests were made of a selection of a wide range of different types of excipients as can be seen in Table 12 below. For convenience the excipients were divided into four different groups (I-IV).

Different compositions of hydrophilic and hydrophobic solvents containing minocycline HCl were prepared by weighing the antibiotic in a glass vial and shaking overnight with each solvent investigated (Group I and II).

Mixtures of Minocycline HCl with solid excipients like titanium dioxide, stearyl alcohol, myristyl alcohol etc were prepared by suspending Minocycline HCl in oil with stirring and then adding the solid ingredient as a powder with stirring at room temperature (Group III an IV).

Oxidation of minocycline after the storage at various temperatures was detected by color change. Assay for content of the active pharmaceutical ingredient (API) and degradation product (4-epiminocycline) was determined in some samples.

The major degradative pathways for Minocycline are carbon-4 epimerization and oxidative processes. Minocycline is relatively stable as a solid powder, however, it undergoes degradation in aqueous solutions. Many different excipients cause the Minocycline oxidation (see the incompatibility tables 13a, 13b, 13c and 13d herein). Epimerization continues until equilibrium between minocycline and its epimer is achieved.

Since the oxidized products are frequently dark in color, objectionable color changes are often encountered before the loss of activity becomes appreciable. The analytical method doesn't detect the "oxidative Minocycline". It should be noted that an oxidized product is evident by color change. It is not necessary to detect it chromatographically, but a low Minocycline assay result can be seen compared to the zero time value (T−0) when this process happens inside the canister. At higher temperatures (30° C., 40° C., 50° C.) the oxidation process is even more noticeable. Epimerization levels are around 2-5% of API assay.

Without being bound to any theory, it seems that water residues in hydrophilic vehicles like propylene glycol, polyethylene glycol 200 and 400 (PEG 200 and PEG 400 respectively) and glycerol are responsible for fast oxidation and epimerization of Minocycline.

A special procedure for drying of water residues was developed. Magnesium Sulphate was added to the glass beaker filled with one of the hydrophilic vehicles. The mixture was stirred during overnight and centrifuged the following morning. Clear supernatant was collected in a separate vessel and stored in a dessicator.

The following were tested using the above procedure: mixtures of Minocycline with PEG 200, PEG 400, glycerol, propylene glycol, polyethylene glycol. It was observed that Minocycline HCL oxidized quickly after dissolution in all the different "dryed" hydrophilic vehicles ("dryed by the Magnesium Sulfate procedure) that were tested. It was concluded that pre drying the excipients did not help to prevent rapid breakdown and therefore the cause must be some other reason.

A series of experiments were performed to evaluate which mixture of components/ingredients were compatible or incompatible with minocycline. Each component or combinations of components were mixed with either 1.1% or 2.2% Minocycline HCl. The glass vials containing the formulations were wrapped in aluminum—and were subjected to a range of temperatures 25° C.; 30° C.; 40° C.; 50 C; for between one week to about 3 weeks. The results of these experiments are shown in Table 13a to 13e. The best results are shown as "compatible no oxidation". The results indicate that these components on their own can be used in formulations with minocycline.

TABLE 13a

Results of Group I Compatibility tests

Mixtures with 2.2% of Minocycline HCl stored for 10 days at 50° C.
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| Visual inspection | bright yellow mixture | bright yellow mixture | bright yellow mixture | bright yellow mixture | dark brown solution | orange brown solution | orange brown solution | orange brown solution | bright yellow mixture | bright yellow solution |
| Compatibility Results | compat. no oxidation | compat. no oxidation | compat. no oxidation | compat. no oxidation | non compat.. Oxidation | non compat. oxidation | non compat. oxidation | non compat. oxidation | compat. no oxidation | compat no oxidation |

Notes and abbreviations:
compat. = compatibility;

TABLE 13b

Results of Group I Compatibility tests

Mixtures with 2.2% of Minocycline HCl stored for 10 days at 50° C.
Ingredients

| Group I | Cetearyl octanoate | Hexylene glycol | Butylene glycol | Sorbitan Monolaurate | Dimethyl Isosorbide |
|---|---|---|---|---|---|
| Visual inspection Compatibility Results | bright yellow mixture compat. no oxidation | bright orange mixture Non compat. oxidation | brown orange solution Non compat. oxidation | brownish orange mixture Non compat. oxidation | brownish yellow mixture Non compat.. oxidation |

TABLE 13c

Results of Group II Compatibility tests

Mixtures with 1.1% of Minocycline HCl after 10 days storage at 40° C.
Ingredients

| Group II | Time points | Ethanol 95% | Ethanol 95% with BHT | Ethanol 95% with BHT and Ascorbic acid | Propylene glycol with ascorbic acid and Vit E | PEG 200 with ascorbic acid and Vit E | Isostearic Acid |
|---|---|---|---|---|---|---|---|
| Minocycline Assay (% w/w) | T-0 | 0.97 | 0.97 | 0.91 | 0.81 | 0.74 | NP |
|  | 10 days at 40° C. | 0.52 | 0.52 | 0.07 | 0.13 | 0.22 |  |
| 4-epiminocycline Assay (% w/w) | T-0 | 0.021 | 0.021 | 0.48 | 0.47 | 0.44 | NP |
|  | 10 days at 40° C. | 0.39 | 0.39 | 0.40 | 0.38 | 0.36 |  |
| Visual inspection | 10 days at 40° C. | Bright orange solution | Bright orange solution | Bright orange solution. | Bright orange solution | Bright orange solution | Orange solution |
| Compatibility Results |  | Non compatible Oxidation | Non compatible Oxidation | Non compatible Oxidation | Non compatible Oxidation | Non compatible Oxidation | Non compatible Oxidation |

BHT—butylated hydroxytolyene;
Vit E—vitamin E

TABLE 13d

Results of Group III Compatibility tests

| Group III Mixture composition | | | T-0 | 25° C. | 30° C. | 40° C. |
|---|---|---|---|---|---|---|
| | | | Assay (% w/w) of Minocycline and 4-epiminocycline following three weeks storage | | | |
| PPG-15 SE; Octyldodec; Mineral oil | | Minocycline | 0.95 | 0.95 | 0.93 | 0.94 |
| | | 4-Epiminocycline | 0.018 | 0.016 | 0.014 | 0.023 |
| | Visual inspection | | yellow mixture | yellow mixture | yellow mixture | yellow mix |
| | Compatibility | | compatible | compatible | compatible | compatible |
| | Results | | no oxidation | no oxidation | no oxidation | no oxidation |
| PPG-15 SE; Octyldodec; Mineral oil + oleyl alcohol | | Minocycline | 0.95 | 0.90 | 0.97 | 0.82 |
| | | 4-Epiminocycline | 0.020 | 0.021 | 0.015 | 0.023 |
| | Visual inspection | | yellow mixture | yellow mixture | yellow mixture | yellow mix |
| | Compatibility | | compatible | compatible | compatible | Reduction of assay |
| | Results | | no oxidation | no oxidation | no oxidation | |
| PPG-15 SE; Octyldodec; Mineral oil + oleyl alcohol + Brij 20 and Brij 2 | | Minocycline | 0.93 | 0.86 | 0.99 | 0.64 |
| | | 4-Epiminocycline | 0.048 | 0.045 | 0.040 | 0.037 |
| | Visual inspection | | yellow mixture | brownish orange mixture | brownish orange mixture | Brown mixture |
| | Compatibility | | compatible | non compatible | non compatible | non compatible |
| | Results | | no oxidation | oxidation | oxidation | oxidation |
| PPG-15 SE; Mineral oil + ASOS | | Minocycline | 1.06 | 0.99 | 1.02 | 1.01 |
| | | 4-Epiminocycline | 0.01 | <0.01 | <0.01 | <0.01 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |
| PPG-15 SE; Octyldodec; MGSS | | Minocycline | 0.90 | 0.80 | 0.80 | 0.55 |
| | | 4-Epiminocycline | 0.120 | 0.121 | 0.06 | 0.080 |
| | Visual inspection | | yellowish orange mixture | brownish orange mixture | Brown mixture | Black mixture |
| | Compatibility | | non compatible | non compatible | non compatible | non compatible |
| | Results | | oxidation | oxidation | oxidation | oxidation |
| PPG-15 SE; Octyldodec; DISPA | | Minocycline | 0.94 | 1.02 | 0.97 | 0.98 |
| | | 4-Epiminocycline | 0.026 | 0.034 | 0.012 | 0.017 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |
| PPG-15 SE; Octyldodec; cetearyl octanoate | | Minocycline | 0.83 | 0.80 | 0.80 | 0.79 |
| | | 4-Epiminocycline | 0.028 | 0.014 | 0.012 | 0.018 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |
| PPG-15 SE; Octyldodec; cyclomethicone | | Minocycline | 0.98 | 0.90 | 0.92 | 0.92 |
| | | 4-Epiminocycline | 0.030 | 0.034 | 0.015 | 0.034 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |
| Light mineral oil; Hydrog. castor oil + Stearyl/myristyl alcohol | | Minocycline | 0.95 | 0.96 | 1.03 | 1.07 |
| | | 4-Epiminocycline | 0.031 | 0.036 | 0.015 | 0.033 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |
| Light mineral oil; titanium dioxide | | Minocycline | 0.97 | 0.99 | 1.07 | 1.16 |
| | | 4-Epiminocycline | 0.031 | 0.016 | 0.017 | 0.022 |
| | Visual inspection | | bright yellow mixture | bright yellow mixture | bright yellow mixture | bright yellow mixture |
| | Compatibility | | compatible | compatible | compatible | compatible |
| | Results | | no oxidation | no oxidation | no oxidation | no oxidation |

Notes and abbreviations:
PPG-15 SE.—Polypropylene Glycol Stearyl Ether
Octyldodec.—octyldodecanol
ASOS—Aluminum Starch Octenylsuccinate
MGSS—Methyl Glucose Sesquistearate
DISPA—Diisopropyl adipate
Hydrog. castor oil—Hydrogenated castor oil
Mixture- the light yellow liquid supernant with powdered sediment of antibiotic TABLE 13e Results of Group IV Compatibility tests

| Group IV Mixture composition | | Assay (% w/w) of Minocycline and 4-epiminocycline following one week storage | |
|---|---|---|---|
| | | 25° C. | 40° C. |
| PPG-15 SE; Octyldodec; PEG 40 Stearate | Minocycline | 0.98 | 0.92 |
| | 4-Epiminocycline | 0.04 | 0.04 |
| | Visual inspection Compatibility Results | Yellow mixture compatible no oxidation | Yellow mixture compatible no oxidation |
| PPG-15 SE; Octyldodec; PEG 100 Stearate | Minocycline | 1.04 | 1.02 |
| | 4-Epiminocycline | 0.03 | 0.03 |
| | Visual inspection Compatibility Results | Yellow mixture compatible no oxidation | Yellow mixture compatible no oxidation |
| PPG-15 SE; Octyldodec; Sorbitan Monostearate | Minocycline | 0.96 | 1.10 |
| | 4-Epiminocycline | 0.08 | 0.12 |
| | Visual inspection Compatibility Results | Yellow mixture compatible no oxidation | Yellow mixture compatible no oxidation |
| PPG-15 SE; Octyldodec; Cocoglycerides | Minocycline | 0.91 | 1.01 |
| | 4-Epiminocycline | 0.01 | 0.02 |
| | Visual inspection Compatibility Results | Yellow mixture compatible no oxidation | Yellow mixture compatible no oxidation |
| PPG-15 SE; Octyldodec; Cocoglucoside + Coconut alcohol | Minocycline | | 0.87 |
| | 4-Epiminocycline | Not performed | 0.10 |
| | Visual inspection Compatibility Results | Yellow mixture compatible no oxidation | Yellow mixture compatible no oxidation |

Abbreviations:
PPG-15 SE.—Polypropylene Glycol Stearyl Ether
Octyldodec.—octyldodecanol It should be understood that the results displayed in Table 13a to 13e provide for a new methodology in defining the compatibility between unstable active agents and one or more components in a composition or formulation. Not only are these results applicable for preparing pharmaceutical compositions with unstable active agents, which is a very useful embodiment of the present disclosure, but this methodology also provides new information regarding the combination of different components/ingredients in the preparation of carriers, compositions and formulations per se (excluding an active ingredient). Thus, the results of Table 20 provide for definition of "unstable active agent-compatible (UAAC)" components or ingredients, which may be advantageously used in the preparation of stable compositions. Thus, "unstable active agent-compatible (UAAC)" components tend to be useful in the preparation of stable formulations with/without an active agent.

Part B Doxycycline

A similar compatibility study was conducted for Doxycycline Hyclate and Doxycycline Monohydrate.

The physicochemical properties of these two forms of Doxycycline are similar to those of other tetracycline antibiotics with the exception of differences resulting from prima facie the presence of a $H_2O$ molecule in Doxycycline Monohydrate and a $H_2O$ molecule and two HCl molecules for every water molecule in Doxycycline Hyclate.

General properties of Doxycycline Hyclate and Doxycycline Monohydrate:

Doxycycline Hyclate
1. Doxycycline Hyclate is a broad-spectrum antibiotic synthetically derived from oxytetracycline.
2. Doxycycline hyclate is a yellow crystalline powder soluble in water and in solutions of alkali hydroxides and carbonates.
3. Doxycycline hyclate has a high degree of lipid solubility and a low affinity for calcium binding.

Doxycycline Monohydrate
1. Doxycycline is a broad-spectrum antibiotic synthetically derived from oxytetracycline.
2. The chemical designation of the light-yellow crystalline powder is alpha-6-deoxy-5-oxytetracycline.

The major degradative pathways for both types of Doxycycline are carbon-4 epimerization and oxidative processes.

Doxycycline is a member of the tetracycline antibiotics group and is commonly used to treat a variety of infections, particularly effective in treating acne condition.

Different compositions of hydrophilic and hydrophobic solvents containing Doxycycline Hyclate (Set I and Set II) and Doxycycline Monohydrate (Set III) were prepared by weighing the antibiotic in a glass vial and shaking overnight with each solvent investigated. Mixtures of Doxycycline salts 1.04% w/w with solid excipients were prepared in a similar way as for Minocycline HCl. The results are presented in Tables 14a to 17.

TABLE 14a

Doxycycline Hyclate Compatibility Test (Group I)

Mixtures of 1.04% w/w of Doxycycline Hyclate stored at 25° C., 40° C. and 50° C. for two weeks
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| Visual inspection at T-0 | White liquid and yellow powder sedim. | White liquid and yellow powder sedim. | White liquid and yellow powder sedim. | White liquid and yellow powder sedim. | Light yellow solution | Light yellow solution | Light yellow solution | Light yellow solution | White liquid and yellow powder sedim. | White liquid and yellow powder sedim. |
| Visual inspection after the storage at 25° C. | White liquid and yellow powder sedim. | White liquid and yellow powder sedim. | White liquid and yellow powder sedim. | White liquid and yellow powder sedim. | Light yellow solution | Light yellow solution | Light yellow solution | Light yellow solution | White liquid and yellow powder sedim. | White liquid and yellow powder sedim. |
| Visual inspection | White liquid and | White liquid and | Light orange | White liquid and | Yellow solution | brownish Yellow | Brown solution | Orange solution | White liquid and | White liquid and |

TABLE 14a-continued

Doxycycline Hyclate Compatibility Test (Group I)

Mixtures of 1.04% w/w of Doxycycline Hyclate stored at 25° C., 40° C. and 50° C. for two weeks
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| after the storage at 40° C. | yellow powder sedim. | yellow powder sedim. | solution | yellow powder sedim. | | solution | | | yellow powder sedim. | yellow powder sedim. |
| Visual inspection after the storage at 50° C. | White liquid and yellow powder sedim. | White liquid and yellow powder sedim. | Orange solution | White liquid and yellow powder sedim. | Brownish orange solution | Light brown solution | Orange solution | Orange solution | White liquid and yellow powder sedim. | White liquid and yellow powder sedim. |
| Compatibility Results after the storage | Compat. no oxidation | Compat. no oxidation | Non compat. no oxidation | Compat. no oxidation | Non compat.. oxidation | Non compat. oxidation | Non compat. oxidation | Non compat. oxidation | Compat. no oxidation | Compat no oxidation |

TABLE 14b

Doxycycline Hyclate Compatibility Test (Group I) (continued)

Mixtures of 1.04% w/w of Doxycycline Hyclate stored at 25° C., 40° C. and 50° C. for two weeks
Ingredients

| Group I | Cetearyl octanoate | Hexylene glycol | Butylene glycol | Sorbitan Monolaurate | Dimethyl Isosorbide |
|---|---|---|---|---|---|
| Visual inspection at T-0 | bright yellow solution | bright yellow solution | bright yellow solution | bright yellow mixture | yellow solution |
| Visual inspection after the storage at 25° C. | bright yellow solution | bright yellow solution | bright yellow solution | Brown solution | Yellow solution |
| Visual inspection after the storage at 40° C. | bright yellow solution | light yellow solution | Light orange solution | Brown solution | Brownish orange |
| Visual inspection after the storage at 50° C. | White liquid and yellow powder sedim. | Light yellow liquid and yellow powder sedim. | Light orange solution | Black solution | Orange solution |
| Compatibility Results | Compat. no oxidation | Compat. no oxidation | Non compat. oxidation | Non compat. oxidation | Non compat.. Oxidation |

Group II included Doxycycline Hyclate mixed with various vehicles with addition of antioxidants like alpha tocopherol, butylated hydroxytolyene (BHT), ascorbic acid.

TABLE 15

Doxycycline Hyclate Compatibility Test (Group II)

Mixtures of 1.04% w/w of Doxycycline Hyclate stored at 25° C., 40° C. and 50° C. for two weeks
Ingredients

| Group II | Ethanol 95% | Ethanol 95% and BHT | Ethanol 95%, BHT and and ascorbic acid | Propylene glycol, alpha tocopherol and ascorbic acid | PEG 200, alpha tocopherol and ascorbic acid |
|---|---|---|---|---|---|
| Visual inspection at T-0 | bright yellow solution | bright yellow solution | bright yellow solution | bright yellow solution | bright yellow solution |
| Visual inspection after the storage at 25° C. | bright yellow solution | bright yellow solution | Yellow solution | bright yellow solution | Yellow solution |
| Visual inspection after the storage at 40° C. | bright yellow solution | bright yellow solution | Yellow solution | Light orange solution | Orange solution |
| Visual inspection after the storage at 50° C. | bright yellow solution | bright yellow solution | Orange solution | Light orange solution | Brownish orange solution |
| Compatibility Results | compatible. no oxidation | compatible no oxidation | Non compatible. oxidation | Non compatible. oxidation | non compatible. Oxidation |

TABLE 16

Doxycycline Hyclate Compatibility Test (Group III)

Mixtures of 1.04% w/w of Doxycycline Hyclate stored at 25° C., 40° C. and 50° C. for 3 days
Ingredients

| Group II | Isostearic Acid | Oleyl alcohol | Steareth 20 and Steareth 2 | Hydrogenated Castor Oil | Myristyl alcohol and Stearyl alcohol | PEG 40 Stearate | PEG 100 Stearate | Sorbitan Monostearate | Cocoglycerides |
|---|---|---|---|---|---|---|---|---|---|
| Visual inspection at T-0 | Yellow suspen | Yellow suspen | Yellow suspen | Yellow suspen | Yellow suspen | Yellow suspen | Yellow suspen | Yellow suspen | Yellow suspen |
| Visual inspection after the storage at 25° C. | Yellow suspen | Yellow suspen | Yellow suspen | Yellow suspen | Yellow suspen | Yellow suspen. | Yellow suspen | Yellow suspen | Yellow suspen |
| Visual inspection after the storage at 40° C. | Yellow suspen | Yellow suspen | Brown suspen | Yellow suspen | Yellow suspen | Brown suspen | Yellow suspen | Yellow suspen | Yellow suspen |
| Visual inspection after the storage at 50° C. | Yellow suspen | Yellow suspen | Brown suspen | Yellow suspen | Yellow suspen | Brown suspen | Yellow suspen | Yellow suspen | Light brown powder |
| Compatibility Results | Compat.. no oxidation | Compat. No oxidation | Non compat. Oxidation | Compat. No oxidation | Compat. No oxidation | Non Compat. oxidation | Compat.. No oxidation | Compat. No oxidation | Non Compat. oxidation | suspen.—suspension;
Compat.—compatible

A similar compatibility test was performed on another form of Doxycycline-Doxycycline Monohydrate. The results are presented in Table 17a. Table 17b and Table 18.

TABLE 17a

Doxycycline Monohydrate Compatibility Test (Group I)

Mixtures of 1.04% w/w of Doxycycline Monohydrate stored at 25° C., 40° C., and 50° C. for two weeks
Ingredients

| Group I | Cyclomethicone | PPG-15 stearyl ether | Octyldodecanol | Mineral oil | Propylene glycol | Glycerol | PEG 200 | PEG 400 | MCT oil | Diisopropyl adipate |
|---|---|---|---|---|---|---|---|---|---|---|
| Visual inspection at T-0 | White liquid and yellow powder sedim. | White liquid and yellow powder sedim. | White liquid and yellow powder sedim. | White liquid and yellow powder sedim. | Light yellow solution | yellow solution | yellow solution | Dark yellow solution | White liquid and yellow powder sedim. | White liquid and yellow powder sedim. |
| Visual inspection after the storage at 25° C. | White liquid and yellow powder sedim. | White liquid and yellow powder sedim. | White liquid and yellow powder sedim. | White liquid and yellow powder sedim. | Orange solution | yellow solution | Yellowish black solution | Yellowish brown solution | White liquid and yellow powder sedim. | White liquid and yellow powder sedim. |
| Visual inspection after the storage at 40° C. | White liquid and yellow powder sedim. | Yellowish orange mixture | orange solution | White liquid and yellow powder sedim. | Black solution | black solution | Black solution | Brown solution | White liquid and yellow powder sedim. | White liquid and yellow powder sedim. |
| Visual inspection after the storage at 50° C. | White liquid and yellow powder sedim. | Yellowish orange mixture | Orange solution | White liquid and yellow powder sedim. | black solution | black solution | Black solution | Black solution | Dirty yellow | Brown mixture |
| Compatibility Results after the storage | Compat. no oxidation | Non compat. oxidation | Non compat. oxidation | Compat. no oxidation | Non compat. oxidation | Non compat. oxidation | Non compat. oxidation | Non compat. oxidation | Non compat. oxidation | Non compat. oxidation |

TABLE 17b

Doxycycline Monohydrate Compatibility Test (Group I) (continued)

Mixtures of 1.04% w/w of Doxycycline Monohydrate stored at 25° C., 40° C., and 50° C. for two weeks Ingredients

| Group I | Cetearyl octanoate | Hexylene glycol | Butylene glycol | Sorbitan Monolaurate | Dimethyl Isosorbide |
|---|---|---|---|---|---|
| Visual inspection at T-0 | White liquid and yellow powder sedim. | White liquid and yellow powder sedim. | White liquid and yellow powder sedim. | Brown mixture | yellow solution |
| Visual inspection after the storage at 25° C. | White liquid and yellow powder sedim. | bright yellow solution | Orange solution | orange solution | orange solution |
| Visual inspection after the storage at 40° C. | White liquid and yellow powder sedim. | Brownish black solution | Brownish black solution | Brown solution | orange orange |
| Visual inspection after the storage at 50° C. | White liquid and yellow powder sedim. | Black solution. | black solution | brown solution | Orange solution |
| Compatibility Results | compat. no oxidation | Non compat. oxidation | Non compat. oxidation | Non compat. oxidation | non compat.. Oxidation |

TABLE 18

Doxycycline Monohydrate Compatibility Test (Group II)

Mixtures of 1.04% w/w of Doxycycline Monohydrate stored at 25° C., 40° C., and 50° C. for two weeks Ingredients

| Group II | Ethanol 95% | Eathnol 95% and BHT | Ethanol 95%, BHT and ascorbic acid | Propylene glycol, alpha tocopherol and ascorbic acid | PEG 200, alpha tocopherol and ascorbic acid |
|---|---|---|---|---|---|
| Visual inspection at T-0 | bright yellow solution | bright yellow solution | bright yellow solution | bright yellow solution | bright yellow solution |
| Visual inspection after the storage at 25° C. | Brown solution | Brown solution | orange solution | Yellowish orange solution | Yellow solution |
| Visual inspection after the storage at 40° C. | Brown solution | Brown solution | Orange solution | Orange solution | Dark yellow solution |
| Visual inspection after the storage at 50° C. | Black solution | Black solution | Black solution | Brownish orange solution | Brown orange solution |
| Compatibility Results | Non compatible. oxidation | Non compatible oxidation | Non compatible. oxidation | Non compatible. oxidation | non compatible. Oxidation |

Interesting and unexpected phenomena were found during the compatibility studies of Minocycline HCl, Doxycycline Hyclate and Doxycycline Monohydrate:

1. Whilst Minocycline displayed intensive oxidation on dissolution in glycerol. Surprisingly, the antibiotic revealed full compatibility with octyldodecanol, a branched chain fatty alcohol. Both molecules have the similar hydroxyl units in their structures.

2. Doxycycline Hyclate and Monohydrate unexpectedly revealed different compatibility with excipients. For example, Doxycycline Hyclate was stable in mixture with PPG-15 Stearyl Ether. Surprisingly, the Doxycycline Monohydrate was found to be non compatible with PPG-15 Stearyl Ether during the storage at 40° and 50° C. for two weeks.

3. Doxycycline Hyclate was stable in mixture with ethanol 95% and hexylene glycol. Doxycycline Monohydrate oxidized in the similar mixtures.

4. Unexpectedly addition of strong anti oxidants like alpha-tocopherol and ascorbic acid did not prevent the oxidation of any of Minocycline HCL, Doxycycline Hyclate and Monohydrate in a waterless medium of propylene glycol and PEG 200.

5. Surprisingly, Doxycycline Hyclate revealed stability in Ethanol 95% following the storage at 40° C. and 50° C. for two weeks although Minocyline HCl and Doxycycline Monohydrate changed their colour from yellow to orange upon dissolution in Ethanol 95%.

6. In conclusion the following non predictable substance were found to be compatible with Minocycline and Doxycycline:

TABLE 19

Summary of MCH and DOX compatibility studies

Compatibility tested after the storage for up to 3 weeks

| Ingredient | Minocycline HCL | Doxycycline Hyclate | Doxycycline Monohydrate | Comments |
|---|---|---|---|---|
| Cyclomethicone 5 NF | Yes | Yes | Yes | All compatible |
| PPG-15 Stearyl Ether | Yes | Yes | No | |
| Octyldodecanol | Yes | No | No | |
| Mineral Oil | Yes | Yes | Yes | All compatible |
| Propylene Glycol | No | No | No | |
| Glycerol | No | No | No | |
| PEG 200 | No | No | No | |
| PEG 400 | No | No | No | |
| MCT Oil | Yes | Yes | No | |
| Diisopropyl adipate | Yes | Yes | No | |
| Ethanol 95% | No | Yes | No | |
| Isostearic acid | No | Yes | Not tested | |
| Oleyl alcohol | Yes | Yes | Not tested | |
| Steareth 20 (Polyoxyl 20 Stearyl Ether) | No | No | Not tested | |
| Steareth 2 (Polyoxyl 2 Stearyl Ether) | No | No | Not tested | |
| Methyl glycose sesquistearate (MGSS) | No | Not tested | Not tested | |
| Aluminum Starch Octenylsuccinate (ASOS) | Yes | Not tested | Not tested | |
| Cetearyl octanoate | Yes | Yes | Yes | All compatible |
| Hydrogenated Castor Oil | Yes | Yes | Not tested | |
| Stearyl alcohol | Yes | Yes | Not tested | |
| Myristyl alcohol | Yes | Yes | Not tested | |
| Titanium Dioxide | Yes | Not tested | Not tested | |
| PEG 40 stearate | Yes | No | Not tested | |
| PEG 100 Stearate | Yes | Yes | Not tested | |
| Sorbitan Monostearate | Yes | Yes | Not tested | |
| Cocoglycerides | Yes | No | Not tested | |
| Coconut Alcohol | yes | Not tested | Not tested | |
| Hexylene glycol | No | Yes | No | |
| Butylene glycol | No | No | No | |
| Sorbitan Monolaurate | No | No | No | |
| Dimethyl Isosorbide | No | No | No | |
| Titanium dioxide | Yes | Not tested | Not tested | |
| Methyl glycose sesquistearate (MGSS) | No | Not tested | Not tested | |
| Aluminum Starch Octenylsuccinate (ASOS) | Yes | Not tested | Not tested | |
| Coconut alcohol | Yes | Not tested | Not tested | |

7. As could be seen from the Table 19 not all the compatible with MCH ingredients are compatible with Doxycycline Hyclate or Monohydrate. For example, octyldodecanol is compatible with Minocycline HCl but revealed incompatibility with Doxycycline Hyclate and Monohydrate. Surprisingly, there are discrepancies in list of ingredients compatible with Doxycycline Hyclate and Doxycycline Monohydrate: for example PPG-15 Stearyl Ether is compatible with Doxycycline Hyclate and non compatible with Doxycycline Monohydrate.

8. The data presented herein could be used for selection of active materials from tetracycline family for topical formulations. A list of ingredients that were found to be compatible with MCH and DOX could be applied to other antibiotics from the tetracycline family. The following ingredients are suitable for topical formulations: mineral oil, cyclomethicone, cetearyl octanoate. Few ingredients are compatible with both forms of doxycycline and are also compatible with minocycline.

Example 4

Various Comparative Examples of Doxycycline and Minocycline Formulations

The formulation of MCH072 is described in Table 20 below. Table 21 describes compositions that failed to provide foam of any quality.

TABLE 20

Formulation of MCH072 stock solution

| chemical name | MCH072--stock solution |
|---|---|
| PPG-15 Stearyl Ether | 15.00 |
| Octyldodecanol | 12.00 |
| Light mineral oil | 55.50 |
| Cyclomethicone | 3.00 |
| Glyceryl monostearate | 6.00 |
| Stearyl alcohol | 6.00 |

TABLE 20-continued

Formulation of MCH072 stock solution

|  | MCH072--stock solution |
|---|---|
| Myristyl alcohol | 2.50 |
| Control: | 100.00 |
| propellant (1681) | |
| RESULTS | |
| FOAM | |
| foam quality | G |
| Color | White |
| Odor | no odor |
| shakability | Good |
| Collapse time (36 C-sec.) | 300/G |
| bubble mean size (μm) | 105.00 |
| Bubbles above 500 μm (%) | 0.00 |
| PFF | |
| viscosity | 5166.90 |
| centrifugation (1K) | separation |

TABLE 21

Comparative compositions that do not provide foam of any quality

|  | EXA2 pressurized with Hydrocarbon | EXA3 Pressurized with hydrocarbon | EXA2 pressurized with fluorocarbon |
|---|---|---|---|
| Caprylic/Capric Triglyceride | 25.50 | 24.50 | 25.50 |
| light Mineral Oil | 8.00 | 11.00 | 8.00 |
| Cyclomethicone | 20.00 | 32.00 | 20.00 |
| Beeswax | 1.50 | 1.50 | 1.50 |
| Sorbitan Monooleate (span 80) | 4.50 | 6.00 | 4.50 |
| Hydrogenated Castor Oil | 0.50 |  | 0.50 |
| Zinc Oxide | 40.00 |  | 40.00 |
| Petrolatum (pioner 5464) |  | 25.00 |  |
| Control: | 100.00 | 100.00 | 100.00 |
| propellant (1681-propane + butane + isobutane) | 8.00 | 8.00 |  |
| Fluorocarbon Dymel 134 ap |  |  | 15.00 |
| RESULTS | | | |
| FOAM | | | |
| foam quality | P | P | P |
| Color | white | white | white |
| Odor | no odor | no odor | no odor |
| Shakability | good | good | good |
| Collapse time (RT-sec.) | <20 | <10 | <20 |
| PFF | | | |
| Viscosity | 5934.00 | 1011.78 | 5934.00 |
| centrifugation (1K) | separation | stable | separation |

P = Poor

The EXA-based formulations broke down immediately and did not produce good foams. Changing the propellant did not help In contrast previous MCH-based formulations produced good quality foams which had a collapse time in excess of 4-5 minutes.

Additionally, the results with minocycline and doxycycline provide indications of stable formulations for topical administration of tetracycline antibiotics that may also include stable active ingredients.

Additional minocycline formulations are provided in the following Tables 22 to 25

TABLE 22

Additional formulations of Minocycline HCl foam

|  | PMCH001 | PMCH002 | PMCH003 | PMCH004 | PMCH005 |
|---|---|---|---|---|---|
| PPG-15 Stearyl ether | 5.00 | 50.00 | 84.32 |  | 40.00 |
| Octyldodecanol | 12.00 | 12.00 |  | 12.00 |  |
| Light Mineral Oil | 67.32 | 22.32 |  | 72.32 | 44.32 |
| Glycerol Monostearate | 6.00 | 6.00 | 6.00 | 6.00 | 6.00 |
| Stearyl alcohol | 6.00 | 6.00 | 6.00 | 6.00 | 6.00 |
| Myristyl alcohol | 2.50 | 2.50 | 2.50 | 2.50 | 2.50 |
| Minocycline HCl | 1.18 | 1.18 | 1.18 | 1.18 | 1.18 |
| Total | 100.00 | 100.00 | 100.00 | 100.00 | 100.00 |
| Propellant (1681) | 12.00 | 12.00 | 12.00 | 12.00 | 12.00 |
| Results | | | | | |
| Viscosity | 7934.31 | 12189.4 | 14412.92 | 10925.67 | 2783.41 |
| Quality | G | G | FG | G | FG to G |
| Color | slight yellow | slight yellow | slight yellow | slight yellow | slight yellow |
| Odor | no odor | v.f.odor | v.f.odor | no odor | no odor |
| Shakability | 2 | 2 | 2 | 2 | 2 |
| collapse time | 300/G | >300/FG | N/R | >300/FG | 180/FG |
| Density | 0.127 | 0.138 | N/R | 0.127 | 0.100 |
| bubble size (μm) | 96 | 88 | 405 | 100.00 | 186.00 |
| bubble size (above 500 μm) | 0 | 0 | 26.9 | 0.00 | 3.30 |

G = Good;
FG = Fairly Good

Comments:

The influence of PPG-15 Stearyl ether concentrations foam quality was tested in formulations PMCH-001 to PMCH-003. The study revealed that at concentration of around 80% w/w foam quality failed down from good to fairly good.

Formulation showed good foam quality without PPG-15 stearyl ether and minimal concentration of octyldodecanol (see examples PMCH 004 and 005).

This result means that we can produce high quality foam without PPG-15 Stearyl ether.

Manufacturing Procedure for PMCH001 to PMCH 018 formulations

Heat all ingredients to 70° C. to complete dissolution.
Cool to 25° C. Add Minocycline by continuous stirring.

TABLE 23

Additional formulations of Minocycline HCl foam (Continued)

|  | PMCH006 | PMCH007 | PMCH008 | PMCH009 | PMCH010 | PMCH011 |
|---|---|---|---|---|---|---|
| PPG-15 Stearyl ether | 12.00 | 12.00 |  |  |  |  |
| Octyldodecanol | 5.00 | 50.00 | 84.32 | 12.00 | 12.00 |  |
| Oleyl alcohol |  |  |  | 5.00 | 50.00 | 84.32 |
| Light Mineral Oil | 67.32 | 22.32 |  | 67.32 | 22.32 |  |
| Glycerol Monostearate | 6.00 | 6.00 | 6.00 | 6.00 | 6.00 | 6.00 |
| Stearyl alcohol | 6.00 | 6.00 | 6.00 | 6.00 | 6.00 | 6.00 |
| Myristyl alcohol | 2.50 | 2.50 | 2.50 | 2.50 | 2.50 | 2.50 |
| Minocycline HCl | 1.18 | 1.18 | 1.18 | 1.18 | 1.18 | 1.18 |
| Total | 100.00 | 100.00 | 100.00 | 100.00 | 100.00 | 100.00 |
| Propellant (1681) | 12.00 | 12.00 | 12.00 | 12.00 | 12.00 | 12.00 |
| Results |  |  |  |  |  |  |
| Viscosity | 4335.07 | 5102.91 | 5582.81 | 5422.84 | 1985.57 | 668.86 |
| Quality | G | G | F | G | FG | P |
| Color | slight yellow | slight yellow | slight yellow | slight yellow | slight yellow | slight yellow |
| Odor | no odor | no odor | no odor | no odor | no odor | no odor |
| Shakability | 2 | 2 | 2 | 2 | 2 | 2 |
| collapse time | >300/G | 300/FG | N/R | >300/FG | N/R | N/R |
| Density | 0.137 | 0.151 | N/R | 0.103 | N/R | N/R |
| bubble size (μm) | 180.00 | 185.00 | N/R | 142 | 212 | N/R |
| bubble size (above 500 μm) | 0.00 | 3.60 |  | 0 | 7.1 |  |

G = Good;
FG = Fairly Good;
F = Fair;
P = Poor

Comments:

The same conclusion as was previously made regarding PPG-15 stearyl ether could be applied regarding the influence of octyldodecanol concentration on MCH foam quality namely: high concentration of octyldodecanol reduces foam quality. Addition of oleyl alcohol in substantial amounts reduced the foam quality.

TABLE 24

Additional formulations of Minocycline HCl foam (Continued)

|  | PMCH012 | PMCH013 | PMCH014 | PMCH015 |
|---|---|---|---|---|
| PPG-15 Stearyl ether |  |  | 15.00 | 15.00 |
| Octyldodecanol | 12.00 | 12.00 | 12.00 | 12.00 |
| Oleyl alcohol | 67.32 | 22.32 |  |  |
| Cyclomethicone | 5.00 | 50.00 | 3.00 | 3.00 |
| Jojoba oil |  |  | 54.32 |  |
| Peppermint oil |  |  |  | 54.32 |
| Glycerol Monostearate | 6.00 | 6.00 | 6.00 | 6.00 |
| Stearyl alcohol | 6.00 | 6.00 | 6.00 | 6.00 |
| Myristyl alcohol | 2.50 | 2.50 | 2.50 | 2.50 |
| Minocycline HCl | 1.18 | 1.18 | 1.18 | 1.18 |
| Total | 100.00 | 100.00 | 100.00 | 100.00 |
| Propellant (1681) | 12.00 | 12.00 | 12.00 | 12.00 |
| Results |  |  |  |  |
| Viscosity | 139.97 | 5454.84 | 8030.23 | 221.95 |
| Quality | F | FG | G | P |
| Color | slight yellow | slight yellow | slight yellow | slight yellow |
| Odor | no odor | no odor | no odor | menta |
| Shakability | 2 | 2 | 2 | 2 |
| collapse time | N/R |  |  | N/R |
| Density | N/R | N/R | N/R | N/R |
| bubble size (μm) | 148 | N/R | 55 |  |
| bubble size (above 500 μm) | 3.8 |  | 0 |  |

G = Good;
FG = Fairly Good;
F = Fair;
P = Poor

Comments:

High concentrations of cyclomethicone destroyed the foam.

Addition of therapeutic oils like jojoba oil revealed good foam quality. Addition of peppermint oil totally destroyed the foam (see formulations PMCH014 and 015)

TABLE 24A

Additional formulations of Minocycline HCl foam

|  | PMCH016-Placebo | PMCH016-(1% API) | PMCH016 (5% API) | PMCH016 (10% API) |
|---|---|---|---|---|
| PPG-15 Stearyl ether | 15.00 | 15.00 | 14.25 | 13.50 |
| Octyldodecanol | 12.00 | 12.00 | 11.41 | 10.80 |
| Oleyl alcohol | 55.50 | 54.30 | 52.73 | 49.95 |
| Cyclomethicone | 3.00 | 3.00 | 2.85 | 2.70 |
| Glycerol Monostearate | 6.00 | 6.00 | 5.70 | 5.40 |
| Stearyl alcohol | 6.00 | 6.00 | 5.70 | 5.40 |
| Myristyl alcohol | 2.50 | 2.50 | 2.38 | 2.25 |
| Minocycline HCl |  | 1.18 | 5.00 | 10.00 |
| Total | 100.00 | 100.00 | 100.00 | 100.00 |
| Propellant (1681) | 12.00 | 12.00 | 12.00 | 12.00 |
| Results |  |  |  |  |
| Viscosity | 48.99 | 127.97 | 6670.58 | 424.91 |
| Quality | FG | P | FG | FG |
| Color | white | slight yellow | yellow | yellow |
| Odor | no odor | v.f.odor | v.f.odor | v.f.odor |
| Shakability | 2 | 2 | 2 | 2 |
| collapse time | N/R | N/R | N/R | N/R |
| Density | N/R | N/R | N/R | N/R |

G = Good;
FG = Fairly Good;
F = Fair;
P = Poor

TABLE 25

Additional formulations of Minocycline HCl foam

|  | PMCH017-Placebo | PMCH017 (1% API) | PMCH017 (5% API) | PMCH017 (10% API) |
|---|---|---|---|---|
| PPG-15 Stearyl ether | 15.00 | 14.82 | 14.25 | 13.50 |
| Octyldodecanol | 12.00 | 11.86 | 11.40 | 10.80 |
| Cyclomethicone | 3.00 | 2.96 | 2.85 | 2.70 |
| Light Mineral Oil | 55.50 | 54.85 | 52.72 | 49.95 |
| Glycerol Monostearate | 6.00 | 5.93 | 5.70 | 5.40 |
| Stearyl alcohol | 6.00 | 5.93 | 5.70 | 5.40 |
| Myristyl alcohol | 2.50 | 2.47 | 2.38 | 2.25 |
| Minocycline HCl |  | 1.18 | 5.00 | 10.00 |
| Total | 100.00 | 100.00 | 100.00 | 100.00 |
| Propellant (1681) | 12.00 | 12.00 | 12.00 | 12.00 |
| Results |  |  |  |  |
| Viscosity | 7630.37 | 2543.45 | 7918.31 | 2703.42 |
| Quality | G | G | G | G |
| Color | white | slight yellow | yellow | yellow |
| Odor | no odor | no odor | no odor | no odor |
| Shakability | 2 | 2 | 2 | 2 |
| collapse time | 190/F | 240/F | 300/FG | >300/FG |
| Density | 0.077 | 0.117 | 0.120 | 0.143 |

G = Good;
FG = Fairly Good;
F = Fair;
P = Poor

Comments:

Impact of various concentrations of Minocycline HCl on foam quality was tested in formulations PMCH-016 (1% API); (5% API), (10% API). Addition of higher concentration of Minocycline HCl to placebo formulation did not improve the foam quality.

Formulations PMCH 017 (1% API), (5% API), (10% API) revealed good foam quality as well as placebo PMCH017.

All the formulations herein, which were found to be useful carriers for doxycycline or minocycline can be usefully used as carriers for other active agents. In some embodiments the active agents may be sensitive and in other embodiments they may be non sensitive, In certain embodiments they are insoluble and in certain other embodiments they are soluble. By way of a non limiting Example both the minocycline formulation MCH-072 and the parallel doxycycline formulation DOX-033, which were found to be compatible with all of Minocycline HCL (MCH), Doxycycline Hyclate or Doxycycline Monohydrate (DOX) have also been shown above to be a useful carrier with clindamycin phosphate, pimicrolimus, and diclofenac potassium, Calcipotriol, vitamin A acetate, Betamethasone 17-valerate, Ciclopiroxolamine, Benzoyl Peroxide and Coal Tar Extract (ethanol). It follows that other similar formulations based on an oil/silicone/surfactant composition will also provide excellent carriers for these and other active agents.

Example 5

Hydration Studies

The hydration effect of Placebo PMCH017 formulation was tested on healthy volunteers by corneometer. The market anti acne product PanOxyl and moisturizer Cetaphil cream were tested for comparision. The Placebo formulation without any active hydration agent was found to improve hydration of the skin by about 5% and did not cause a skin drying effect observed with the PanOxyl cream.

General Study Design

Healthy subjects received one treatment of each of the study medications and reference products (as applicable) and were followed up to determine the levels of skin hydration using the Corneometer® CM 825 instrument. (Courage+ Khazaka, Germany).

Study Flow Chart

| Study Activity | Baseline* | 1 hour | 3 hours | 6 hours |
|---|---|---|---|---|
| Application of the test preparations | x |  |  |  |
| Assessment of skin hydration | x | X | X | X |

*Before treatment

Study Procedures
a. Subjects were presented on the day of the study one hour ahead of the study initiation.
b. The subjects were accommodated in a calm, quiet, temperature controlled room (20-24° C.) and pleasant surroundings.
c. Subjects were wash their forearms with water (no soap) and were dry the forearms with dry paper towel.
d. Application sites were marked according to one of the following options:
  i. Four squares, 4 cm×4 cm (16 cm2) were drawn symmetrically on the forearms of each subject (2 areas on each forearms). Areas were numbered from 1 to 4. One for each study formulation and one for the no-treatment (control).

The formulations were named with letters from B to D (PMCH017P-080113, Cetaphil, PanOxyl) and A (for control).

e. Each study formulation, as well as control products and "no-treatment" were randomly assigned to the treatment sites according to a randomization list, provided by the study statistician.

f. The treatments on each square were blind for the study operator.

g. An amount between 40 mg (2.5 mg/cm2) of each of the study formulation, were applied evenly on the treatment sites according to a randomization list h. Skin hydration level were assessed at baseline (at least 15 minutes after each subject washed their forearms), using the Corneometer® CM 825, and then 1 hour, 3 hours and 6 hours after the application. Three repeated measurements were recorded at each time point. Results are shown in FIG. 1.

PanOxyl List contains: 5% Benzoyl Peroxide in o/w emulsion.

Cetaphil contains: water, cetyl alcohol, propylene glycol, sodium lauryl sulfate, stearyl alcohol, methylparaben, propylparaben, butylparaben.

It is appreciated that certain features, which are, for clarity, described in the context of separate embodiments, may also be provided in combination in a single embodiment. Conversely, various features, which are, for brevity, described in the context of a single embodiment, may also be provided separately or in any suitable subcombination. Although the present disclosure has been described in conjunction with specific embodiments thereof, it is evident that many alternatives, modifications and variations will be apparent to those skilled in the art.

The invention claimed is:

1. A topical tetracycline antibiotic composition comprising a foamable pharmaceutical composition and a propellant, the foamable pharmaceutical composition comprising:
   a) about 0.1% to about 10% by weight of the foamable pharmaceutical composition of a tetracycline antibiotic;
   b) about 60% to about 95% by weight of the foamable pharmaceutical composition of:
      at least one oily emollient, wherein the oily emollient is selected from the group consisting of PPG-15 stearyl ether, octyldodecanol, diisopropyl adipate, isostearic acid, and cetearyl octanoate;
      at least one oil, wherein the oil is a liquid hydrocarbon-based oil; or
      a combination of at least one oily emollient and at least one oil;
   c) about 0.01% to about 15% by weight of the foamable pharmaceutical composition of at least one surfactant, wherein the surfactant is a fatty acid ester, having a C8-C24 saturated hydrocarbon chain;
   d) optionally 0.01% to about 10% by weight of the foamable pharmaceutical composition of at least one foam adjuvant, wherein the foam adjuvant is a fatty alcohol or a cocoglyceride; and
   wherein each component is tetracycline-compatible;
   wherein the composition comprises less than about 2% by weight of the foamable pharmaceutical composition of water;
   wherein at least 90% by mass of the tetracycline antibiotic is present in the foamable pharmaceutical composition when stored for 72 hours at 25° C. after mixing with the pharmaceutical composition; and
   wherein the weight ratio of the foamable pharmaceutical composition to the propellant is about 100:5 to about 100:35.

2. The topical tetracycline antibiotic composition of claim 1, wherein the oil is selected from the group consisting of a plant-based oil, a mineral oil, a triglyceride, an essential oil, and an animal-based oil.

3. The topical tetracycline antibiotic composition of claim 2, wherein the oil is selected from the group consisting of light mineral oil, MCT oil, hydrogenated castor oil, jojoba oil, and peppermint oil.

4. The topical tetracycline antibiotic composition of claim 1, wherein the surfactant is a stearic acid derived ester; or
   wherein the surfactant is a monoglyceride or diglyceride; or
   wherein the surfactant is selected from the group consisting of glycerol monostearate, sorbitan monostearate, PEG 40 stearate, and PEG 100 stearate.

5. The topical tetracycline antibiotic composition of claim 1, wherein the foam adjuvant is selected from the group consisting of oleyl alcohol, stearyl alcohol, myristyl alcohol, and cocoglycerides.

6. The topical tetracycline antibiotic composition of claim 1, wherein the tetracycline antibiotic is selected from the group consisting of a minocycline, a doxycycline, minocycline hydrochloride, doxycycline hyclate, and doxycycline monohydrate.

7. The topical tetracycline antibiotic composition of claim 1, further comprising at least one of ethanol, aluminum starch octenyl succinate, titanium dioxide, coconut alcohol, and hexylene glycol.

8. The topical tetracycline antibiotic composition of claim 1, wherein chemical stability is determined by observing a color change in the foamable pharmaceutical composition.

9. The topical tetracycline antibiotic composition of claim 1, further comprising at about 0.1% to about 5% by weight of the foamable pharmaceutical composition of a silicone oil.

10. The topical tetracycline antibiotic composition of claim 9, wherein the silicone oil is cyclomethicone.

11. The topical tetracycline antibiotic composition of claim 1, further comprising at least one tetracycline-compatible additional active agent.

12. The topical tetracycline antibiotic composition of claim 1, wherein the tetracycline antibiotic is chemically stable in the foamable pharmaceutical composition when stored for about 3 weeks, wherein chemical stability is determined by measuring at least about 90% by mass of the tetracycline antibiotic at three weeks compared to time 0.

13. The topical tetracycline antibiotic composition of claim 1, wherein the foam adjuvant is a C14-C18 fatty alcohol.

14. The topical tetracycline antibiotic composition of claim 1, wherein at least 90% by mass of the tetracycline antibiotic is present in the foamable pharmaceutical composition when stored for 72 hours at 40° C. after mixing with the pharmaceutical composition, wherein chemical stability is determined by measuring at least about 90% by mass of the tetracycline antibiotic at 72 hours compared to time 0.

15. A method of treating a bacterial infection, the method comprising topically administering the topical tetracycline antibiotic composition of claim 1 to a subject in need of treatment, wherein the topical antibiotic composition is administered to one or more of skin, face, a mucosal membrane, a body cavity, the nose, the mouth, the eye, the ear canal, the respiratory system, the vagina, and the rectum.

16. A method of treating post-surgical adhesions, the method comprising topically administering the topical tetracycline antibiotic composition of claim 1 to a surgical site of a subject.

17. A topical tetracycline antibiotic composition comprising a foamable pharmaceutical composition and a propellant, the foamable pharmaceutical composition comprising:
   a) about 0.1% to about 10% by weight of the foamable pharmaceutical composition of minocycline or a salt thereof;
   b) about 60% to about 95% by weight of the foamable pharmaceutical composition of:
      at least one emollient selected from the group consisting of PPG-15 stearyl ether, octyldodecanol, diisopropyl adipate, and cetearyl octanoate[;
      at least one oil selected from the group consisting of light mineral oil, MCT oil, hydrogenated castor oil, jojoba oil, and peppermint oil; or
      a combination of at least one emollient and at least one oil;
   c) about 0.01% to about 15% by weight of the foamable pharmaceutical composition of at least one surfactant selected from the group consisting of a monoglyceride, a diglyceride, glycerol monostearate, sorbitan monostearate, PEG 40 stearate and PEG 100 stearate;
   d) optionally about 0% to about 10% by weight of the foamable pharmaceutical composition of at least one foam adjuvant selected from the group consisting of oleyl alcohol, stearyl alcohol, myristyl alcohol and cocoglycerides; and
   wherein each component is minocycline-compatible;
   wherein the composition comprises less than about 2% by weight of the foamable pharmaceutical composition of water;
   wherein at least 90% by mass of the minocycline or salt thereof is present in the foamable pharmaceutical composition when stored for 72 hours at 25° C. after mixing with the pharmaceutical composition; and
   wherein the weight ratio of the foamable pharmaceutical composition to the propellant is about 100:5 to about 100:35.

18. The topical tetracycline antibiotic composition of claim 17, wherein less than about 1% by mass of a 4-epiminocylcine is measured when the foamable pharmaceutical composition is stored for 72 hours at 25° C. compared to time 0.

19. The topical tetracycline antibiotic composition of claim 17 comprising minocycline hydrochloride.

20. A method of treating a bacterial infection, the method comprising topically administering the topical tetracycline antibiotic composition of claim 17 to a subject in need of treatment, wherein the topical antibiotic composition is administered to skin, a mucosal membrane, or a body cavity.

21. A method of treating post-surgical adhesions, the method comprising topically administering the topical tetracycline antibiotic composition of claim 17 to a surgical site of a subject.

22. A topical tetracycline antibiotic composition comprising a foamable pharmaceutical composition and a propellant, the foamable pharmaceutical composition comprising either A):
   a) about 0.1% to about 10% by weight of the foamable pharmaceutical composition of doxycycline or a salt thereof;
   b) about 60% to about 95% by weight of the foamable pharmaceutical composition of:
      at least one emollient selected from the group consisting of PPG-15 stearyl ether, diisopropyl adipate, and cetearyl octanoate;
      at least one oil selected from the group consisting of mineral oil and MCT oil; or
      a combination of at least one emollient and at least one oil;
   c) about 0.01% to about 15% by weight of the foamable pharmaceutical composition of at least one surfactant selected from the group consisting of a monoglyceride, a diglyceride, monostearate, sorbitan monostearate, hydrogenated castor oil, PEG 40 stearate and PEG 100 stearate;
   d) optionally about 0% to about 10% by weight of the foamable pharmaceutical composition of at least one foam adjuvant selected from the group consisting of stearyl alcohol, oleyl alcohol, isostearic acid and myristyl alcohol;
or B):
   a) about 0.1% to about 10% by weight of the foamable pharmaceutical composition of doxycycline or a salt thereof;
   b) about 60% to about 95% by weight of the foamable pharmaceutical composition of:
      at least one emollient selected from the group consisting of cetearyl octanoate, PPG-15 stearyl ether, propylene glycol, octyldodecanol, diisopropyl adipate, and isostearic acid;
      at least one oil selected from the group consisting of light mineral oil, MCT oil, and hydrogenated castor oil;
      or a combination of at least one emollient and at least one oil;
   c) about 0.01% to about 15% by weight of the foamable pharmaceutical composition of at least one surfactant selected from the group consisting of a monoglyceride, a diglyceride, glycerol monostearate, sorbitan monostearate, PEG 40 stearate, and PEG 100 stearate;
   d) about 1% to about 10% by weight of the foamable pharmaceutical composition of at least one foam adjuvant selected from the group consisting of oleyl alcohol, stearyl alcohol, myristyl alcohol and stearic acid;
      wherein each component is doxycycline-compatible;
      wherein the composition comprises less than about 2% by weight of the foamable pharmaceutical composition of water;
   wherein at least 90% by mass of the doxycycline or salt thereof is present in the foamable pharmaceutical composition when stored for 72 hours at 25° C. after mixing with the foamable pharmaceutical composition; and
   wherein the weight ratio of the foamable pharmaceutical composition to the propellant is about 100:5 to about 100:35.

23. The topical tetracycline antibiotic composition of claim 22 comprising doxycycline hyclate or doxycycline monohydrate.

24. A method of treating a bacterial infection, the method comprising topically administering the topical tetracycline antibiotic composition of claim 22 to a subject in need of treatment, wherein the topical antibiotic composition is administered to skin, a mucosal membrane, or a body cavity.

25. A method of treating post-surgical adhesions, the method comprising topically administering the topical tetracycline antibiotic composition of claim 22 to a surgical site of a subject.

* * * * *